US009296757B2

(12) United States Patent
Klar et al.

(10) Patent No.: US 9,296,757 B2
(45) Date of Patent: Mar. 29, 2016

(54) SUBSTITUTED BENZOTHIENOPYRIMIDINES

(71) Applicant: BAYER PHARMA AKTIENGESELLSCHAFT, Berlin (DE)

(72) Inventors: Ulrich Klar, Berlin (DE); Georg Kettschau, Berlin (DE); Dirk Kosemund, Berlin (DE); Florian Pühler, Wellesley, MA (US); Knut Eis, Berlin (DE); Philip Lienau, Berlin (DE); Ulf Bömer, Glienicke (DE); Detlev Sülzle, Berlin (DE); Lars Wortmann, Berlin (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 14/402,665

(22) PCT Filed: May 17, 2013

(86) PCT No.: PCT/EP2013/060220
§ 371 (c)(1),
(2) Date: Nov. 20, 2014

(87) PCT Pub. No.: WO2013/174735
PCT Pub. Date: Nov. 28, 2013

(65) Prior Publication Data

US 2015/0152121 A1 Jun. 4, 2015

(30) Foreign Application Priority Data

May 21, 2012 (EP) .................................... 12168672
Feb. 1, 2013 (EP) .................................... 13153616

(51) Int. Cl.

| | |
|---|---|
| ***C07D 495/04*** | (2006.01) |
| ***A61K 31/38*** | (2006.01) |
| ***A61K 31/519*** | (2006.01) |
| ***A61K 45/06*** | (2006.01) |
| ***C07D 519/00*** | (2006.01) |

(52) U.S. Cl.
CPC .............. *C07D 495/04* (2013.01); *A61K 31/38* (2013.01); *A61K 31/519* (2013.01); *A61K 45/06* (2013.01); *C07D 519/00* (2013.01)

(58) Field of Classification Search
CPC .............................. C07D 495/04; A61K 31/38
USPC .......................................... 544/250; 514/257
See application file for complete search history.

(56) References Cited

U.S. PATENT DOCUMENTS

| | | | |
|---|---|---|---|
| 3,760,806 | A | 9/1973 | Leeper et al. |
| 5,252,569 | A | 10/1993 | Hajos et al. |
| 6,395,733 | B1 | 5/2002 | Arnold et al. |
| 6,491,683 | B1 | 12/2002 | Dong et al. |
| 2001/0021822 | A1 | 9/2001 | Ayer |
| 2002/0183722 | A1 | 12/2002 | Harper et al. |
| 2003/0180757 | A1 | 9/2003 | McGall et al. |
| 2006/0183761 | A1 | 8/2006 | Ledeboer et al. |
| 2009/0142313 | A1 | 6/2009 | Talling et al. |
| 2009/0286812 | A1 | 11/2009 | Erickson et al. |
| 2011/0160203 | A1 | 6/2011 | Liu et al. |

(Continued)

FOREIGN PATENT DOCUMENTS

| | | | |
|---|---|---|---|
| EP | 1674466 | A1 | 6/2006 |
| EP | 1746096 | A1 | 1/2007 |

(Continued)

OTHER PUBLICATIONS

Hou et al., Targeting Mnks for Cancer Therapy, Oncotarget, vol. 3, No. 2, pp. 118-131 (2012).*
Pearce et al., Failure modes in anticancer drug discovery and development, Cancer Drug Design and Discovery Edited by Stephen Neidle, Chapter 18, pp. 424-435 (2008).*
Johnson et al., Relationships between drug activity in NCI preclinical in vitro and in vivo models and early clinical trials, British Journal of Cancer (2001) 64(10): 1424-1431.*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*

(Continued)

*Primary Examiner* — Deepak Rao

(57) ABSTRACT

The present invention relates to substituted benzothienopyrimidine compounds of general formula I: in which $R^{1a}$, $R^{1b}$, $R^{2a}$, $R^{2b}$, and $R^{2c}$ are as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyper-proliferative and/or angiogenesis disorder, as a sole agent or in combination with other active ingredients.

I

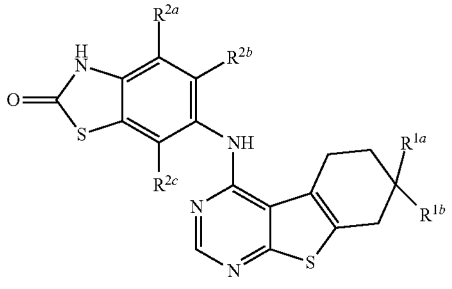

9 Claims, No Drawings

(56) References Cited

U.S. PATENT DOCUMENTS

| | | | |
|---|---|---|---|
| 2015/0133425 A1 | 5/2015 | Kettschau et al. | |
| 2015/0218173 A1 | 8/2015 | Wortmann et al. | |
| 2015/0239891 A1 | 8/2015 | Klar et al. | |
| 2015/0252047 A1 | 9/2015 | Klar et al. | |

FOREIGN PATENT DOCUMENTS

| | | | |
|---|---|---|---|
| GB | 1029696 | | 5/1966 |
| JP | 2007/084494 | A | 4/2007 |
| WO | 97/18212 | A1 | 5/1997 |
| WO | 98/23613 | A1 | 6/1998 |
| WO | 99/65908 | A1 | 12/1999 |
| WO | 02/088138 | A1 | 11/2002 |
| WO | 2005/010008 | A1 | 2/2005 |
| WO | 2005/047288 | A1 | 5/2005 |
| WO | 2005/111135 | A1 | 11/2005 |
| WO | 2006/017443 | A2 | 2/2006 |
| WO | 2006/136402 | A1 | 12/2006 |
| WO | 2007/023110 | A2 | 3/2007 |
| WO | 2007/059905 | A2 | 5/2007 |
| WO | 2008/144253 | A1 | 11/2008 |
| WO | 2009/134658 | A2 | 11/2009 |
| WO | 2010/006032 | A1 | 1/2010 |
| WO | 2010/023181 | A1 | 3/2010 |
| WO | 2011/104334 | A1 | 9/2011 |
| WO | 2011/104337 | A1 | 9/2011 |
| WO | 2011/104338 | A1 | 9/2011 |
| WO | 2011/104340 | A1 | 9/2011 |
| WO | 2011/149827 | A1 | 12/2011 |

OTHER PUBLICATIONS

Adesso et al., "Gemcitabine triggers a pro-survival response in pancreatic cancer cells through activation of the MNK2/eIF4E pathway," Oncogene, 2013, 31:2848-2857.

Amblard et al., "A new route to acyclic nucleosides via palladium-mediated allylic alkylation and cross-metathesis," Tetrahedron Letters, 2003, 44:9177-9180.

Blagden et al., The biological and therapeutic relevance of mRNA translation in cancer, Nature Reviews/Clinical Oncology, May 2011, 8:280-291.

Braendvang et al., "Efficient and regioselective N—I alkylation of 4-chloropyrazolo[3,4-d)pyrimidine," 2007, 48:3057-3059.

Buxade et al., "The Mnks: MAP kinase-interacting kinases (MAP kinase signal-integrating kinases)," Frontier in Bioscience, May 1, 2008, 5359-5374.

Chrestensen et al., "Loss of MNK function sensitizes fibroblasts to serum-withdrawal induced apoptosis," Genes to Cells, 2007, 12:113-1140.

Chrestensen et al., "MNK1 and MNK2 Regulation in HER2-overexpressing Breast Cancer Lines," Journal of Biological Chemistry, Feb. 16, 2007, 282(7):4243-4252.

Jauch et al., "Crystal Structures of the Mnk2 Kinase Domain Reveal an Inhibitory Conformation and a Zinc Binding Site," Structure, Oct. 2005, 13:1559-1568.

Jauch et al., "Mitogen-activated protein kinases interacting kinases are autoinhibited by a reprogrammed activation segment," The EMBO Journal, 2006, 25:4020-4032.

Konicek et al., "Therapeutic Inhibition of MAP Kinase Interacting Kinase Blocks Eukaryotic Initiation Factor 4E Phosphorylation and Suppresses Outgrowth of Experimental Lung Metastases," American Association for Cancer Research, Oct. 13, 2011, 1849-1857.

Konicek et al., "Targeting the eIF4F translation initiation complex for cancer therapy," Cell Cycle, Aug. 15, 2008, 7 (16):2466-2471.

Seela et al., "7-Functionalized 7-deazapurine β-D and β-L-ribonucleosides related to tubercidin and 7-deazainosine: glycosylation of pyrrolo[2,3-d]pyrimidines with 1-0-acetyl-2,3,5-tri-O-benzoyl-β-D or β-L-ribofuranose," Tetrahedron, 2007, 63:9850-9861.

Shi et al., "MNK kinases facilitate c-myc IRES activity in rapamycin-treated multiple myeloma cells," Oncogene, 2013, 32:190-197.

Sizun et al., "Synthesis of the first example of a nucleoside analogue bearing a 5'-deoxy-β-D-allo-septanose as a seven-membered ring sugar moiety," Carbohydrate Research, 2009, 344:448-453.

Ueda et al. "Mnk2 and Mnk1 Are Essential for Constitutive and Inducible Phosphorylation of Eukaryotic Initiation Factor 4E but Not for Cell Growth or Development," Molecular and Cellular Biology, Aug. 2004, 24(15):6539-6549.

Wendel et al., "Dissecting eIF4E action in tumorigenesis," Genes & Development, 2007, 21:3232-3237.

Yoshizawa et al., "Overexpression of Phospho-eIF4E Is Associated with Survival through AKT Pathway in Non-Small Cell Lung Cancer," Clinical Cancer Research, Jan. 1, 2010, 16(1):240-248.

U.S. Appl. No. 14/403,151, filed Nov. 21, 2014, pub as US2015-0133425 on May 14, 2015.

U.S. Appl. No. 14/429,927, filed Mar. 20, 2015, pub as US2015-0239891 on Aug. 27, 2015.

U.S. Appl. No. 14/431,656, filed Mar. 26, 2015, pub as US2015-0252047 on Sep. 10, 2015.

U.S. Appl. No. 14/431,674, filed Mar. 26, 2015, pub as US2015-0218173 on Aug. 6, 2015.

* cited by examiner

SUBSTITUTED BENZOTHIENOPYRIMIDINES

The present invention relates to substituted benzothienopyrimidine compounds of general formula I as described and defined herein, to methods of preparing said compounds, to intermediate compounds useful for preparing said compounds, to pharmaceutical compositions and combinations comprising said compounds and to the use of said compounds for manufacturing a pharmaceutical composition for the treatment or prophylaxis of a disease, in particular of a hyperproliferative and/or angiogenesis disorder, as a sole agent or in combination with other active ingredients.

BACKGROUND OF THE INVENTION

The present invention relates to chemical compounds that inhibit MKNK1 kinase (also known as MAP Kinase interacting Kinase, Mnk1) and/or MKNK2 kinase (also known as MAP Kinase interacting Kinase, Mnk2). Human MKNKs comprise a group of four proteins encoded by two genes (Gene symbols: MKNK1 and MKNK2) by alternative splicing. The b-forms lack a MAP kinase-binding domain situated at the C-terminus. The catalytic domains of the MKNK1 and MKNK2 are very similar and contain a unique DFD (Asp-Phe-Asp) motif in subdomain VII, which usually is DFG (Asp-Phe-Gly) in other protein kinases and suggested to alter ATP binding [Jauch et al., Structure 13, 1559-1568, 2005 and Jauch et al., EMBO J25, 4020-4032, 2006]. MKNK1a binds to and is activated by ERK and p38 MAP Kinases, but not by JNK1. MKNK2a binds to and is activated only by ERK. MKNK1b has low activity under all conditions and MKNK2b has a basal activity independent of ERK or p38 MAP Kinase. [Buxade M et al., Frontiers in Bioscience 5359-5374, May 1, 2008]

MKNKs have been shown to phosphorylate eukaryotic initiation factor 4E (eIF4E), heterogeneous nuclear RNA-binding protein A1 (hnRNP A1), polypyrimidine-tract binding protein-associated splicing factor (PSF), cytoplasmic phospholipase A2 (cPLA2) and Sprouty 2 (hSPRY2) [Buxade M et al., Frontiers in Bioscience 5359-5374, May 1, 2008].

eIF4E is an oncogene that is amplified in many cancers and is phosphorylated exclusively by MKNKs proteins as shown by KO-mouse studies [Konicek et al., Cell Cycle 7:16, 2466-2471, 2008; Ueda et al., Mol Cell Biol 24, 6539-6549, 2004]. eIF4E has a pivotal role in enabling the translation of cellular mRNAs. eIF4E binds the 7-methylguanosine cap at the 5' end of cellular mRNAs and delivers them to the ribosome as part of the eIF4F complex, also containing eIF4G and eIF4A. Though all capped mRNAs require eIF4E for translation, a pool of mRNAs is exceptionally dependent on elevated eIF4E activity for translation. These so-called "weak mRNAs" are usually less efficiently translated due to their long and complex 5' UTR region and they encode proteins that play significant roles in all aspects of malignancy including VEGF, FGF-2, c-Myc, cyclin D1, survivin, BCL-2, MCL-1, MMP-9, heparanase, etc. Expression and function of eIF4E is elevated in multiple human cancers and directly related to disease progression [Konicek et al., Cell Cycle 7:16, 2466-2471, 2008].

MKNK1 and MKNK2 are the only kinases known to phosphorylate eIF4E at Ser209. Overall translation rates are not affected by eIF4E phosphorylation, but it has been suggested that eIF4E phosphorylation contributes to polysome formation (i.e. multiple ribosome on a single mRNA) that ultimately enables more efficient translation of "weak mRNAs" [Buxade M et al., Frontiers in Bioscience 5359-5374, May 1, 2008]. Alternatively, phosphorylation of eIF4E by MKNK proteins might facilitate eIF4E release from the 5' cap so that the 48S complex can move along the "weak mRNA" in order to locate the start codon [Blagden S P and Willis A E, Nat Rev Clin Oncol. 8(5):280-91, 2011]. Accordingly, increased eIF4E phosphorylation predicts poor prognosis in non-small cell lung cancer patients [Yoshizawa et al., Clin Cancer Res. 16(1):240-8, 2010]. Further data point to a functional role of MKNK1 in carcinogenesis, as overexpression of constitutively active MKNK1, but not of kinase-dead MKNK1, in mouse embryo fibroblasts accelerates tumor formation [Chrestensen C. A. et al., Genes Cells 12, 1133-1140, 2007]. Moreover, increased phosphorylation and activity of MKNK proteins correlate with overexpression of HER2 in breast cancer [Chrestensen, C. A. et al., J. Biol. Chem. 282, 4243-4252, 2007]. Constitutively active, but not kinase-dead, MKNK1 also accelerated tumor growth in a model using Eμ-Myc transgenic hematopoietic stem cells to produce tumors in mice. Comparable results were achieved, when an eIF4E carrying a S209D mutation was analyzed. The S209D mutation mimicks a phosphorylation at the MKNK1 phosphorylation site. In contrast a non-phosphorylatable form of eIF4E attenuated tumor growth [Wendel H G, et al., Genes Dev. 21(24):3232-7, 2007]. A selective MKNK inhibitor that blocks eIF4E phosphorylation induces apoptosis and suppresses proliferation and soft agar growth of cancer cells in vitro. This inhibitor also suppresses outgrowth of experimental B16 melanoma pulmonary metastases and growth of subcutaneous HCT116 colon carcinoma xenograft tumors without affecting body weight [Konicek et al., Cancer Res. 71(5):1849-57, 2011]. In summary, eIF4E phosphorylation through MKNK protein activity can promote cellular proliferation and survival and is critical for malignant transformation. Inhibition of MKNK activity may provide a tractable cancer therapeutic approach.

Substituted thienopyrimidine compounds have been disclosed in prior art for the treatment or prophylaxis of different diseases:

WO 2010/006032 A1 (Duquesne University of the Holy Spirit) addresses tricyclic compounds as antimitotic agents. According to the general formula of claim 1, the tricycles inter alia comprise 5,6,7,8-tetrahydrobenzo[1]thieno[2,3-d]pyrimidines that may carry substituents at the carbocycle and one aromatic or heteroaromatic moiety at an optional 4-amino group. Furthermore, they may be unsubstituted at position 2 in the pyrimidine ring. However, the examples provided clearly differ from the compounds of the present invention. While the vast majority contains the C6 carbocycle completely unsaturated as aromatic ring, only two examples show a tetrahydrobenzo substructure in combination with a 4-amino group and in both cases the latter is bisubstituted by a phenyl and a methyl group. Furthermore, the specified compounds are with no exception pyrimidin-2-amines or 2-methyl-pyrimidines.

JP2007084494 (Oncorex Inc.) relates to PIM-1 inhibitors. One claim comprises 5,6,7,8-tetrahydrobenzo[1]thieno[2,3-d]pyrimidin-4-amines that can be monosubstituted at the amino group by optionally substituted phenyl. However, the optional substituents of phenyl are restricted to hydroxy, alkoxy or alkenyloxy. The tricyclic core does not show further substitutions. The only example of a direct substitution at the 4-amino group by phenyl is compound VII-2 with meta-methoxyphenyl.

WO 2002/088138 A1 (Bayer Pharmaceuticals Corporation) relates to PDE7b inhibitors and comprises 5,6,7,8-tetrahydrobenzo[1]thieno[2,3-d]pyrimidin-4-amines where the carbocycle and the 4-amino group may be optionally substituted by a wide range of substituents. The respective oxa, thia or aza analoga at position 7 with no further substituents at that ring are also claimed, the sulphur may be oxidized to sulphone and the nitrogen can be substituted. However, pyrid-4-yl in the 5,6,7,8-tetrahydrobenzo series and 3,4-dichlorophenyl and indazol-5-yl in the 6,9-dihydro-7H-pyrano series are the only examples with direct aromatic substitution at the 4-amino group.

WO 2005/010008 A1 (Bayer Pharmaceuticals Corporation) discloses 5,6,7,8-tetrahydrobenzo[1]thieno[2,3-d]pyrimidin-4-amines as proliferation inhibitors of A431 and BT474 cells which are model cell lines used in biomedical research. More specifically, A431 and BT474 cells are used in studies of the cell cycle and cancer-associated cell signalling pathways since they express abnormally high levels of the epidermal growth factor receptor (EGFR) and HER2, respectively. Substitution at the 4-amino group is limited to mono-substitution by either optionally substituted phenyl or optionally substituted indazolyl. The carbocycle may be substituted one or two times at position 7 by optionally substituted alkyl or alkenyl, by substituted carbonyl, hydroxy, optionally substituted amino or may be linked to the nitrogen of one or two saturated six membered rings optionally bearing a second heteroatom. Regarding the aromatic substituents at the 4-amino group, disclosed examples cover phenyl with a broad range of substituents and some indazol-5-yls but all are substituted at the nitrogen at position 1. Furthermore, all examples show an alkyl group in position 7 that is terminally further substituted by an amino group or hydroxyl group or in case of synthetic intermediates also by an ester function. Furthermore, as shown hereinafter, the compounds disclosed in WO 2005/010008 A1 are potent EGFR inhibitors but less effective MKNK inhibitors whereas the compounds of the present invention are potent MKNK inhibitors and less effective EGFR inhibitors.

WO 2009/134658 (National Health Research Institutes) relates to inhibitors of Aurora kinase. The patent application generically covers tricyclic thieno[2,3-d]pyrimidin-4-amines with the third ring fused to the thiophene subunit. However, an optional aryl or heteroaryl substituent at the 4-amino group must carry a side chain involving a carbonyl, thiocarbonyl or iminomethylene group. The vast majority of more than 250 examples is formed by bicyclic 6,7-dihydrofuro[3,2-d]pyrimidin-4-amines that show in 4 cases a direct aromatic substitution at the 4-amino group but additionally substitution by two phenyl groups at the dihydrofuro subunit. None of the very few examples for tricyclic compounds shows direct substitution by an aromatic moiety at the 4-amino group.

WO 2006/136402 A1 and WO 2007/059905 A2 (Develogen AG) disclose thienopyrimidin-4-amines and their use for the prophylaxis and/or treatment of diseases which can be influenced by the inhibition of the kinase activity of Mnk1 and/or Mnk2. The 4-amino-group is substituted by a substituted phenyl group. The WO publications do not disclose any biological data.

WO 2010/023181 A1, WO 2011/104334 A1, WO 2011/104337 A1, WO 2011/104338 A1 and WO 2011/104340 A1 (Boehringer Ingelheim) relate to thienopyrimidin-4-amines for the prophylaxis and/or treatment of diseases which can be influenced by the inhibition of the kinase activity of Mnk1 and/or Mnk2. In case of the disclosed thienopyrimidin-4-amines there is no tetrahydrobenzo ring fused to the thienopyrimidine core. Additionally, the 4-amino group does not carry an indazol-5-yl substituent. In case of the compounds disclosed in WO 2010/023181 A1 the $IC_{50}$ values vary between 0.035 μM and 0.68 μM with respect Mnk1, and between 0.006 μM and 0.56 μM with respect to Mnk2. In case of the compounds disclosed in WO 2011/104334 A1 the $IC_{50}$ values vary between 1 nM and 9700 nM with respect to Mnk2. In case of the compounds disclosed in WO 2011/104337 A1 the $IC_{50}$ values vary between 2 nM and 8417 nM with respect to Mnk2. In case of the compounds disclosed in WO 2011/104338 A1 the $IC_{50}$ values vary between 8 nM and 58 nM with respect to Mnk2. In case of the compounds disclosed in WO 2011/104340 A1 the $IC_{50}$ values vary between 3 nM and 5403 nM with respect to Mnk2. All WO publications contain the statement that the compounds described therein show improved solubility, are highly selective and show improved metabolic stability when compared to the compounds disclosed in WO 2006/136402 A1 and WO 2007/059905 A2 (Develogen AG, see above). However, besides the $IC_{50}$ values discussed in this paragraph, there are no more data proving this statement.

The state of the art described above does not describe the specific substituted thienopyrimidine compounds of general formula (I) of the present invention as defined herein or a stereoisomer, a tautomer, an N-oxide, a hydrate, a solvate, or a salt thereof, or a mixture of same, as described and defined herein, and as hereinafter referred to as "compounds of the present invention", or their pharmacological activity.

It has now been found, and this constitutes the basis of the present invention, that said compounds of the present invention have surprising and advantageous properties.

In particular, said compounds of the present invention have surprisingly been found to effectively inhibit MKNK1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK1 kinase, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

SUMMARY OF THE INVENTION

The present invention covers compounds of general formula I:

I

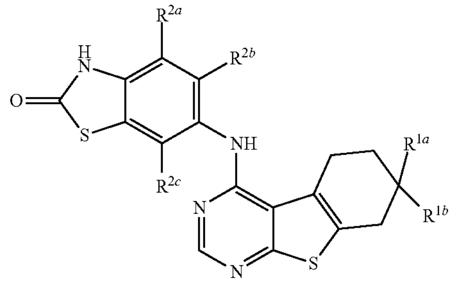

in which:

$R^{1a}$ represents a hydrogen atom or a group selected from: —O—$C_1$-$C_6$-alkyl, —$(CH_2)_r$—$R^8$, —$(CH_2)_r$—$NR^3R^4$, —$(CH_2)_r$—$N(R^4)C(=O)R^3$, $-(CH_2)_r-N(R^4)S(=O)_2R^3$, $-(CH_2)_r-C(=O)OR^3$, $-(CH_2)_r-C(=O)NR^3R^4$, $-(CH_2)_r-N(R^4)C(=O)OR^3$, $-(CH_2)_r-N(R^4)C(=O)N(H)R^3$, $R^{1b}$ represents a hydrogen atom or a group selected from: $C_1$-$C_6$-alkyl-, $-(CH_2)_r-O-(C_1$-$C_6$-alkyl); or $R^{1a}$ and $R^{1b}$ together form an oxygen atom or a $-O-(C_2$-$C_6$-alkylene)-O— group;

$R^{2a}$ represents a hydrogen atom or a halogen atom or a group selected from: $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, $-N(H)R^5$, $-NR^5R^4$;

$R^{2b}$ represents a hydrogen atom or a halogen atom or a group selected from: $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, $-N(H)R^5$, $-NR^5R^4$, $-N(H)C(=O)R^5$, $-N(R^4)C(=O)R^5$, $-N(H)C(=O)NR^5R^4$, $-N(R^4)C(=O)NR^5R^4$, $-C(=O)N(H)R^5$, $-C(=O)NR^5R^4$;

$R^{2c}$ represents a hydrogen atom or a halogen atom or a group selected from: $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, $-N(H)R^5$, $-NR^5R^4$;

$R^3$ represents a hydrogen atom or a group selected from: $C_1$-$C_6$-alkyl-, $C_2$-$C_6$-alkynyl-, $C_3$-$C_6$-cycloalkyl-, $-(CH_2)_q-(C_3$-$C_6$-cycloalkyl), $-(CH_2)_q-O-(C_3$-$C_6$-cycloalkyl), 3- to 10-membered heterocycloalkyl, $-(CH_2)_q$-(3- to 10-membered heterocycloalkyl), $-(CH_2)_q$—O-(3- to 10-membered heterocycloalkyl), 4- to 10-membered heterocycloalkenyl, $-(CH_2)_q$-(4- to 10-membered heterocycloalkenyl), $-(CH_2)_q$—O-(4- to 10-membered heterocycloalkenyl), aryl, $-(CH_2)_q$-aryl, $-(CH_2)_q$—O-aryl, heteroaryl, $-(CH_2)_q$-heteroaryl, $-(CH_2)_q$—O-heteroaryl, -(3- to 10-membered heterocycloalkyl)-$(CH_2)_q$-(3- to 10-membered heterocycloalkyl), -(3- to 10-membered heterocycloalkyl)-$(CH_2)_q$-aryl, -(3- to 10-membered heterocycloalkyl)-$(CH_2)_q$-heteroaryl, said group being optionally substituted, identically or differently, with 1, 2, 3, 4 or 5 $R^8$ groups; or when 2 $R^8$ groups are present ortho to each other on an aryl- or heteroaryl-ring, said 2 $R^8$ groups together form a bridge: $*O(CH_2)_pO*$, $*NH(C(=O))NH*$, wherein * represent the point of attachment to said aryl- or heteroaryl-ring;

$R^4$ represents a hydrogen atom or a group selected from: $C_1$-$C_6$-alkyl-, $-(CH_2)_q$-aryl, $C_1$-$C_6$-alkoxy-$C_1$-$C_6$-alkyl-; or $NR^3R^4$ together represent a 3- to 10-membered heterocycloalkyl group, a benzo fused 3- to 10-membered heterocycloalkyl group or a 4- to 10-membered heterocycloalkenyl group; said 3- to 10-membered heterocycloalkyl or 4- to 10-membered heterocycloalkenyl group being optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl-, $-(CH_2)_q$-aryl, $-(CH_2)_q$-heteroaryl, $-N(R^4)C(=O)R^5$, $-NR^5R^4$ or $-(CH_2)_r-C(=O)NR^6R^7$;

$R^5$ represents a hydrogen atom, a $C_1$-$C_6$-alkyl- or a $C_3$-$C_6$-cycloalkyl-group;

$R^6$ represents a hydrogen atom, a $C_1$-$C_6$-alkyl- or a $C_3$-$C_6$-cycloalkyl-group;

$R^7$ represents a hydrogen atom, a $C_1$-$C_6$-alkyl- or a $C_3$-$C_6$-cycloalkyl-group; or $NR^6R^7$ together represent a 3- to 10-membered heterocycloalkyl group;

$R^8$ represents halo-, azido-, hydroxy-, oxo-(O═), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5-O-$, $-C(=O)R^5$, $-C(=O)O-R^5$, $-OC(=O)-R^5$, $-N(H)C(=O)R^5$, $-N(R^4)C(=O)R^5$, $-N(H)C(=O)NR^5R^4$, $-N(R^4)C(=O)NR^5R^4$, $-N(R^4)C(=O)OR^5$, $-N(H)R^5$, $-NR^5R^4$, $-C(=O)N(H)R^5$, $-C(=O)NR^5R^4$, $R^4-S-$, $R^4-S(=O)-$, $R^4-S(=O)_2-$, $-N(H)S(=O)R^4$, $-N(R^4)S(=O)R^4$, $-S(=O)N(H)R^5$, $-S(=O)NR^5R^4$, $-N(H)S(=O)_2R^4$, $-N(R^4)S(=O)_2R^4$, $-S(=O)_2N(H)R^5$, $-S(=O)_2NR^5R^4$, $-S(=O)(=NR^5)R^4$, $-S(=O)(=NR^4)R^5$ or $-N=S(=O)(R^5)R^4$;

p represents an integer of 1 or 2;

q represents an integer of 1, 2 or 3;

r represents an integer of 0, 1 or 2;

or a tautomer, an N-oxide, a hydrate, a solvate, or a salt thereof, or a mixture of same.

The present invention further relates to methods of preparing compounds of general formula I, to pharmaceutical compositions and combinations comprising said compounds, to the use of said compounds for manufacturing a pharmaceutical composition for the treatment or prophylaxis of a disease, as well as to intermediate compounds useful in the preparation of said compounds.

DETAILED DESCRIPTION OF THE INVENTION

The terms as mentioned in the present text have preferably the following meanings:

The term "halogen atom", "halo-" or "Hal-" is to be understood as meaning a fluorine, chlorine, bromine or iodine atom, preferably a fluorine or a chlorine atom.

The term "$C_1$-$C_6$-alkyl" is to be understood as preferably meaning a linear or branched, saturated, monovalent hydrocarbon group having 1, 2, 3, 4, 5 or 6 carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, or 1,2-dimethylbutyl group, or an isomer thereof. Particularly, said group has 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2 or 3 carbon atoms ("$C_1$-$C_3$-alkyl"), e.g. a methyl, ethyl, n-propyl- or iso-propyl group.

The term "halo-$C_1$-$C_6$-alkyl" is to be understood as preferably meaning a linear or branched, saturated, monovalent hydrocarbon group in which the term "$C_1$-$C_6$-alkyl" is defined supra, and in which one or more hydrogen atoms is replaced by a halogen atom, in identically or differently, i.e. one halogen atom being independent from another. Particularly, said halogen atom is F. Said halo-$C_1$-$C_6$-alkyl group is, for example, —$CF_3$, —$CHF_2$, —$CH_2F$, —$CF_2CF_3$, or —$CH_2CF_3$.

The term "$C_1$-$C_6$-alkoxy" is to be understood as preferably meaning a linear or branched, saturated, monovalent, hydrocarbon group of formula —O—($C_1$-$C_6$-alkyl), in which the term "$C_1$-$C_6$-alkyl" is defined supra, e.g. a methoxy, ethoxy, n-propoxy, iso-propoxy, n-butoxy, iso-butoxy, tert-butoxy, sec-butoxy, pentoxy, iso-pentoxy, or n-hexoxy group, or an isomer thereof.

The term "halo-$C_1$-$C_6$-alkoxy" is to be understood as preferably meaning a linear or branched, saturated, monovalent $C_1$-$C_6$-alkoxy group, as defined supra, in which one or more of the hydrogen atoms is replaced, in identically or differently, by a halogen atom. Particularly, said halogen atom is F. Said halo-$C_1$-$C_6$-alkoxy group is, for example, —$OCF_3$, —$OCHF_2$, —$OCH_2F$, —$OCF_2CF_3$, or —$OCH_2CF_3$.

The term "$C_1$-$C_6$-alkoxy-$C_1$-$C_6$-alkyl" is to be understood as preferably meaning a linear or branched, saturated, monovalent $C_1$-$C_6$-alkyl group, as defined supra, in which one or more of the hydrogen atoms is replaced, in identically or differently, by a $C_1$-$C_6$-alkoxy group, as defined supra, e.g. methoxyalkyl, ethoxyalkyl, propyloxyalkyl, iso-propoxyalkyl, butoxyalkyl, iso-butoxyalkyl, tert-butoxyalkyl, sec-butoxyalkyl, pentyloxyalkyl, iso-pentyloxyalkyl, hexyloxyalkyl group, or an isomer thereof.

The term "halo-$C_1$-$C_6$-alkoxy-$C_1$-$C_6$-alkyl" is to be understood as preferably meaning a linear or branched, saturated, monovalent $C_1$-$C_6$-alkoxy-$C_1$-$C_6$-alkyl group, as defined supra, in which one or more of the hydrogen atoms is replaced, in identically or differently, by a halogen atom. Particularly, said halogen atom is F. Said halo-$C_1$-$C_6$-alkoxy-$C_1$-$C_6$-alkyl group is, for example, —$CH_2CH_2OCF_3$, —$CH_2CH_2OCHF_2$, —$CH_2CH_2OCH_2F$, —$CH_2CH_2OCF_2CF_3$, or —$CH_2CH_2OCH_2CF_3$.

The term "$C_2$-$C_6$-alkenyl" is to be understood as preferably meaning a linear or branched, monovalent hydrocarbon group, which contains one or more double bonds, and which has 2, 3, 4, 5 or 6 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, iso-propenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, (E)-3-methylpent-3-enyl, (Z)-3-methylpent-3-enyl, (E)-2-methylpent-3-enyl, (Z)-2-methylpent-3-enyl, (E)-1-methylpent-3-enyl, (Z)-1-methylpent-3-enyl, (E)-4-methylpent-2-enyl, (Z)-4-methylpent-2-enyl, (E)-3-methylpent-2-enyl, (Z)-3-methylpent-2-enyl, (E)-2-methylpent-2-enyl, (Z)-2-methylpent-2-enyl, (E)-1-methylpent-2-enyl, (Z)-1-methylpent-2-enyl, (E)-4-methylpent-1-enyl, (Z)-4-methylpent-1-enyl, (E)-3-methylpent-1-enyl, (Z)-3-methylpent-1-enyl, (E)-2-methylpent-1-enyl, (Z)-2-methylpent-1-enyl, (E)-1-methylpent-1-enyl, (Z)-1-methylpent-1-enyl, 3-ethylbut-3-enyl, 2-ethylbut-3-enyl, 1-ethylbut-3-enyl, (E)-3-ethylbut-2-enyl, (Z)-3-ethylbut-2-enyl, (E)-2-ethylbut-2-enyl, (Z)-2-ethylbut-2-enyl, (E)-1-ethylbut-2-enyl, (Z)-1-ethylbut-2-enyl, (E)-3-ethylbut-1-enyl, (Z)-3-ethylbut-1-enyl, 2-ethylbut-1-enyl, (E)-1-ethylbut-1-enyl, (Z)-1-ethylbut-1-enyl, 2-propylprop-2-enyl, 1-propylprop-2-enyl, 2-isopropylprop-2-enyl, 1-isopropylprop-2-enyl, (E)-2-propylprop-1-enyl, (Z)-2-propylprop-1-enyl, (E)-1-propylprop-1-enyl, (Z)-1-propylprop-1-enyl, (E)-2-isopropylprop-1-enyl, (Z)-2-isopropylprop-1-enyl, (E)-1-isopropylprop-1-enyl, (Z)-1-isopropylprop-1-enyl, (E)-3,3-dimethylprop-1-enyl, (Z)-3,3-dimethylprop-1-enyl, 1-(1,1-dimethylethyl)ethenyl, buta-1,3-dienyl, penta-1,4-dienyl, hexa-1,5-dienyl, or methylhexadienyl group. Particularly, said group is vinyl or allyl.

The term "$C_2$-$C_6$-alkynyl" is to be understood as preferably meaning a linear or branched, monovalent hydrocarbon group which contains one or more triple bonds, and which contains 2, 3, 4, 5 or 6 carbon atoms, particularly 2 or 3 carbon atoms ("$C_2$-$C_3$-alkynyl"). Said $C_2$-$C_6$-alkynyl group is, for example, ethynyl, prop-1-ynyl, prop-2-ynyl, but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl, or 3,3-dimethylbut-1-ynyl group. Particularly, said alkynyl group is ethynyl, prop-1-ynyl, or prop-2-ynyl.

The term "$C_3$-$C_7$-cycloalkyl" is to be understood as meaning a saturated, monovalent, monocyclic hydrocarbon ring which contains 3, 4, 5, 6 or 7 carbon atoms. Said $C_3$-$C_7$-cycloalkyl group is for example a cyclopropyl, cyclobutyl, cyclopentyl, cyclohexyl or cycloheptyl ring. Particularly, said ring contains 3, 4, 5 or 6 carbon atoms ("$C_3$-$C_6$-cycloalkyl").

The term "$C_4$-$C_7$-cycloalkenyl" is to be understood as preferably meaning a monovalent, monocyclic hydrocarbon ring which contains 4, 5, 6 or 7 carbon atoms and one or two double bonds, in conjugation or not, as the size of said cycloalkenyl ring allows. Said $C_4$-$C_7$-cycloalkenyl group is for example a cyclobutenyl, cyclopentenyl, or cyclohexenyl group.

The term "3- to 10-membered heterocycloalkyl", is to be understood as meaning a saturated, monovalent, mono- or bicyclic hydrocarbon ring which contains 2, 3, 4, 5, 6, 7, 8 or 9 carbon atoms, and one or more heteroatom-containing groups selected from C(═O), O, S, S(═O), $S(═O)_2$, $NR^a$, in which $R^a$ represents a hydrogen atom, or a $C_1$-$C_6$-alkyl-group; it being possible for said heterocycloalkyl group to be attached to the rest of the molecule via any one of the carbon atoms or, if present, the nitrogen atom.

Particularly, said 3- to 10-membered heterocycloalkyl can contain 2, 3, 4, or 5 carbon atoms, and one or more of the above-mentioned heteroatom-containing groups (a "3- to 6-membered heterocycloalkyl"), more particularly said heterocycloalkyl can contain 4 or 5 carbon atoms, and one or more of the above-mentioned heteroatom-containing groups (a "5- to 6-membered heterocycloalkyl").

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example.

Examples of bicyclic 3- to 10-membered heterocycloalkyl groups are:

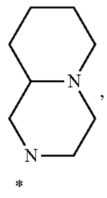, 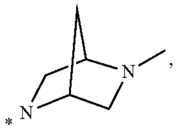, 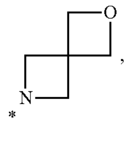, 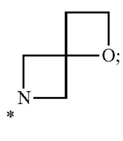;

wherein * represents the point of attachment of sad groups to the rest of the molecule.

The term "benzo fused 3- to 10-membered heterocycloalkyl", is to be understood as meaning a 3- to 10-membered heterocycloalkyl group as defined above, onto which a benzene ring is fused. An example of a benzo fused 3- to 10-membered heterocycloalkyl group is

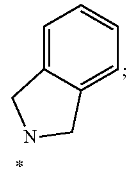;

wherein * represents the point of attachment to the rest of the molecule.

The term "4- to 10-membered heterocycloalkenyl", is to be understood as meaning an unsaturated, monovalent, mono- or bicyclic hydrocarbon ring which contains 3, 4, 5, 6, 7, 8 or 9 carbon atoms, and one or more heteroatom-containing groups selected from C(═O), O, S, S(═O), $S(=O)_2$, NRa, in which Ra represents a hydrogen atom or a $C_1$-$C_6$-alkyl-group; it being possible for said heterocycloalkenyl group to be attached to the rest of the molecule via any one of the carbon atoms or, if present, the nitrogen atom. Examples of said heterocycloalkenyl may contain one or more double bonds, e.g. 4H-pyranyl, 2H-pyranyl, 3H-diazirinyl, 2,5-dihydro-1H-pyrrolyl, [1,3]dioxolyl, 4H-[1,3,4]thiadiazinyl, 2,5-dihydrofuranyl, 2,3-dihydrofuranyl, 2,5-dihydrothiophenyl, 2,3-dihydrothiophenyl, 4,5-dihydrooxazolyl, or 4H-[1,4]thiazinyl group.

The term "aryl" is to be understood as preferably meaning a monovalent, aromatic or partially aromatic, mono-, or bi- or tricyclic hydrocarbon ring having 6, 7, 8, 9, 10, 11, 12, 13 or 14 carbon atoms (a "$C_6$-$C_{14}$-aryl" group), particularly a ring having 6 carbon atoms (a "$C_6$-aryl" group), e.g. a phenyl group; or a ring having 9 carbon atoms (a "$C_9$-aryl" group), e.g. an indanyl or indenyl group, or a ring having 10 carbon atoms (a "$C_{10}$-aryl" group), e.g. a tetralinyl, dihydronaphthyl, or naphthyl group, or a biphenyl group (a "$C_{12}$-aryl" group), or a ring having 13 carbon atoms, (a "$C_{13}$-aryl" group), e.g. a fluorenyl group, or a ring having 14 carbon atoms, (a "$C_{14}$-aryl" group), e.g. an anthracenyl group. Preferably, the aryl group is a phenyl group.

The term "heteroaryl" is understood as preferably meaning a monovalent, monocyclic-, bicyclic- or tricyclic aromatic ring system having 5, 6, 7, 8, 9, 10, 11, 12, 13 or 14 ring atoms (a "5- to 14-membered heteroaryl" group), particularly 5 or 6 or 9 or 10 atoms, and which contains at least one heteroatom which may be identical or different, said heteroatom being such as oxygen, nitrogen or sulfur, and in addition in each case can be benzocondensed. Particularly, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, for example, benzofuranyl, benzothienyl, benzoxazolyl, benzisoxazolyl, benzimidazolyl, benzotriazolyl, indazolyl, indolyl, isoindolyl, etc.; or pyridinyl, pyridazinyl, pyrimidinyl, pyrazinyl, triazinyl, etc., and benzo derivatives thereof, such as, for example, quinolinyl, quinazolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

In general, and unless otherwise mentioned, the heteroarylic or heteroarylenic radicals include all the possible isomeric forms thereof, e.g. the positional isomers thereof. Thus, for some illustrative non-restricting example, the term pyridyl includes pyridin-2-yl, pyridin-3-yl, and pyridin-4-yl; or the term thienyl includes thien-2-yl and thien-3-yl. Preferably, the heteroaryl group is a pyridinyl group.

The term "$C_1$-$C_6$", as used throughout this text, e.g. in the context of the definition of "$C_1$-$C_6$-alkyl", "$C_1$-$C_6$-haloalkyl", "$C_1$-$C_6$-alkoxy", or "$C_1$-$C_6$-haloalkoxy" is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$; particularly $C_1$-$C_2$, $C_1$-$C_3$, $C_1$-$C_4$, $C_1$-$C_5$, $C_1$-$C_6$; more particularly $C_1$-$C_4$; in the case of "$C_1$-$C_6$-haloalkyl" or "$C_1$-$C_6$-haloalkoxy" even more particularly $C_1$-$C_2$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; particularly $C_2$-$C_3$.

Further, as used herein, the term "$C_3$-$C_7$", as used throughout this text, e.g. in the context of the definition of "$C_3$-$C_7$-cycloalkyl", is to be understood as meaning a cycloalkyl group having a finite number of carbon atoms of 3 to 7, i.e. 3, 4, 5, 6 or 7 carbon atoms. It is to be understood further that said term "$C_3$-$C_7$" is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_7$; particularly $C_3$-$C_6$.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

The term "optionally substituted" means that the number of substituents can be zero. Unless otherwise indicated, optionally substituted groups may be substituted with as many optional substituents as can be accommodated by replacing a hydrogen atom with a non-hydrogen substituent on any available carbon or nitrogen atom. Commonly, the number of optional substituents (when present) ranges from 1 to 3.

Ring system substituent means a substituent attached to an aromatic or nonaromatic ring system which, for example, replaces an available hydrogen on the ring system.

As used herein, the term "one or more", e.g. in the definition of the substituents of the compounds of the general formulae of the present invention, is understood as meaning "one, two, three, four or five, particularly one, two, three or four, more particularly one, two or three, even more particularly one or two".

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^{2}H$ (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^{3}H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

The compounds of the present invention may contain sulphur atoms which are asymmetric, such as an asymmetric sulphoxide or sulphoximine group, of structure:

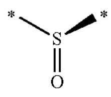

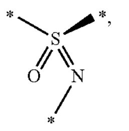

for example, in which * indicates atoms to which the rest of the molecule can be bound.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel O D and Chiracel O J among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, or (E)- or (Z)-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

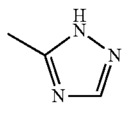

1H-tautomer

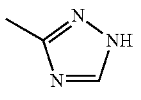

2H-tautomer

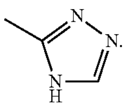

4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

Where the plural form of the word compounds, salts, polymorphs, hydrates, solvates and the like, is used herein, this is taken to mean also a single compound, salt, polymorph, isomer, hydrate, solvate or the like.

By "stable compound" or "stable structure" is meant a compound that is sufficiently robust to survive isolation to a useful degree of purity from a reaction mixture, and formulation into an efficacious therapeutic agent.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

Furthermore, the present invention includes all possible crystalline forms, or polymorphs, of the compounds of the present invention, either as single polymorphs, or as a mixture of more than one polymorphs, in any ratio.

In accordance with a first aspect, the present invention covers compounds of general formula I:

I

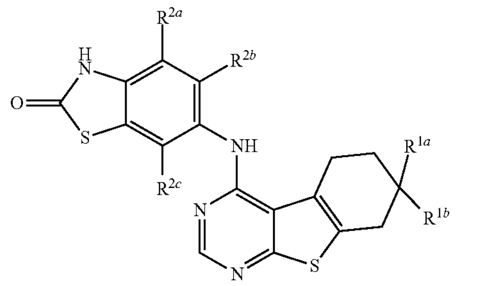

in which:

$R^{1a}$ represents a hydrogen atom or a group selected from:
 —O—$C_1$-$C_6$-alkyl, —$(CH_2)_r$—$R^8$, —$(CH_2)_r$—$NR^3R^4$, —$(CH_2)_r$—$N(R^4)C(=O)R^3$,
 —$(CH_2)_r$—$N(R^4)S(=O)_2R^3$, —$(CH_2)_r$—$C(=O)OR^3$, —$(CH_2)_r$—$C(=O)NR^3R^4$,
 —$(CH_2)_r$—$N(R^4)C(=O)OR^3$, —$(CH_2)_r$—$N(R^4)C(=O)N(H)R^3$, $R^{1b}$ represents a hydrogen atom or a group selected from:
 $C_1$-$C_6$-alkyl-, —$(CH_2)_r$—O—($C_1$-$C_6$-alkyl); or $R^{1a}$ and $R^{1b}$ together
 form an oxygen atom or a —O—($C_2$-$C_6$-alkylene)-O— group;

$R^{2a}$ represents a hydrogen atom or a halogen atom or a group selected from:
 $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —$N(H)R^5$, —$NR^5R^4$;

$R^{2b}$ represents a hydrogen atom or a halogen atom or a group selected from:
 $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —$N(H)R^5$, —$NR^5R^4$, —$N(H)C(=O)R^5$, —$N(R^4)C(=O)R^5$, —$N(H)C(=O)NR^5R^4$, —$N(R^4)C(=O)NR^5R^4$, —$C(=O)N(H)R^5$, —$C(=O)NR^5R^4$;

$R^{2c}$ represents a hydrogen atom or a halogen atom or a group selected from:
 $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —$N(H)R^5$, —$NR^5R^4$;

$R^3$ represents a hydrogen atom or a group selected from:
 $C_1$-$C_6$-alkyl-, $C_2$-$C_6$-alkynyl-, $C_3$-$C_6$-cycloalkyl-, —$(CH_2)_q$—($C_3$-$C_6$-cycloalkyl),
 —$(CH_2)_q$—O—($C_3$-$C_6$-cycloalkyl), 3- to 10-membered heterocycloalkyl,
 —$(CH_2)_q$-(3- to 10-membered heterocycloalkyl),
 —$(CH_2)_q$—O-(3- to 10-membered heterocycloalkyl),
 4- to 10-membered heterocycloalkenyl,
 —$(CH_2)_q$-(4- to 10-membered heterocycloalkenyl),
 —$(CH_2)_q$—O-(4- to 10-membered heterocycloalkenyl),
 aryl, —$(CH_2)_q$-aryl, —$(CH_2)_q$—O-aryl, heteroaryl, —$(CH_2)_q$-heteroaryl, —$(CH_2)_q$—O-heteroaryl,
 -(3- to 10-membered heterocycloalkyl)-$(CH_2)_q$-(3- to 10-membered heterocycloalkyl), -(3- to 10-membered heterocycloalkyl)-$(CH_2)_q$-aryl,
 -(3- to 10-membered heterocycloalkyl)-$(CH_2)_q$-heteroaryl,
 said group being optionally substituted, identically or differently, with 1, 2, 3, 4 or 5 $R^8$ groups; or
 when 2 $R^8$ groups are present ortho to each other on an aryl- or heteroaryl-ring, said 2 $R^8$ groups together form a bridge:
 *$O(CH_2)_pO$*, *NH(C(=O))NH*, wherein * represent the point of attachment to said aryl- or heteroaryl-ring;

$R^4$ represents a hydrogen atom or a group selected from:
 $C_1$-$C_6$-alkyl-, —$(CH_2)_q$-aryl, $C_1$-$C_6$-alkoxy-$C_1$-$C_6$-alkyl-; or $NR^3R^4$ together represent a 3- to 10-membered heterocycloalkyl group, a benzo fused 3- to 10-membered heterocycloalkyl group or a 4- to 10-membered heterocycloalkenyl group;
 said 3- to 10-membered heterocycloalkyl or 4- to 10-membered heterocycloalkenyl group being optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl-, —$(CH_2)_q$-aryl, —$(CH_2)_q$-heteroaryl, —$N(R^4)C(=O)R^5$, —$NR^5R^4$ or —$(CH_2)_r$—$C(=O)NR^6R^7$;

$R^5$ represents a hydrogen atom, a $C_1$-$C_6$-alkyl- or a $C_3$-$C_6$-cycloalkyl-group;

$R^6$ represents a hydrogen atom, a $C_1$-$C_6$-alkyl- or a $C_3$-$C_6$-cycloalkyl-group;

$R^7$ represents a hydrogen atom, a $C_1$-$C_6$-alkyl- or a $C_3$-$C_6$-cycloalkyl-group; or $NR^6R^7$ together represent a 3- to 10-membered heterocycloalkyl group;

$R^8$ represents halo-, azido-, hydroxy-, oxo-(O=), cyano-, nitro-, $C_1$-$C_6$-alkyl-,
 $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-,
halo-$C_1$-$C_6$-alkoxy-$C_1$-$C_6$-alkyl-, $R^5$—O—, —C(═O)$R^5$, —C(═O)O—$R^5$, —OC(═O)—$R^5$,
—N(H)C(═O)$R^5$, —N($R^4$)C(═O)$R^5$, —N(H)C(═O)N$R^5R^4$, —N($R^4$)C(═O)N$R^5R^4$,
—N($R^4$)C(═O)O$R^5$, —N(H)$R^5$, —N$R^5R^4$, —C(═O)N(H)$R^5$, —C(═O)N$R^5R^4$, $R^4$—S—,
$R^4$—S(═O)—, $R^4$—S(═O)$_2$—, —N(H)S(═O)$R^4$, —N($R^4$)S(═O)$R^4$, —S(═O)N(H)$R^5$,
—S(═O)N$R^5R^4$, —N(H)S(═O)$_2R^4$, —N($R^4$)S(═O)$_2R^4$, —S(═O)$_2$N(H)$R^5$, —S(═O)$_2$N$R^5R^4$,
—S(═O)(═N$R^5$)$R^4$, —S(═O)(═N$R^4$)$R^5$ or —N═S(═O)($R^5$)$R^4$;

p represents an integer of 1 or 2;
q represents an integer of 1, 2 or 3;
r represents an integer of 0, 1 or 2;
or a tautomer, an N-oxide, a hydrate, a solvate, or a salt thereof, or a mixture of same.

In a preferred embodiment, the invention relates to compounds of formula I, supra, wherein $R^{1a}$ represents a group selected from —C(═O)O—$R^3$, —C(═O)N(H)$R^3$, —C(═O)N$R^3R^4$.

In another preferred embodiment, the invention relates to compounds of formula I, supra, wherein $R^{1a}$ represents a —C(═O)O—$R^3$ group.

In another preferred embodiment, the invention relates to compounds of formula I, supra, wherein $R^{1a}$ represents a —C(═O)N(H)$R^3$ group.

In another preferred embodiment, the invention relates to compounds of formula I, supra, wherein $R^{1a}$ represents a —C(═O)N$R^3R^4$ group.

In another preferred embodiment, the invention relates to compounds of formula I, supra, wherein $R^{1a}$ represents a group selected from: —($CH_2$)$_r$—N($R^4$)C(═O)O$R^3$, —($CH_2$)$_r$—N($R^4$)C(═O)N(H)$R^3$.

In another preferred embodiment, the invention relates to compounds of formula I, supra, wherein $R^{1a}$ represents a group selected from: —($CH_2$)$_r$—C(═O)O$R^3$, —($CH_2$)$_r$—C(═O)N$R^3R^4$.

In another preferred embodiment, the invention relates to compounds of formula I, supra, wherein $R^{1a}$ represents a —($CH_2$)$_r$—N($R^4$)C(═O)$R^3$ group.

In another preferred embodiment, the invention relates to compounds of formula I, supra, wherein $R^{1b}$ represents a hydrogen atom.

In another preferred embodiment, the invention relates to compounds of formula Ia:

Ia

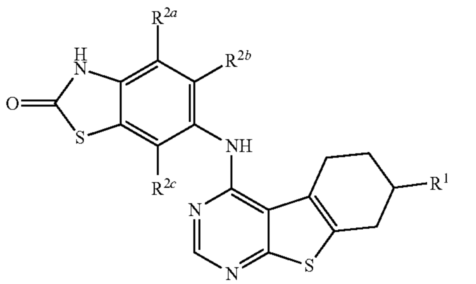

in which:
$R^{2a}$, $R^{2b}$, $R^{2c}$ are as defined for general formula I, supra; and
$R^1$ represents a group selected from: —O—$C_1$-$C_6$-alkyl, —($CH_2$)$_r$—$R^8$, —($CH_2$)$_r$—N$R^3R^4$, —($CH_2$)$_r$—N($R^4$)C(═O)$R^3$, —($CH_2$)$_r$—N($R^4$)S(═O)$_2R^3$, —($CH_2$)$_r$—C(═O)O$R^3$, —($CH_2$)$_r$—C(═O)N$R^3R^4$, —($CH_2$)$_r$—N($R^4$)C(═O)O$R^3$, —($CH_2$)$_r$—N($R^4$)C(═O)N(H)$R^3$.

In another preferred embodiment, the invention relates to compounds of formula Ia, supra, wherein $R^1$ represents a group selected from:
—($CH_2$)$_r$—N$R^3R^4$, —($CH_2$)$_r$—N($R^4$)C(═O)$R^3$, —($CH_2$)$_r$—N($R^4$)S(═O)$_2R^3$, ($CH_2$)$_r$—C(═O)N$R^3R^4$, —($CH_2$)$_r$—N($R^4$)C(═O)O$R^3$, —($CH_2$)$_r$—N($R^4$)C(═O)N(H)$R^3$.

In another preferred embodiment, the invention relates to compounds of formula Ia, supra, wherein $R^1$ represents a group selected from:
—C(═O)O—$R^3$, —C(═O)N(H)$R^3$, —C(═O)N$R^3R^4$.

In another preferred embodiment, the invention relates to compounds of formula Ia, supra, wherein $R^1$ represents a group selected from:
—C(═O)N(H)$R^3$, —C(═O)N$R^3R^4$.

In another preferred embodiment, the invention relates to compounds of formula I or Ia, supra, wherein $R^{2a}$ represents a hydrogen atom.

In another preferred embodiment, the invention relates to compounds of formula I or Ia, supra, wherein $R^{2b}$ represents a hydrogen atom or a halogen atom a group selected from $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —N(H)$R^5$, —N$R^5R^4$.

In another preferred embodiment, the invention relates to compounds of formula I or Ia, supra, wherein $R^{2b}$ represents a hydrogen atom.

In another preferred embodiment, the invention relates to compounds of formula I or Ia, supra, wherein $R^{2b}$ represents a group selected from halo-, $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —N(H)$R^5$, —N$R^5R^4$.

In another preferred embodiment, the invention relates to compounds of formula I or Ia, supra, wherein $R^{2b}$ represents a group selected from: $C_1$-$C_3$-alkoxy-, halo-.

In another preferred embodiment, the invention relates to compounds of formula I or Ia, supra, wherein $R^{2b}$ represents a halogen atom.

In another preferred embodiment, the invention relates to compounds of formula I or Ia, supra, wherein $R^{2c}$ represents a hydrogen atom.

In another preferred embodiment, the invention relates to compounds of formula I or Ia, supra, wherein each of $R^{2a}$ and $R^{2c}$ represents a hydrogen atom.

In another preferred embodiment, the invention relates to compounds of formula I or Ia, supra, wherein each of $R^{2a}$ and $R^{2c}$ represents a hydrogen atom and $R^{2b}$ represents a hydrogen atom or a $C_1$-$C_3$-alkoxy-group.

In another preferred embodiment, the invention relates to compounds of formula I or Ia, supra, wherein each of $R^{2a}$ and $R^{2c}$ represents a hydrogen atom and $R^{2b}$ represents a $C_1$-$C_3$-alkoxy-group.

In another preferred embodiment, the invention relates to compounds of formula I or Ia, supra, wherein $R^3$ represents a hydrogen atom or a group selected from $C_1$-$C_6$-alkyl-, $C_3$-$C_6$-cycloalkyl, —($CH_2$)$_q$—($C_3$-$C_6$-cycloalkyl), —($CH_2$)$_q$—O—($C_3$-$C_6$-cycloalkyl), 3- to 10-membered heterocycloalkyl, —($CH_2$)$_q$-(3- to 10-membered heterocycloalkyl), —($CH_2$)$_q$—O-(3- to 10-membered heterocycloalkyl), 4- to 10-membered heterocycloalkenyl, —($CH_2$)$_q$-(4- to 10-membered heterocycloalkenyl), —($CH_2$)$_q$—O-(4- to 10-membered heterocycloalkenyl), aryl, —($CH_2$)$_q$-aryl, —($CH_2$)$_q$—O-aryl, heteroaryl, —($CH_2$)$_q$-heteroaryl, —($CH_2$)$_q$—O-heteroaryl; said group being optionally substituted, identically or differently, with 1, 2, 3, 4 or 5 $R^8$ groups.

In another preferred embodiment, the invention relates to compounds of formula I or Ia, supra, wherein $R^3$ represents a hydrogen atom or a group selected from $C_1$-$C_6$-alkyl-, $C_3$-$C_6$-cycloalkyl, —$(CH_2)_q$—($C_3$-$C_6$-cycloalkyl), 3- to 10-membered heterocycloalkyl, —$(CH_2)_q$-(3- to 10-membered heterocycloalkyl), aryl, —$(CH_2)_q$-aryl, —$(CH_2)_q$—O-aryl, heteroaryl, —$(CH_2)_q$-heteroaryl, —$(CH_2)_q$—O-heteroaryl;

said group being optionally substituted, identically or differently, with 1, 2, 3 or 4 $R^8$ groups.

In another preferred embodiment, the invention relates to compounds of formula I or Ia, supra, wherein $R^3$ represents a hydrogen atom or a group selected from $C_1$-$C_6$-alkyl-, $C_3$-$C_6$-cycloalkyl, —$(CH_2)_q$—($C_3$-$C_6$-cycloalkyl), 3- to 10-membered heterocycloalkyl, —$(CH_2)_q$-(3- to 10-membered heterocycloalkyl), aryl, —$(CH_2)_q$-aryl, —$(CH_2)_q$—O-aryl, heteroaryl, —$(CH_2)_q$-heteroaryl, —$(CH_2)_q$—O-heteroaryl;

said group being optionally substituted, identically or differently, with 1, 2 or 3 $R^8$ groups.

In another preferred embodiment, the invention relates to compounds of formula I or Ia, supra, wherein $R^3$ represents a group selected from:

$C_1$-$C_6$-alkyl-, $C_2$-$C_6$-alkynyl-, $C_3$-$C_6$-cycloalkyl-,

—$(CH_2)_q$-(3- to 10-membered heterocycloalkyl), aryl, —$(CH_2)_q$-aryl,

-(3- to 10-membered heterocycloalkyl)-$(CH_2)_q$— (3- to 10-membered heterocycloalkyl), -(3- to 10-membered heterocycloalkyl)-$(CH_2)_q$-aryl, -(3- to 10-membered heterocycloalkyl)-$(CH_2)_q$-heteroaryl, said group being optionally substituted, identically or differently, with 1, 2, 3, 4 or 5 $R^8$ groups; or when 2 $R^8$ groups are present ortho to each other on an aryl- or heteroaryl-ring, said 2 $R^8$ groups together form a bridge:

*O$(CH_2)_p$O*, wherein * represent the point of attachment to said aryl- or heteroaryl-ring.

In another preferred embodiment, the invention relates to compounds of formula I or Ia, supra, wherein $NR^3R^4$ together represent a 3- to 10-membered heterocycloalkyl group, which is optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl- or —C(═O)$NR^6R^7$.

In another preferred embodiment, the invention relates to compounds of formula I or Ia, supra, wherein $NR^3R^4$ together represent a 3- to 10-membered heterocycloalkyl group, which is optionally substituted, one or more times, identically or differently, cyano-, $C_1$-$C_6$-alkyl-, hydroxy-$C_1$-$C_6$-alkyl-, $C_1$-$C_6$-alkoxy-$C_1$-$C_6$-alkyl-, $C_3$-$C_6$-cycloalkyl-, —$(CH_2)_q$-aryl, —$(CH_2)_q$-heteroaryl, —N($R^4$)C(═O)$R^5$, —$NR^5R^4$ or —$(CH_2)_r$—C(═O)$NR^6R^7$.

In another preferred embodiment, the invention relates to compounds of formula I or Ia, supra, wherein $NR^3R^4$ together represent a benzo fused 3- to 10-membered heterocycloalkyl group.

In another preferred embodiment, the invention relates to compounds of formula I or Ia, supra, wherein $NR^3R^4$ together represent a group selected from:

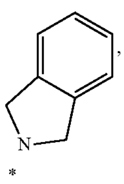,
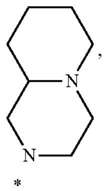,
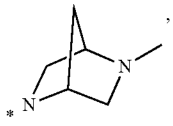,
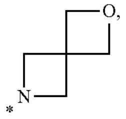
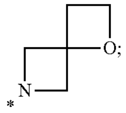

wherein * represents the point of attachment to the rest of the molecule.

In another preferred embodiment, the invention relates to compounds of formula I or Ia, supra, wherein $R^5$ represents a hydrogen atom.

In another preferred embodiment, the invention relates to compounds of formula I or Ia, supra, wherein $R^5$ represents a $C_1$-$C_6$-alkyl- or $C_3$-$C_6$-cycloalkyl-group.

In another preferred embodiment, the invention relates to compounds of formula I or Ia, supra, wherein $R^5$ represents a $C_1$-$C_6$-alkyl-group.

In another preferred embodiment, the invention relates to compounds of formula I or Ia, supra, wherein $R^6$ represents a hydrogen atom.

In another preferred embodiment, the invention relates to compounds of formula I or Ia, supra, wherein $R^6$ represents a $C_1$-$C_6$-alkyl- or $C_3$-$C_6$-cycloalkyl-group.

In another preferred embodiment, the invention relates to compounds of formula I or Ia, supra, wherein $R^7$ represents a hydrogen atom.

In another preferred embodiment, the invention relates to compounds of formula I or Ia, supra, wherein $R^7$ represents a $C_1$-$C_6$-alkyl- or $C_3$-$C_6$-cycloalkyl-group.

In another preferred embodiment, the invention relates to compounds of formula I or Ia, supra, wherein $NR^6R^7$ together represent a 3- to 10-membered heterocycloalkyl group.

In another preferred embodiment, the invention relates to compounds of formula I or Ia, supra, wherein $R^8$ represents halo-, azido-, hydroxy-, cyano-, halo-$C_1$-$C_6$-alkyl-, $C_1$-$C_6$-alkoxy-, hydroxy-$C_1$-$C_6$-alkyl-, —C(═O)$R^5$, —N(H)C(═O)$R^5$, —N(H)C(═O)$NR^5R^4$, —N($R^4$)C(═O)O$R^5$, —N(H)$R^5$, —$NR^5R^4$.

In another preferred embodiment, the invention relates to compounds of formula I or Ia, supra, wherein $R^8$ represents halo- or halo-$C_1$-$C_6$-alkyl-.

In another preferred embodiment, the invention relates to compounds of formula I or Ia, supra, q represents an integer of 1 or 2.

In another preferred embodiment, the invention relates to compounds of formula I or Ia, supra, q represents an integer of 1.

In another preferred embodiment, the invention relates to compounds of formula I, supra, r represents an integer of 0.

In another preferred embodiment, the invention relates to compounds of formula I or Ia, supra, r represents an integer of 1.

In a further embodiment of the above-mentioned aspect, the invention relates to compounds of formula I or Ia, according to any of the above-mentioned embodiments, in the form of or a stereoisomer, a tautomer, an N-oxide, a hydrate, a solvate, or a salt thereof, or a mixture of same.

It is to be understood that the present invention relates also to any combination of the preferred embodiments described above.

Some examples of combinations are given hereinafter. However, the invention is not limited to these combinations.

In a preferred embodiment, the invention relates to compounds of formula I:

I

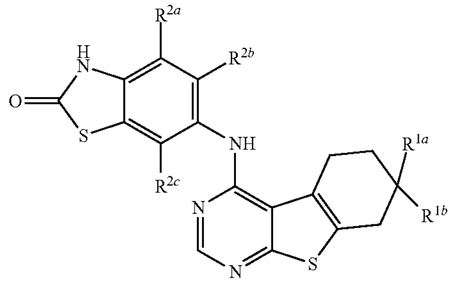

in which:

$R^{1a}$ represents a hydrogen atom or a group selected from:

—O—$C_1$-$C_6$-alkyl, —$(CH_2)_r$—$R^8$, —$(CH_2)_r$—$NR^3R^4$, —$(CH_2)_r$—$N(R^4)C(=O)R^3$, —$(CH_2)_r$—$N(R^4)S(=O)_2R^3$, —$(CH_2)_r$—$C(=O)OR^3$, —$(CH_2)_r$—$C(=O)NR^3R^4$, —$(CH_2)_r$—$N(R^4)C(=O)OR^3$, —$(CH_2)_r$—$N(R^4)C(=O)N(H)R^3$, $R^{1b}$ represents a hydrogen atom or a group selected from:

$C_1$-$C_6$-alkyl-, —$(CH_2)_r$—O—($C_1$-$C_6$-alkyl);

$R^{2a}$ represents a hydrogen atom;

$R^{2b}$ represents a hydrogen atom or a $C_1$-$C_3$-alkoxy-group;

$R^{2c}$ represents a hydrogen atom;

$R^3$ represents a hydrogen atom or a group selected from:

$C_1$-$C_6$-alkyl-, $C_2$-$C_6$-alkynyl-, $C_3$-$C_6$-cycloalkyl-, —$(CH_2)_q$—($C_3$-$C_6$-cycloalkyl), —$(CH_2)_q$—O—($C_3$-$C_6$-cycloalkyl), 3- to 10-membered heterocycloalkyl, —$(CH_2)_q$-(3- to 10-membered heterocycloalkyl), —$(CH_2)_q$—O-(3- to 10-membered heterocycloalkyl), 4- to 10-membered heterocycloalkenyl, —$(CH_2)_q$-(4- to 10-membered heterocycloalkenyl), —$(CH_2)_q$—O-(4- to 10-membered heterocycloalkenyl), aryl, —$(CH_2)_q$-aryl, —$(CH_2)_q$—O-aryl, heteroaryl, —$(CH_2)_q$-heteroaryl, —$(CH_2)_q$—O-heteroaryl, -(3- to 10-membered heterocycloalkyl)-$(CH_2)_q$-(3- to 10-membered heterocycloalkyl), -(3- to 10-membered heterocycloalkyl)-$(CH_2)_q$-aryl, -(3- to 10-membered heterocycloalkyl)-$(CH_2)_q$-heteroaryl, said group being optionally substituted, identically or differently, with 1, 2, 3, 4 or 5 $R^8$ groups; or when 2 $R^8$ groups are present ortho to each other on an aryl- or heteroaryl-ring, said 2 $R^8$ groups together form a bridge:

*$O(CH_2)_pO$*, *NH(C(=O))NH*, wherein * represent the point of attachment to said aryl- or heteroaryl-ring;

$R^4$ represents a hydrogen atom or a group selected from:

$C_1$-$C_6$-alkyl-, —$(CH_2)_q$-aryl, $C_1$-$C_6$-alkoxy-$C_1$-$C_6$-alkyl-; or $NR^3R^4$ together represent a 3- to 10-membered heterocycloalkyl group, a benzo fused 3- to 10-membered heterocycloalkyl group or a 4- to 10-membered heterocycloalkenyl group;

said 3- to 10-membered heterocycloalkyl or 4- to 10-membered heterocycloalkenyl group being optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl-, —$(CH_2)_q$-aryl, —$(CH_2)_q$-heteroaryl, —$N(R^4)C(=O)R^5$, —$NR^5R^4$ or —$(CH_2)_r$—$C(=O)NR^6R^7$;

$R^5$ represents a hydrogen atom, a $C_1$-$C_6$-alkyl- or a $C_3$-$C_6$-cycloalkyl-group;

$R^6$ represents a hydrogen atom, a $C_1$-$C_6$-alkyl- or a $C_3$-$C_6$-cycloalkyl-group;

$R^7$ represents a hydrogen atom, a $C_1$-$C_6$-alkyl- or a $C_3$-$C_6$-cycloalkyl-group; or $NR^6R^7$ together represent a 3- to 10-membered heterocycloalkyl group;

$R^8$ represents halo-, azido-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —$C(=O)R^5$, —$C(=O)O$—$R^5$, —$OC(=O)$—$R^5$,

—$N(H)C(=O)R^5$, —$N(R^4)C(=O)R^5$, —$N(H)C(=O)NR^5R^4$, —$N(R^4)C(=O)NR^5R^4$,

—$N(R^4)C(=O)OR^5$, —$N(H)R^5$, —$NR^5R^4$, —$C(=O)N(H)R^5$, —$C(=O)NR^5R^4$, $R^4$—S—, $R^4$—$S(=O)$—, $R^4$—$S(=O)_2$—, —$N(H)S(=O)R^4$, —$N(R^4)S(=O)R^4$, —$S(=O)N(H)R^5$,

—$S(=O)NR^5R^4$, —$N(H)S(=O)_2R^4$, —$N(R^4)S(=O)_2R^4$, —$S(=O)_2N(H)R^5$, —$S(=O)_2NR^5R^4$,

—$S(=O)(=NR^5)R^4$, —$S(=O)(=NR^4)R^5$ or —$N=S(=O)(R^5)R^4$;

p represents an integer of 1 or 2;

q represents an integer of 1, 2 or 3;

r represents an integer of 0, 1 or 2;

or a tautomer, an N-oxide, a hydrate, a solvate, or a salt thereof, or a mixture of same.

In another preferred embodiment, the invention relates to compounds of formula I:

I

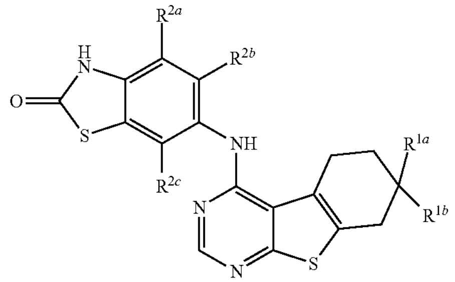

in which:

$R^{1a}$ represents a hydrogen atom or a group selected from:

—O—$C_1$-$C_6$-alkyl, —$(CH_2)_r$—$R^8$, —$(CH_2)_r$—$NR^3R^4$, —$(CH_2)_r$—$N(R^4)C(=O)R^3$, —$(CH_2)_r$—$N(R^4)S(=O)_2R^3$, —$(CH_2)_r$—$C(=O)OR^3$, —$(CH_2)_r$—$C(=O)NR^3R^4$, —$(CH_2)_r$—$N(R^4)C(=O)OR^3$, —$(CH_2)_r$—$N(R^4)C(=O)N(H)R^3$, $R^{1b}$ represents a hydrogen atom or a group selected from: $C_1$-$C_6$-alkyl-, —$(CH_2)_r$—O—($C_1$-$C_6$-alkyl);

$R^{2a}$ represents a hydrogen atom;

$R^{2b}$ represents a hydrogen atom or a $C_1$-$C_3$-alkoxy-group;

$R^{2c}$ represents a hydrogen atom;

$R^3$ represents a hydrogen atom or a group selected from: $C_1$-$C_6$-alkyl-, $C_2$-$C_6$-alkynyl-, $C_3$-$C_6$-cycloalkyl-, —$(CH_2)_q$-(3- to 10-membered heterocycloalkyl), aryl, —$(CH_2)_q$-aryl, -(3- to 10-membered heterocycloalkyl)-$(CH_2)_q$-(3- to 10-membered heterocycloalkyl), -(3- to 10-membered heterocycloalkyl)-$(CH_2)_q$-aryl, -(3- to 10-membered heterocycloalkyl)-$(CH_2)_q$-heteroaryl, said group being optionally substituted, identically or differently, with 1, 2, 3, 4 or 5 $R^8$ groups; or when 2 $R^8$ groups are present ortho to each other on an aryl- or heteroaryl-ring, said 2 $R^8$ groups together form a bridge:

*$O(CH_2)_pO$*, wherein * represent the point of attachment to said aryl- or heteroaryl-ring;

$R^4$ represents a hydrogen atom or a group selected from: $C_1$-$C_6$-alkyl-, —$(CH_2)_q$-aryl, $C_1$-$C_6$-alkoxy-$C_1$-$C_6$-alkyl-; or $NR^3R^4$ together represent a 3- to 10-membered heterocycloalkyl group, a benzo fused 3- to 10-membered heterocycloalkyl group or a 4- to 10-membered heterocycloalkenyl group;

said 3- to 10-membered heterocycloalkyl or 4- to 10-membered heterocycloalkenyl group being optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl-, —$(CH_2)_q$-aryl, —$(CH_2)_q$-heteroaryl, —$N(R^4)C({=}O)R^5$, —$NR^5R^4$ or —$(CH_2)_r$—$C({=}O)NR^6R^7$;

$R^5$ represents a hydrogen atom or a $C_1$-$C_6$-alkyl-group;

$R^6$ represents a hydrogen atom or a $C_1$-$C_6$-alkyl-group;

$R^7$ represents a hydrogen atom or a $C_1$-$C_6$-alkyl-group; or $NR^6R^7$ together represent a 3- to 10-membered heterocycloalkyl group;

$R^8$ represents halo-, azido-, hydroxy-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —$C({=}O)R^5$, —$C({=}O)O$—$R^5$, —$OC({=}O)$—$R^5$, —$N(H)C({=}O)R^5$, —$N(R^4)C({=}O)R^5$, —$N(H)C({=}O)NR^5R^4$, —$N(R^4)C({=}O)NR^5R^4$, —$N(R^4)C({=}O)OR^5$, —$N(H)R^5$, —$NR^5R^4$, —$C({=}O)N(H)R^5$, —$C({=}O)NR^5R^4$, $R^4$—S—, $R^4$—$S({=}O)$—, $R^4$—$S({=}O)_2$—, —$N(H)S({=}O)R^4$, —$N(R^4)S({=}O)R^4$, —$S({=}O)N(H)R^5$, —$S({=}O)NR^5R^4$, —$N(H)S({=}O)_2R^4$, —$N(R^4)S({=}O)_2R^4$, —$S({=}O)_2N(H)R^5$, —$S({=}O)_2NR^5R^4$, —$S({=}O)({=}NR^5)R^4$, —$S({=}O)({=}NR^4)R^5$ or —$N{=}S({=}O)(R^5)R^4$;

p represents an integer of 1 or 2;

q represents an integer of 1 or 2;

r represents an integer of 0 or 1;

or a tautomer, an N-oxide, a hydrate, a solvate, or a salt thereof, or a mixture of same.

In another preferred embodiment, the invention relates to compounds of formula I:

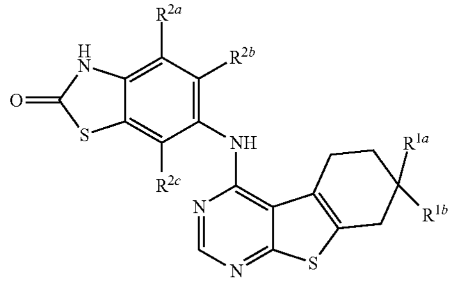

I in which:

$R^{1a}$ represents a hydrogen atom or a group selected from: —O—$C_1$-$C_6$-alkyl, —$(CH_2)_r$—$R^8$, —$(CH_2)_r$—$NR^3R^4$, —$(CH_2)_r$—$N(R^4)C({=}O)R^3$, —$(CH_2)_r$—$N(R^4)S({=}O)_2R^3$, —$(CH_2)_r$—$C({=}O)OR^3$, —$(CH_2)_r$—$C({=}O)NR^3R^4$, —$(CH_2)_r$—$N(R^4)C({=}O)OR^3$, —$(CH_2)_r$—$N(R^4)C({=}O)N(H)R^3$, $R^{1b}$ represents a hydrogen atom or a group selected from: $C_1$-$C_6$-alkyl-, —$(CH_2)_r$—O—($C_1$-$C_6$-alkyl);

$R^{2a}$ represents a hydrogen atom;

$R^{2b}$ represents a hydrogen atom or a $C_1$-$C_3$-alkoxy-group;

$R^{2c}$ represents a hydrogen atom;

$R^3$ represents a hydrogen atom or a group selected from: $C_1$-$C_6$-alkyl-, $C_2$-$C_6$-alkynyl-, $C_3$-$C_6$-cycloalkyl-, —$(CH_2)_q$-(3- to 10-membered heterocycloalkyl), aryl, —$(CH_2)_q$-aryl, -(3- to 10-membered heterocycloalkyl)-$(CH_2)_q$-(3- to 10-membered heterocycloalkyl), -(3- to 10-membered heterocycloalkyl)-$(CH_2)_q$-aryl, -(3- to 10-membered heterocycloalkyl)-$(CH_2)_q$-heteroaryl, said group being optionally substituted, identically or differently, with 1, 2, 3, 4 or 5 $R^8$ groups; or when 2 $R^8$ groups are present ortho to each other on an aryl- or heteroaryl-ring, said 2 $R^8$ groups together form a bridge:

*$O(CH_2)_pO$*, wherein * represent the point of attachment to said aryl- or heteroaryl-ring;

$R^4$ represents a hydrogen atom or a group selected from: $C_1$-$C_6$-alkyl-, —$(CH_2)_q$-aryl, $C_1$-$C_6$-alkoxy-$C_1$-$C_6$-alkyl-; or $NR^3R^4$ together represent a 3- to 10-membered heterocycloalkyl group, a benzo fused 3- to 10-membered heterocycloalkyl group or a 4- to 10-membered heterocycloalkenyl group;

said 3- to 10-membered heterocycloalkyl or 4- to 10-membered heterocycloalkenyl group being optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl-, —$(CH_2)_q$-aryl, —$(CH_2)_q$-heteroaryl, —$N(R^4)C({=}O)R^5$, —$NR^5R^4$ or —$(CH_2)_r$—$C({=}O)NR^6R^7$;

$R^5$ represents a hydrogen atom or a $C_1$-$C_6$-alkyl-group;

$R^6$ represents a hydrogen atom or a $C_1$-$C_6$-alkyl-group;

$R^7$ represents a hydrogen atom or a $C_1$-$C_6$-alkyl-group; or $NR^6R^7$ together represent a 3- to 10-membered heterocycloalkyl group;

$R^8$ represents halo-, azido-, hydroxy-, cyano-, $C_1$-$C_6$-alkyl-, halo-$C_1$-$C_6$-alkyl-, $C_1$-$C_6$-alkoxy-, hydroxy-$C_1$-$C_6$-alkyl-, —C(═O)$R^5$, —N(H)C(═O)$R^5$, —N($R^4$)C(═O)$R^5$, —N(H)C(═O)N$R^5R^4$, —N($R^4$)C(═O)O$R^5$, —N(H)$R^5$, —N$R^5R^4$;

p represents an integer of 1 or 2;

q represents an integer of 1 or 2;

r represents an integer of 0 or 1;

or a tautomer, an N-oxide, a hydrate, a solvate, or a salt thereof, or a mixture of same.

In another preferred embodiment, the invention relates to compounds of formula I:

I

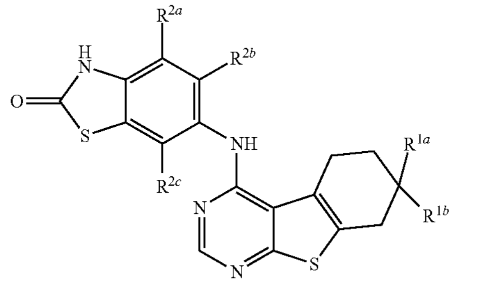

in which:

$R^{1a}$ represents a hydrogen atom or a group selected from: —O—$C_1$-$C_6$-alkyl, —$(CH_2)_r$—$R^8$, —$(CH_2)_r$—N$R^3R^4$, —$(CH_2)_r$—N($R^4$)C(═O)$R^3$, —$(CH_2)_r$—N($R^4$)S(═O)$_2R^3$, —$(CH_2)_r$—C(═O)O$R^3$, —$(CH_2)_r$—C(═O)N$R^3R^4$, —$(CH_2)_r$—N($R^4$)C(═O)O$R^3$, —$(CH_2)_r$—N($R^4$)C(═O)N(H)$R^3$, $R^{1b}$ represents a hydrogen atom or a group selected from: $C_1$-$C_6$-alkyl-, —$(CH_2)_r$—O—($C_1$-$C_6$-alkyl);

$R^{2a}$ represents a hydrogen atom;

$R^{2b}$ represents a hydrogen atom or a $C_1$-$C_3$-alkoxy-group; preferably a methoxy-group;

$R^{2c}$ represents a hydrogen atom;

$R^3$ represents a hydrogen atom or a group selected from: $C_1$-$C_6$-alkyl-, $C_2$-$C_6$-alkynyl-, $C_3$-$C_6$-cycloalkyl-, —$(CH_2)_q$-(3- to 10-membered heterocycloalkyl), aryl, —$(CH_2)_q$-aryl, -(3- to 10-membered heterocycloalkyl)-$(CH_2)_q$-(3- to 10-membered heterocycloalkyl), -(3- to 10-membered heterocycloalkyl)-$(CH_2)_q$-aryl, -(3- to 10-membered heterocycloalkyl)-$(CH_2)_q$-heteroaryl, said group being optionally substituted, identically or differently, with 1, 2 or 3 $R^8$ groups; or when 2 $R^8$ groups are present ortho to each other on an aryl- or heteroaryl-ring, said 2 $R^8$ groups together form a bridge:

*O$(CH_2)_p$O*, wherein * represent the point of attachment to said aryl- or heteroaryl-ring;

$R^4$ represents a hydrogen atom or a group selected from: $C_1$-$C_6$-alkyl-, —$(CH_2)_q$-aryl, $C_1$-$C_6$-alkoxy-$C_1$-$C_6$-alkyl-; or N$R^3R^4$ together represent a 3- to 10-membered heterocycloalkyl group or a benzo fused 3- to 10-membered heterocycloalkyl group;

said 3- to 10-membered heterocycloalkyl group being optionally substituted, one or more times, identically or differently, with halo-, cyano-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_3$-$C_6$-cycloalkyl-, —$(CH_2)_q$-aryl, —$(CH_2)_q$-heteroaryl, —N($R^4$)C(═O)$R^5$, —N$R^5R^4$ or —$(CH_2)_r$—C(═O)N$R^6R^7$;

$R^5$ represents a hydrogen atom or a $C_1$-$C_6$-alkyl-group;

$R^6$ represents a hydrogen atom or a $C_1$-$C_6$-alkyl-group;

$R^7$ represents a hydrogen atom or a $C_1$-$C_6$-alkyl-group; or

N$R^6R^7$ together represent a 3- to 10-membered heterocycloalkyl group;

$R^8$ represents halo-, azido-, hydroxy-, cyano-, $C_1$-$C_6$-alkyl-, halo-$C_1$-$C_6$-alkyl-, $C_1$-$C_6$-alkoxy-, hydroxy-$C_1$-$C_6$-alkyl-, —C(═O)$R^5$, —N(H)C(═O)$R^5$, —N($R^4$)C(═O)$R^5$, —N(H)C(═O)N$R^5R^4$, —N($R^4$)C(═O)O$R^5$, —N(H)$R^5$, —N$R^5R^4$;

p represents an integer of 1 or 2;

q represents an integer of 1 or 2;

r represents an integer of 0 or 1;

or a tautomer, an N-oxide, a hydrate, a solvate, or a salt thereof, or a mixture of same.

In another preferred embodiment, the invention relates to compounds of formula Ia:

Ia

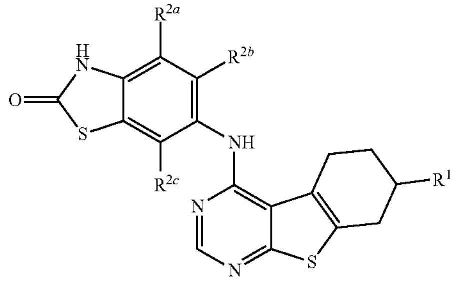

in which:

$R^1$ represents a group selected from: —C(═O)O—$R^3$, —C(═O)N(H)$R^3$, —C(═O)N$R^3R^4$;

$R^{2a}$ represents a hydrogen atom or a halogen atom or a group selected from: $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —N(H)$R^5$, —N$R^5R^4$;

$R^{2b}$ represents a hydrogen atom or a halogen atom or a group selected from: $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —N(H)$R^5$, —N$R^5R^4$, —N(H)C(═O)$R^5$, —N($R^4$)C(═O)$R^5$, —N(H)C(═O)N$R^5R^4$, —N($R^4$)C(═O)N$R^5R^4$, —C(═O)N(H)$R^5$, —C(═O)N$R^5R^4$;

$R^{2c}$ represents a hydrogen atom or a halogen atom or a group selected from: $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —N(H)$R^5$, —N$R^5R^4$;

$R^3$ represents a hydrogen atom or a group selected from: $C_1$-$C_6$-alkyl-, $C_3$-$C_6$-cycloalkyl, —$(CH_2)_q$—($C_3$-$C_6$-cycloalkyl), —$(CH_2)_q$—O—($C_3$-$C_6$-cycloalkyl), 3- to 10-membered heterocycloalkyl, —$(CH_2)_q$-(3- to 10-membered heterocycloalkyl), —$(CH_2)_q$—O-(3- to 10-membered heterocycloalkyl), 4- to 10-membered heterocycloalkenyl, —$(CH_2)_q$-(4- to 10-membered heterocycloalkenyl), —$(CH_2)_q$—O-(4- to 10-membered heterocycloalkenyl), aryl, —$(CH_2)_q$-aryl, —$(CH_2)_q$—O-aryl, heteroaryl, —$(CH_2)_q$-heteroaryl, —$(CH_2)_q$—O-heteroaryl;

said group being optionally substituted, identically or differently, with 1, 2, 3, 4 or 5 $R^8$ groups; or when 2 $R^8$ groups are present ortho to each other on an aryl- or heteroaryl-ring, said 2 $R^8$ groups together form a bridge:

$*O(CH_2)_pO*$, $*NH(C(=O))NH*$, wherein * represent the point of attachment to said aryl- or heteroaryl-ring;

$R^4$ represents a $C_1$-$C_6$-alkyl-group; or $NR^3R^4$ together represent a 3- to 10-membered heterocycloalkyl or a 4- to 10-membered heterocycloalkenyl group, which is optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl- or $—C(=O)NR^6R^7$;

$R^5$ represents a hydrogen atom, a $C_1$-$C_6$-alkyl- or $C_3$-$C_6$-cycloalkyl-group;

$R^6$ represents a hydrogen atom, a $C_1$-$C_6$-alkyl- or $C_3$-$C_6$-cycloalkyl-group;

$R^7$ represents a hydrogen atom, a $C_1$-$C_6$-alkyl- or $C_3$-$C_6$-cycloalkyl-group; or $NR^6R^7$ together represent a 3- to 10-membered heterocycloalkyl group;

$R^8$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5—O—$, $—C(=O)R^5$, $—C(=O)O—R^5$, $—OC(=O)—R^5$, $—N(H)C(=O)R^5$, $—N(R^4)C(=O)R^5$, $—N(H)C(=O)NR^5R^4$, $—N(R^4)C(=O)NR^5R^4$, $—N(H)R^5$, $—NR^5R^4$, $—C(=O)N(H)R^5$, $—C(=O)NR^5R^4$, $R^4—S—$, $R^4—S(=O)—$, $R^4—S(=O)_2—$, $—N(H)S(=O)R^4$, $—N(R^4)S(=O)R^4$, $—S(=O)N(H)R^5$, $—S(=O)NR^5R^4$, $—N(H)S(=O)_2R^4$, $—N(R^4)S(=O)_2R^4$, $—S(=O)_2N(H)R^5$, $—S(=O)_2NR^5R^4$, $—S(=O)(=NR^5)R^4$, $—S(=O)(=NR^4)R^5$ or $—N=S(=O)(R^5)R^4$;

p represents an integer of 1 or 2;

q represents an integer of 1, 2 or 3;

or a tautomer, an N-oxide, a hydrate, a solvate, or a salt thereof, or a mixture of same.

In another preferred embodiment, the invention relates to compounds of formula Ia:

Ia

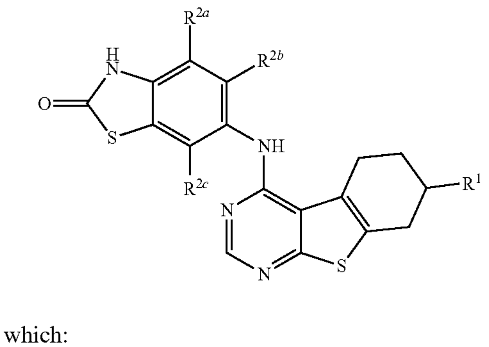

in which:

$R^1$ represents a group selected from $—C(=O)O—R^3$, $—C(=O)N(H)R^3$, $—C(=O)NR^3R^4$;

$R^{2a}$ represents a hydrogen atom;

$R^{2b}$ represents a hydrogen atom or a group selected from $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, $—N(H)R^5$, $—NR^5R^4$, $—N(H)C(=O)R^5$, $—N(R^4)C(=O)R^5$, $—N(H)C(=O)NR^5R^4$, $—N(R^4)C(=O)NR^5R^4$, $—C(=O)N(H)R^5$, $—C(=O)NR^5R^4$;

$R^{2c}$ represents a hydrogen atom or a halogen atom or a group selected from $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, $—N(H)R^5$, $—NR^5R^4$;

$R^3$ represents a hydrogen atom or a group selected from $C_1$-$C_6$-alkyl-, $C_3$-$C_6$-cycloalkyl, $—(CH_2)_q—(C_3$-$C_6$-cycloalkyl), $—(CH_2)_q—O—(C_3$-$C_6$-cycloalkyl), 3- to 10-membered heterocycloalkyl, $—(CH_2)_q$-(3- to 10-membered heterocycloalkyl), $—(CH_2)_q—O$-(3- to 10-membered heterocycloalkyl), 4- to 10-membered heterocycloalkenyl, $—(CH_2)_q$-(4- to 10-membered heterocycloalkenyl), $—(CH_2)_q—O$-(4- to 10-membered heterocycloalkenyl), aryl, $—(CH_2)_q$-aryl, $—(CH_2)_q—O$-aryl, heteroaryl, $—(CH_2)_q$-heteroaryl, $—(CH_2)_q—O$-heteroaryl;

said group being optionally substituted, identically or differently, with 1, 2, 3, 4 or 5 $R^8$ groups; or when 2 $R^8$ groups are present ortho to each other on an aryl- or heteroaryl-ring, said 2 $R^8$ groups together form a bridge:

$*O(CH_2)_pO*$, $*NH(C(=O))NH*$, wherein * represent the point of attachment to said aryl- or heteroaryl-ring;

$R^4$ represents a $C_1$-$C_6$-alkyl-group; or $NR^3R^4$ together represent a 3- to 10-membered heterocycloalkyl or a 4- to 10-membered heterocycloalkenyl group, which is optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl- or $—C(=O)NR^6R^7$;

$R^5$ represents a hydrogen atom, a $C_1$-$C_6$-alkyl- or $C_3$-$C_6$-cycloalkyl-group;

$R^6$ represents a hydrogen atom, a $C_1$-$C_6$-alkyl- or $C_3$-$C_6$-cycloalkyl-group;

$R^7$ represents a hydrogen atom, a $C_1$-$C_6$-alkyl- or $C_3$-$C_6$-cycloalkyl-group; or $NR^6R^7$ together represent a 3- to 10-membered heterocycloalkyl group;

$R^8$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5—O—$, $—C(=O)R^5$, $—C(=O)O—R^5$, $—OC(=O)—R^5$, $—N(H)C(=O)R^5$, $—N(R^4)C(=O)R^5$, $—N(H)C(=O)NR^5R^4$, $—N(R^4)C(=O)NR^5R^4$, $—N(H)R^5$, $—NR^5R^4$, $—C(=O)N(H)R^5$, $—C(=O)NR^5R^4$, $R^4—S—$, $R^4—S(=O)—$, $R^4—S(=O)_2—$, $—N(H)S(=O)R^4$, $—N(R^4)S(=O)R^4$, $—S(=O)N(H)R^5$, $—S(=O)NR^5R^4$, $—N(H)S(=O)_2R^4$, —$N(R^4)S(=O)_2R^4$, —$S(=O)_2N(H)R^5$, —$S(=O)_2NR^5R^4$, —$S(=O)(=NR^5)R^4$, —$S(=O)(=NR^4)R^5$ or —$N=S(=O)(R^5)R^4$;

p represents an integer of 1 or 2;

q represents an integer of 1, 2 or 3;

or a tautomer, an N-oxide, a hydrate, a solvate, or a salt thereof, or a mixture of same.

In another preferred embodiment, the invention relates to compounds of formula Ia:

Ia

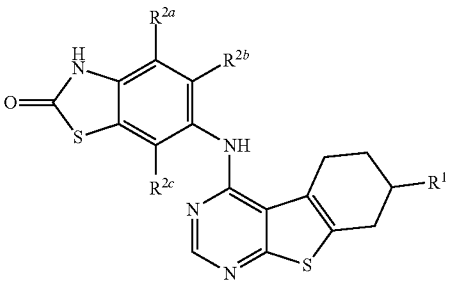

in which:

$R^1$ represents a group selected from —$C(=O)O$—$R^3$, —$C(=O)N(H)R^3$, —$C(=O)NR^3R^4$;

$R^{2a}$ represents a hydrogen atom;

$R^{2b}$ represents a hydrogen atom or a group selected from $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —$N(H)R^5$, —$NR^5R^4$;

$R^{2c}$ represents a hydrogen atom;

$R^3$ represents a hydrogen atom or a group selected from $C_1$-$C_6$-alkyl-, $C_3$-$C_6$-cycloalkyl, —$(CH_2)_q$—($C_3$-$C_6$-cycloalkyl), —$(CH_2)_q$—O—($C_3$-$C_6$-cycloalkyl), 3- to 10-membered heterocycloalkyl, —$(CH_2)_q$-(3- to 10-membered heterocycloalkyl), —$(CH_2)_q$—O-(3- to 10-membered heterocycloalkyl), 4- to 10-membered heterocycloalkenyl, —$(CH_2)_q$-(4- to 10-membered heterocycloalkenyl), —$(CH_2)_q$—O-(4- to 10-membered heterocycloalkenyl), aryl, —$(CH_2)_q$-aryl, —$(CH_2)_q$—O-aryl, heteroaryl, —$(CH_2)_q$-heteroaryl, —$(CH_2)_q$—O-heteroaryl;

said group being optionally substituted, identically or differently, with 1, 2, 3, 4 or 5 $R^8$ groups; or when 2 $R^8$ groups are present ortho to each other on an aryl- or heteroaryl-ring, said 2 $R^8$ groups together form a bridge:

*$O(CH_2)_pO$*, *NH(C(=O))NH*, wherein * represent the point of attachment to said aryl- or heteroaryl-ring;

$R^4$ represents a $C_1$-$C_6$-alkyl-group; or $NR^3R^4$ together represent a 3- to 10-membered heterocycloalkyl or a 4- to 10-membered heterocycloalkenyl group, which is optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl- or —$C(=O)NR^6R^7$;

$R^5$ represents a hydrogen atom, a $C_1$-$C_6$-alkyl- or $C_3$-$C_6$-cycloalkyl-group;

$R^6$ represents a hydrogen atom, a $C_1$-$C_6$-alkyl- or $C_3$-$C_6$-cycloalkyl-group;

$R^7$ represents a hydrogen atom, a $C_1$-$C_6$-alkyl- or $C_3$-$C_6$-cycloalkyl-group; or $NR^6R^7$ together represent a 3- to 10-membered heterocycloalkyl group;

$R^8$ represents halo-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —$C(=O)R^5$, —$C(=O)O$—$R^5$, —$OC(=O)$—$R^5$, —$N(H)C(=O)R^5$, —$N(R^4)C(=O)R^5$, —$N(H)C(=O)NR^5R^4$, —$N(R^4)C(=O)NR^5R^4$, —$N(H)R^5$, —$NR^5R^4$, —$C(=O)N(H)R^5$, —$C(=O)NR^5R^4$, $R^4$—S—, $R^4$—S(=O)—, $R^4$—$S(=O)_2$—, —$N(H)S(=O)R^4$, —$N(R^4)S(=O)R^4$, —$S(=O)N(H)R^5$, —$S(=O)NR^5R^4$, —$N(H)S(=O)_2R^4$, —$N(R^4)S(=O)_2R^4$, —$S(=O)_2N(H)R^5$, —$S(=O)_2NR^5R^4$, —$S(=O)(=NR^5)R^4$, —$S(=O)(=NR^4)R^5$ or —$N=S(=O)(R^5)R^4$;

p represents an integer of 1 or 2;

q represents an integer of 1, 2 or 3;

or a tautomer, an N-oxide, a hydrate, a solvate, or a salt thereof, or a mixture of same.

In another preferred embodiment, the invention relates to compounds of formula Ia:

Ia

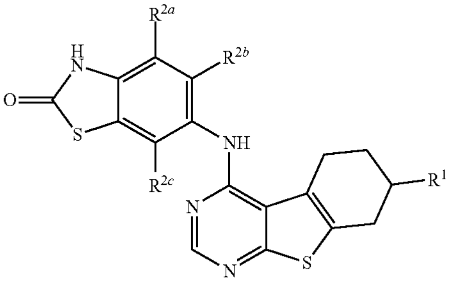

in which:

$R^1$ represents a group selected from —$C(=O)O$—$R^3$, —$C(=O)N(H)R^3$, —$C(=O)NR^3R^4$;

$R^{2a}$ represents a hydrogen atom;

$R^{2b}$ represents a hydrogen atom or a group selected from $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —$N(H)R^5$, —$NR^5R^4$;

$R^{2c}$ represents a hydrogen atom;

$R^3$ represents a hydrogen atom or a group selected from $C_1$-$C_6$-alkyl-, $C_3$-$C_6$-cycloalkyl, —$(CH_2)_q$—($C_3$-$C_6$-cycloalkyl), —$(CH_2)_q$—O—($C_3$-$C_6$-cycloalkyl), 3- to 10-membered heterocycloalkyl, —$(CH_2)_q$-(3- to 10-membered heterocycloalkyl), aryl, —$(CH_2)_q$-aryl, —$(CH_2)_q$—O-aryl, heteroaryl, —$(CH_2)_q$-heteroaryl, —$(CH_2)_q$—O-heteroaryl;

said group being optionally substituted, identically or differently, with 1, 2, 3, 4 or 5 $R^8$ groups; or when 2 $R^8$ groups are present ortho to each other on an aryl- or heteroaryl-ring, said 2 $R^8$ groups together form a bridge:

*$O(CH_2)_pO$*, *NH(C(=O))NH*, wherein * represent the point of attachment to said aryl- or heteroaryl-ring;

$R^4$ represents a $C_1$-$C_6$-alkyl-group; or $NR^3R^4$ together represent a 3- to 10-membered heterocycloalkyl or a 4- to 10-membered heterocycloalkenyl group, which is optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl- or —C(=O)$NR^6R^7$;

$R^5$ represents a hydrogen atom, a $C_1$-$C_6$-alkyl- or $C_3$-$C_6$-cycloalkyl-group;

$R^6$ represents a hydrogen atom, a $C_1$-$C_6$-alkyl- or $C_3$-$C_6$-cycloalkyl-group;

$R^7$ represents a hydrogen atom, a $C_1$-$C_6$-alkyl- or $C_3$-$C_6$-cycloalkyl-group; or $NR^6R^7$ together represent a 3- to 10-membered heterocycloalkyl group;

$R^8$ represents halo-, hydroxy-, oxo-(O=), cyano-, nitro-, $C_1$-$C_6$-alkyl-,
$C_2$-$C_6$-alkenyl-, $C_2$-$C_6$-alkynyl-, halo-$C_1$-$C_6$-alkyl-, $C_1$-$C_6$-alkoxy-,
halo-$C_1$-$C_6$-alkoxy-, hydroxy-$C_1$-$C_6$-alkyl-, $C_1$-$C_6$-alkoxy-$C_1$-$C_6$-alkyl-,
halo-$C_1$-$C_6$-alkoxy-$C_1$-$C_6$-alkyl-, $R^5$—O—, —C(=O)$R^5$, —C(=O)O—$R^5$, —OC(=O)—$R^5$,
—N(H)C(=O)$R^5$, —N($R^4$)C(=O)$R^5$, —N(H)C(=O)$NR^5R^4$, —N($R^4$)C(=O)$NR^5R^4$, —N(H)$R^5$,
—$NR^5R^4$, —C(=O)N(H)$R^5$, —C(=O)$NR^5R^4$, $R^4$—S—, $R^4$—S(=O)—, $R^4$—S(=O)$_2$—,
—N(H)S(=O)$R^4$, —N($R^4$)S(=O)$R^4$, —S(=O)N(H)$R^5$, —S(=O)$NR^5R^4$, —N(H)S(=O)$_2R^4$,
—N($R^4$)S(=O)$_2R^4$, —S(=O)$_2$N(H)$R^5$, —S(=O)$_2NR^5R^4$, —S(=O)(=$NR^5$)$R^4$, —S(=O)(=$NR^4$)$R^5$ or —N=S(=O)($R^5$)$R^4$;

p represents an integer of 1 or 2;

q represents an integer of 1, 2 or 3;

or a tautomer, an N-oxide, a hydrate, a solvate, or a salt thereof, or a mixture of same.

In a preferred embodiment, the invention relates to compounds of formula Ia:

Ia

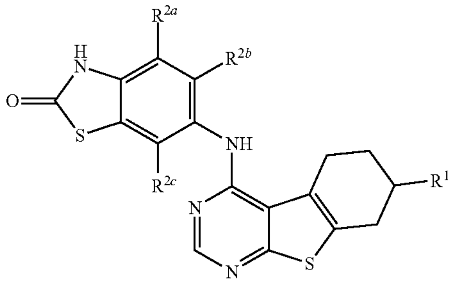

in which:

$R^1$ represents a group selected from —C(=O)O—$R^3$, —C(=O)N(H)$R^3$,
—C(=O)$NR^3R^4$;

$R^{2a}$ represents a hydrogen atom;

$R^{2b}$ represents a hydrogen atom or a halogen atom or a group selected from
$C_1$-$C_3$-alkyl-, $C_1$-$C_3$-alkoxy-, halo-$C_1$-$C_3$-alkyl-, halo-$C_1$-$C_3$-alkoxy-, hydroxy-,
cyano-, —N(H)$R^5$, —$NR^5R^4$, —N(H)C(=O)$R^5$, —N($R^4$)C(=O)$R^5$, —N(H)C(=O)$NR^5R^4$,
—N($R^4$)C(=O)$NR^5R^4$, —C(=O)N(H)$R^5$, —C(=O)$NR^5R^4$;

$R^{2c}$ represents a hydrogen atom;

$R^3$ represents a hydrogen atom or a group selected from
$C_1$-$C_6$-alkyl-, $C_3$-$C_6$-cycloalkyl, —$(CH_2)_q$—($C_3$-$C_6$-cycloalkyl),
—$(CH_2)_q$—O—($C_3$-$C_6$-cycloalkyl), 3- to 10-membered heterocycloalkyl, —$(CH_2)_q$-(3- to 10-membered heterocycloalkyl),
aryl, —$(CH_2)_q$-aryl, —$(CH_2)_q$—O-aryl, heteroaryl, —$(CH_2)_q$-heteroaryl, —$(CH_2)_q$—O-heteroaryl;
said group being optionally substituted, identically or differently, with 1, 2, 3 or 4 $R^8$ groups; or
when 2 $R^8$ groups are present ortho to each other on an aryl- or heteroaryl-ring, said 2 $R^8$ groups together form a bridge:
*$O(CH_2)_pO$*, *NH(C(=O))NH*, wherein * represent the point of attachment to said aryl- or heteroaryl-ring;

$R^4$ represents a $C_1$-$C_6$-alkyl-group; or $NR^3R^4$ together represent a 3- to 10-membered heterocycloalkyl,
which is optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl- or —C(=O)$NR^6R^7$;

$R^5$ represents a hydrogen atom, a $C_1$-$C_6$-alkyl- or $C_3$-$C_6$-cycloalkyl-group;

$R^6$ represents a hydrogen atom, a $C_1$-$C_6$-alkyl- or $C_3$-$C_6$-cycloalkyl-group;

$R^7$ represents a hydrogen atom, a $C_1$-$C_6$-alkyl- or $C_3$-$C_6$-cycloalkyl-group; or $NR^6R^7$ together represent a 3- to 10-membered heterocycloalkyl group;

$R^8$ represents halo-, hydroxy-, oxo-(O=), cyano-, nitro-, $C_1$-$C_6$-alkyl-,
$C_2$-$C_6$-alkenyl-, $C_2$-$C_6$-alkynyl-, halo-$C_1$-$C_6$-alkyl-, $C_1$-$C_6$-alkoxy-,
halo-$C_1$-$C_6$-alkoxy-, hydroxy-$C_1$-$C_6$-alkyl-, $C_1$-$C_6$-alkoxy-$C_1$-$C_6$-alkyl-,
halo-$C_1$-$C_6$-alkoxy-$C_1$-$C_6$-alkyl-, $R^5$—O—, —C(=O)$R^5$, —C(=O)O—$R^5$, —OC(=O)—$R^5$,
—N(H)C(=O)$R^5$, —N($R^4$)C(=O)$R^5$, —N(H)C(=O)$NR^5R^4$, —N($R^4$)C(=O)$NR^5R^4$, —N(H)$R^5$,
—$NR^5R^4$, —C(=O)N(H)$R^5$, —C(=O)$NR^5R^4$, $R^4$—S—, $R^4$—S(=O)—, $R^4$—S(=O)$_2$—,
—N(H)S(=O)$R^4$, —N($R^4$)S(=O)$R^4$, —S(=O)N(H)$R^5$, —S(=O)$NR^5R^4$, —N(H)S(=O)$_2R^4$,
—N($R^4$)S(=O)$_2R^4$, —S(=O)$_2$N(H)$R^5$, —S(=O)$_2NR^5R^4$, —S(=O)(=$NR^5$)$R^4$, —S(=O)(=$NR^4$)$R^5$ or —N=S(=O)($R^5$)$R^4$;

p represents an integer of 1 or 2;

q represents an integer of 1, 2 or 3;

or a tautomer, an N-oxide, a hydrate, a solvate, or a salt thereof, or a mixture of same.

In another preferred embodiment, the invention relates to compounds of formula Ia:

Ia

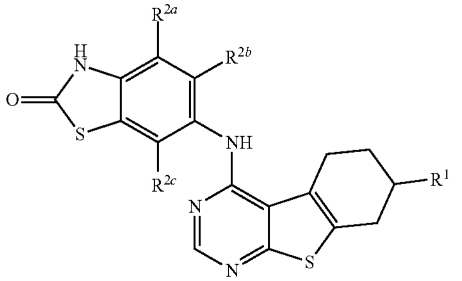

in which:

$R^1$ represents a group selected from —C(═O)O—$R^3$, —C(═O)N(H)$R^3$, —C(═O)$NR^3R^4$;

$R^{2a}$ represents a hydrogen atom or a halogen atom or a group selected from $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —N(H)$R^5$, —$NR^5R^4$;

$R^{2b}$ represents a hydrogen atom or a halogen atom or a group selected from $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —N(H)$R^5$, —$NR^5R^4$, —N(H)C(═O)$R^5$, —N($R^4$)C(═O)$R^5$, —N(H)C(═O)$NR^5R^4$, —N($R^4$)C(═O)$NR^5R^4$, —C(═O)N(H)$R^5$, —C(═O)$NR^5R^4$;

$R^{2c}$ represents a hydrogen atom or a halogen atom or a group selected from $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —N(H)$R^5$, —$NR^5R^4$;

$R^3$ represents a hydrogen atom or a group selected from $C_1$-$C_6$-alkyl-, $C_3$-$C_6$-cycloalkyl, —$(CH_2)_q$—($C_3$-$C_6$-cycloalkyl), 3- to 10-membered heterocycloalkyl, —$(CH_2)_q$-(3- to 10-membered heterocycloalkyl), aryl, —$(CH_2)_q$-aryl, —$(CH_2)_q$—O-aryl, heteroaryl, —$(CH_2)_q$-heteroaryl, —$(CH_2)_q$—O-heteroaryl;

said group being optionally substituted, identically or differently, with 1, 2 or 3 $R^8$ groups; or when 2 $R^8$ groups are present ortho to each other on an aryl- or heteroaryl-ring, said 2 $R^8$ groups together form a bridge:

*O$(CH_2)_p$O*, *NH(C(═O))NH*, wherein * represent the point of attachment to said aryl- or heteroaryl-ring;

$R^4$ represents a $C_1$-$C_6$-alkyl-group; or $NR^3R^4$ together represent a 3- to 10-membered heterocycloalkyl; which is optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl- or —C(═O)$NR^6R^7$;

$R^5$ represents a hydrogen atom, a $C_1$-$C_6$-alkyl- or $C_3$-$C_6$-cycloalkyl-group;

$R^6$ represents a hydrogen atom, a $C_1$-$C_6$-alkyl- or $C_3$-$C_6$-cycloalkyl-group;

$R^7$ represents a hydrogen atom, a $C_1$-$C_6$-alkyl- or $C_3$-$C_6$-cycloalkyl-group; or $NR^6R^7$ together represent a 3- to 10-membered heterocycloalkyl group;

$R^8$ represents halo-, hydroxy-, oxo-(O═), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(═O)$R^5$, —C(═O)O—$R^5$, —OC(═O)—$R^5$, —N(H)C(═O)$R^5$, —N($R^4$)C(═O)$R^5$, —N(H)C(═O)$NR^5R^4$, —N($R^4$)C(═O)$NR^5R^4$, —N(H)$R^5$, —$NR^5R^4$, —C(═O)N(H)$R^5$, —C(═O)$NR^5R^4$, $R^4$—S—, $R^4$—S(═O)—, $R^4$—S(═O)$_2$—, —N(H)S(═O)$R^4$, —N($R^4$)S(═O)$R^4$, —S(═O)N(H)$R^5$, —S(═O)$NR^5R^4$, —N(H)S(═O)$_2R^4$, —N($R^4$)S(═O)$_2R^4$, —S(═O)$_2$N(H)$R^5$, —S(═O)$_2$ $NR^5R^4$, —S(═O)(═$NR^5$)$R^4$, —S(═O)(═$NR^4$)$R^5$ or —N═S(═O)($R^5$)$R^4$;

p represents an integer of 1 or 2;

q represents an integer of 1, 2 or 3;

or a tautomer, an N-oxide, a hydrate, a solvate, or a salt thereof, or a mixture of same.

In another preferred embodiment, the invention relates to compounds of formula Ia:

Ia

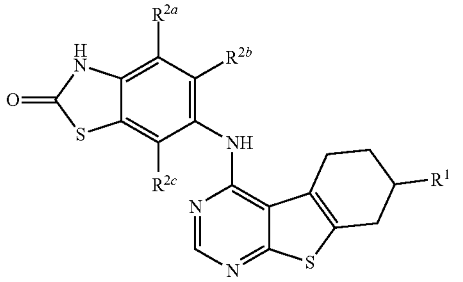

in which:

$R^1$ represents a group selected from: —C(═O)O—$R^3$, —C(═O)N(H)$R^3$, —C(═O)$NR^3R^4$;

$R^{2a}$ represents a hydrogen atom;

$R^{2b}$ represents a hydrogen atom or $C_1$-$C_3$-alkoxy-group; preferably a methoxy-group;

$R^{2c}$ represents a hydrogen atom;

$R^3$ represents a hydrogen atom or a group selected from $C_1$-$C_6$-alkyl-, $C_3$-$C_6$-cycloalkyl, —$(CH_2)_q$—($C_3$-$C_6$-cycloalkyl), 3- to 10-membered heterocycloalkyl, —$(CH_2)_q$-(3- to 10-membered heterocycloalkyl), aryl, —$(CH_2)_q$-aryl, —$(CH_2)_q$—O-aryl, heteroaryl, —$(CH_2)_q$-heteroaryl, —$(CH_2)_q$—O-heteroaryl;

said group being optionally substituted, identically or differently, with 1, 2 or 3 $R^8$ groups; or when 2 $R^8$ groups are present ortho to each other on an aryl- or heteroaryl-ring, said 2 $R^8$ groups together form a bridge:

*O$(CH_2)_p$O*, *NH(C(═O))NH*, wherein * represent the point of attachment to said aryl- or heteroaryl-ring;

$R^4$ represents a $C_1$-$C_6$-alkyl-group; or $NR^3R^4$ together represent a 3- to 10-membered heterocycloalkyl; which is optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl- or —C(═O)$NR^6R^7$;

$R^5$ represents a hydrogen atom, a $C_1$-$C_6$-alkyl- or $C_3$-$C_6$-cycloalkyl-group;

$R^6$ represents a hydrogen atom, a $C_1$-$C_6$-alkyl- or $C_3$-$C_6$-cycloalkyl-group;

$R^7$ represents a hydrogen atom, a $C_1$-$C_6$-alkyl- or $C_3$-$C_6$-cycloalkyl-group; or $NR^6R^7$ together represent a 3- to 10-membered heterocycloalkyl group;

$R^8$ represents halo-, hydroxy-, oxo-(O═), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —C(═O)$R^5$, —C(═O)O—$R^5$, —OC(═O)—$R^5$, —N(H)C(═O)$R^5$, —N($R^4$)C(═O)$R^5$, —N(H)C(═O)$NR^5R^4$, —N($R^4$)C(═O)$NR^5R^4$, —N(H)$R^5$, —$NR^5R^4$, —C(═O)N(H)$R^5$, —C(═O)$NR^5R^4$, $R^4$—S—, $R^4$—S(═O)—, $R^4$—S(═O)$_2$—, —N(H)S(═O)$R^4$, —N($R^4$)S(═O)$R^4$, —S(═O)N(H)$R^5$, —S(═O)$NR^5R^4$, —N(H)S(═O)$_2R^4$, —N($R^4$)S(═O)$_2R^4$, —S(═O)$_2$N(H)$R^5$, —S(═O)$_2$ $NR^5R^4$, —S(═O)(═$NR^5$)$R^4$, —S(═O)(═$NR^4$)$R^5$ or —N═S(═O)($R^5$)$R^4$;

p represents an integer of 1 or 2;

q represents an integer of 1, 2 or 3;

or a tautomer, an N-oxide, a hydrate, a solvate, or a salt thereof, or a mixture of same.

In another preferred embodiment, the invention relates to compounds of formula Ia:

Ia

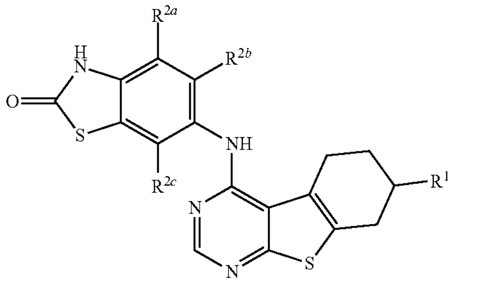

in which:

$R^1$ represents a group selected from: —C(═O)N(H)$R^3$, —C(═O)$NR^3R^4$;

$R^{2a}$ represents a hydrogen atom;

$R^{2b}$ represents a hydrogen atom or $C_1$-$C_3$-alkoxy-group; preferably a methoxy-group;

$R^{2c}$ represents a hydrogen atom;

$R^3$ represents a $C_1$-$C_6$-alkyl-group;

$R^4$ represents a $C_1$-$C_6$-alkyl-group;

or a tautomer, an N-oxide, a hydrate, a solvate, or a salt thereof, or a mixture of same.

It is to be understood that the present invention relates to any sub-combination within any embodiment or aspect of the present invention of compounds of general formula I, supra.

More particularly still, the present invention covers compounds of general formula I which are disclosed in the Examples section of this text, infra.

In accordance with another aspect, the present invention covers methods of preparing compounds of the present invention, said methods comprising the steps as described in the Experimental Section herein.

In a preferred embodiment, the present invention relates to a method of preparing compounds of general formula I, supra, in which method an intermediate compound of general formula II:

II

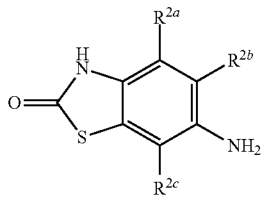

in which $R^{2a}$, $R^{2b}$, and $R^{2c}$ are as defined for the compounds of general formula I, supra, is allowed to react with an intermediate compound of general formula III:

III

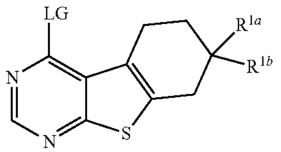

in which $R^{1a}$ and $R^{1b}$ are as defined for the compounds of general formula I, supra, and LG represents a leaving group (as defined hereinafter), such as a halogen atom or a trifluoromethylsulphonyloxy or nonafluorobutylsulphonyloxy group for example, thus providing a compound of general formula I:

I

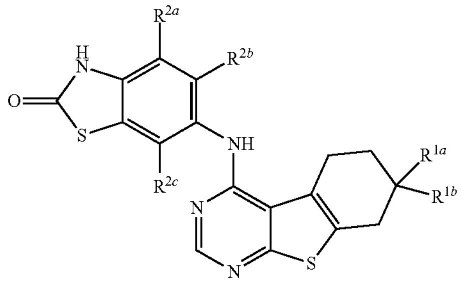

in which $R^{1a}$, $R^{1b}$, $R^{2a}$, $R^{2b}$, and $R^{2c}$ are as defined for the compounds of general formula I, supra.

As used herein, the term "leaving group" refers to an atom or a group of atoms that is displaced in a chemical reaction as stable species taking with it the bonding electrons. Preferably, a leaving group is selected from the group comprising: halo, in particular chloro, bromo or iodo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tertbutyl-benzene)sulfonyloxy, benzenesulfonyloxy, and (4-methoxy-benzene)sulfonyloxy.

In accordance with a further aspect, the present invention covers intermediate compounds which are useful in the preparation of compounds of the present invention of general formula I, particularly in the method described herein. In particular, the present invention covers compounds of general formula III:

III

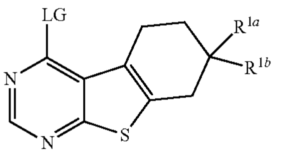

in which $R^{1a}$ and $R^{1b}$ are as defined for the compounds of general formula I, supra, and LG represents a leaving group, such as a halogen atom or a trifluoromethylsulphonyloxy or nonafluorobutylsulphonyloxy group for example.

In accordance with yet another aspect, the present invention covers the use of the intermediate compounds of general formula II and/or III:

II

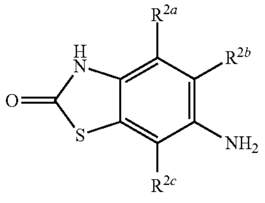

III

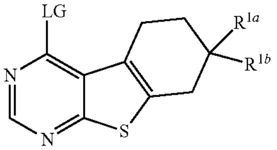

in which $R^{1a}$, $R^{1b}$, $R^{2a}$, $R^{2b}$, and $R^{2c}$ are as defined for the compounds of general formula I, supra, and LG represents a leaving group, such as a halogen atom or a trifluoromethylsulphonyloxy or nonafluorobutylsulphonyloxy group for example;

for the preparation of a compound of general formula I as defined supra.

Synthesis of Compounds of General Formula I of the Present Invention

Compounds of general formula II, III and IV can be synthesized according to the procedure depicted in Scheme 1, wherein $R^{1a}$, $R^{1b}$, $R^{2a}$, $R^{2b}$, and $R^{2c}$ are as defined for the compounds of general formula I, supra, and LG represents a leaving group:

Scheme 1

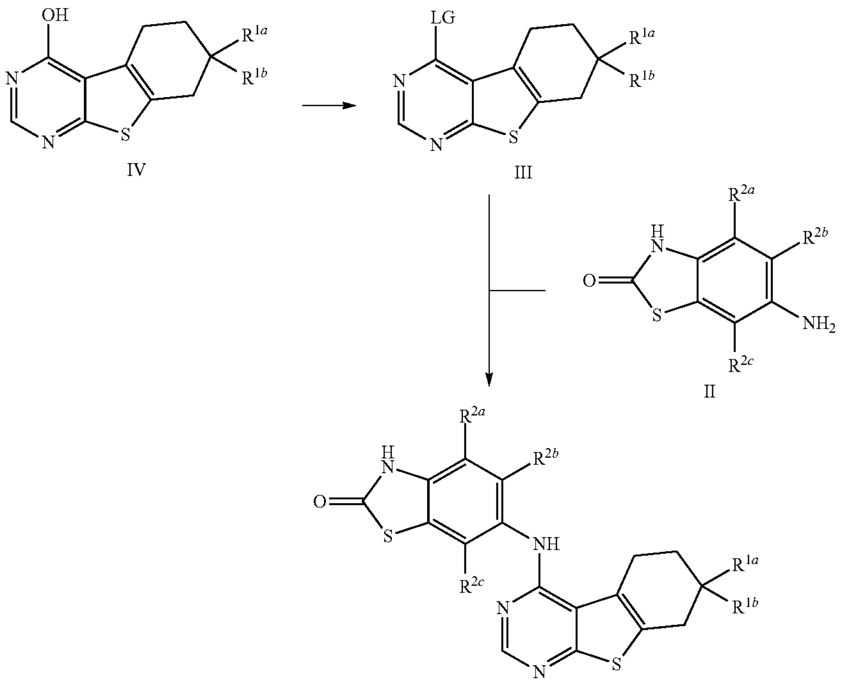

IV

III

II

I

Scheme 1 exemplifies the main route that allows variations in $R^{1a}$, $R^{1b}$, $R^{2a}$, $R^{2b}$, or $R^{2c}$ at different stages of the synthesis. However, also other routes may be used to synthesise the target compounds, in accordance with common general knowledge of a person skilled in the art of organic synthesis. The order of transformations exemplified in the Scheme is therefore not intended to be limiting. In addition, interconversion of any of the substituents, $R^{1a}$, $R^{1b}$, $R^{2a}$, $R^{2b}$, or $R^{2c}$ can be achieved before and/or after the exemplified transformations.

These modifications can be such as the introduction of protecting groups, cleavage of protecting groups, reduction or oxidation of functional groups, halogenation, metallation, substitution or other reactions known to a person skilled in the art. These transformations include those which introduce a functionality which allows for further interconversion of substituents. Appropriate protecting groups and their introduction and cleavage are well-known to a person skilled in the art (see for example T. W. Greene and P. G. M. Wuts in Protective Groups in Organic Synthesis, 3rd edition, Wiley 1999). Specific examples are described in the subsequent paragraphs. Further, it is possible that two or more successive steps may be performed without work-up being performed between said steps, e.g. a "one-pot" reaction, as it is well-known to a person skilled in the art.

Compounds of formula IV may be commercially available or can be synthesized according to procedures known to a person skilled in the art, for example applying procedures described in WO2005/010008.

Compounds of formula III in which LG represents a leaving group like, for example, a halogen atom as, for example, a chlorine or bromine atom are obtained from compounds of formula IV by reacting the alcohol with a halogenation agent like, for example, phosphorus trichloride or phosphorus tribromide with or without an additional inert solvent as, for example, toluene at temperatures ranging from room temperature to the boiling point of the solvent, for example.

Compounds of formula III in which LG represents a leaving group like, for example, an alkylsulfonate as, for example, methanesulfonate or trifluoromethanesulfonate or 1,1,2,2,3,3,4,4,4-nonafluorobutane-1-sulfonate or an arylsulfonate like, for example, benzenesulfonate or 4-methylbenzenesulfonate are obtained from compounds of formula IV by reacting the alcohol with a suitable alkylsulfonate as, for example, methanesulfonyl chloride or trifluoromethanesulfonyl chloride or 1,1,2,2,3,3,4,4,4-nonafluorobutane-1-sulfonyl fluoride or by reacting the alcohol with a suitable arylsulfonate as, for example, benzenesulfonyl chloride or 4-methylbenzenesulfonyl chloride in an inert solvent like, for example, tetrahydrofuran or toluene or dichloromethane optionally in the presence of a suitable base like, for example, triethylamine or pyridine or N,N-dimethylpyridin-4-amine at temperatures ranging from −40° C. to the boiling point of the solvent, for example.

Compounds of general formula III can be reacted with amines of formula II optionally in the presence of acid like, for example, hydrochloric acid in an inert solvent like, for example, ethanol or 1,4-dioxane at temperatures ranging from room temperature to the boiling point of the solvent, for example, to give compounds of general formula I.

Compounds of general formula I can also be build by Ullmann-type coupling reactions in the presence of suitable catalysts, such as, for example, copper based catalysts like copper(II)diacetate or copper(I)chloride in the presence of a suitable base, like for example, caesium carbonate starting from compounds of general formula III. Optionally, suitable ligands like N,N-dimethylglycine or phenyl hydrogen pyrrolidin-2-ylphosphonate can be added. The reaction can be performed at temperatures ranging from −40° C. to the boiling point of the solvent, for example.

Compounds of formula II may be commercially available or can be synthesized according to procedures known to a person skilled in the art, for example adapting procedures described in WO2011/137046.

Further, the compounds of formula I of the present invention can be converted to any salt as described herein, by any method which is known to the person skilled in the art. Similarly, any salt of a compound of formula I of the present invention can be converted into the free compound, by any method which is known to the person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallisation. In some cases, impurities may be removed by stirring using a suitable solvent. In some cases, the compounds may be purified by chromatography, particularly flash chromatography, using for example pre-packed silica gel cartridges, e.g. from Separtis such as Isolute® Flash silica gel or Isolute® Flash NH2 silica gel in combination with a suitable chromatographic system such as an Isolera system (Biotage) and eluents such as, for example, gradients of hexane/ethyl acetate or dichloromethane/methanol. In some cases, the compounds may be purified by preparative HPLC using, for example, a Waters autopurifier equipped with a diode array detector and/or on-line electrospray ionisation mass spectrometer in combination with a suitable pre-packed reverse phase column and eluants such as, for example, gradients of water and acetonitrile which may contain additives such as trifluoroacetic acid, formic acid or aqueous ammonia.

EXAMPLES

Example 1

(RS)-Ethyl 4-[(2-oxo-2,3-dihydro-1,3-benzothiazol-6-yl)amino]-5,6,7,8-tetrahydro[1]benzothieno[2,3-d]pyrimidine-7-carboxylate

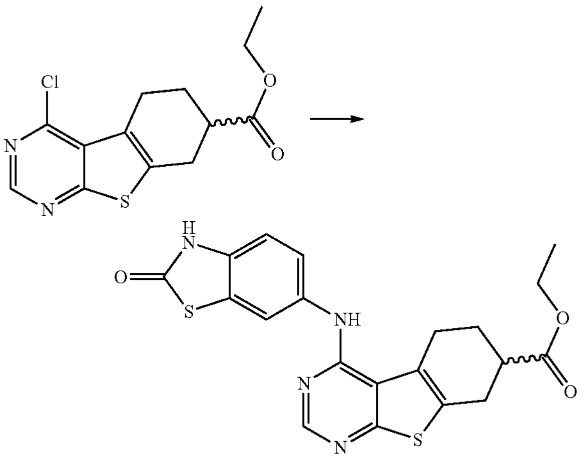

A mixture comprising 1.00 g (3.37 mmol) (RS)-ethyl 4-chloro-5,6,7,8-tetrahydro[1]benzothieno[2,3-d]pyrimidine-7-carboxylate which was prepared according to intermediate example 1a, 840 mg 6-amino-1,3-benzothiazol-2(3H)-one, 9.54 mL ethanol and 182 μL hydrochloric acid (4M in dioxane) was reacted at 100° C. for 5 hours. The precipitate was washed with ethanol and diethyl ether and digested with hydrochloric acid (1M). After filtration the solid was washed with water, propan-2-ol, diethyl ether and dried to give 1.24 g (76%) of the title compound as hydrochloride.

$^1$H-NMR (DMSO-d6): δ=1.18 (3H), 1.90 (1H), 2.17 (1H), 2.86-3.22 (5H), 4.09 (2H), 7.10 (1H), 7.40 (1H), 7.77 (1H), 8.36 (1H), 8.45 (1H), 11.91 (1H) ppm.

Example 1a

(RS)-Ethyl 4-chloro-5,6,7,8-tetrahydro[1]benzothieno[2,3-d]pyrimidine-7-carboxylate which was prepared according to intermediate example

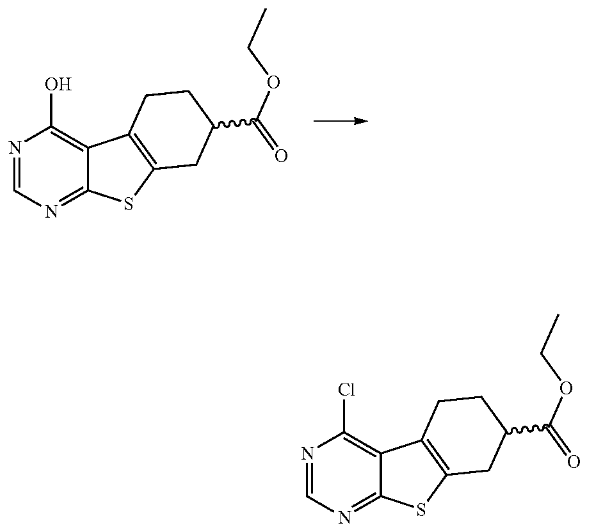

A mixture comprising 195 g (700.6 mmol) (RS)-ethyl 4-hydroxy-5,6,7,8-tetrahydro[1]benzothieno[2,3-d]pyrimidine-7-carboxylate which was prepared according to WO2005/10008, 1.92 L toluene, 195 mL N-ethyl-N-isopropylpropan-2-amine and 78.4 mL phosphorus oxychloride was heated at 80° C. overnight. The mixture was poured into sodium hydrogencarbonate solution and extracted with ethyl acetate. The organic layer was washed with brine and dried over sodium sulphate. A filtration and removal of the solvent the residue was crystallized from diisopropyl ether to give 120 g (58%) of the title compound.

Example 2

(RS)-4-[(2-Oxo-2,3-dihydro-1,3-benzothiazol-6-yl)amino]-5,6,7,8-tetrahydro[1]benzothieno[2,3-d]pyrimidine-7-carboxylic acid

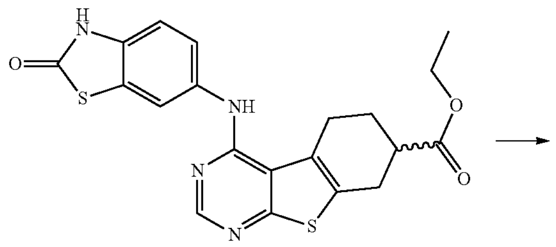

-continued

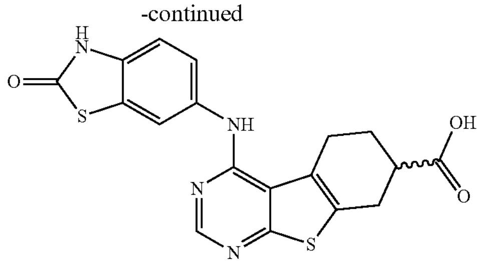

A mixture comprising 1.24 g (2.91 mmol) (RS)-ethyl 4-[(2-oxo-2,3-dihydro-1,3-benzothiazol-6-yl)amino]-5,6,7,8-tetrahydro[1]benzothieno[2,3-d]pyrimidine-7-carboxylate which was prepared according to example 1, 17.4 mL lithium hydroxide solution (1M in water), 50.3 mL tetrahydrofuran and 13.5 mL methanol was stirred at 23° C. overnight. Hydrochloric acid was added and the solvents were removed. The residue was washed with water, propan-2-ol, diethyl ether and dried to give 1.21 g (96%) of the title compound as hydrochloride.

$^1$H-NMR (DMSO-d6): δ=1.88 (1H), 2.16 (1H), 2.81 (1H), 2.91-3.24 (4H), 7.07 (1H), 7.42 (1H), 7.79 (1H), 8.15 (1H), 8.30 (1H), 11.81 (1H), 12.42 (1H) ppm.

Example 3

(RS)—N-Ethyl-4-[(2-oxo-2,3-dihydro-1,3-benzothiazol-6-yl)amino]-5,6,7,8-tetrahydro[1]benzothieno[2,3-d]pyrimidine-7-carboxamide

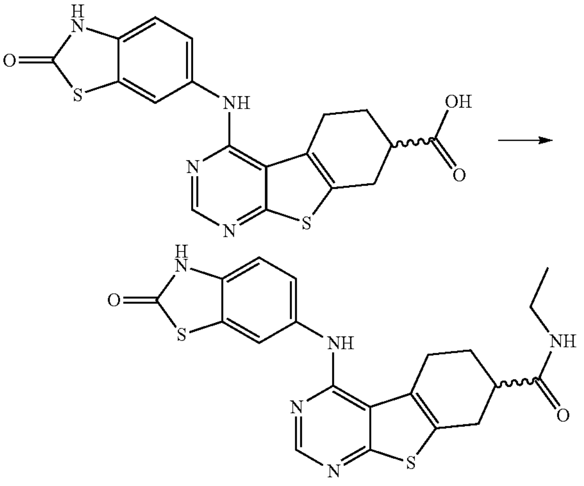

A mixture comprising 150 mg (376 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid which was prepared according to example 2, 4.2 mL N,N-dimethylformamide, 565 μL ethanamine solution (2M in tetrahydrofuran), 224 μL 2,4,6-tripropyl-1,3,5,2,4,6-trioxatriphosphinane 2,4,6-trioxide solution (50% in ethyl acetate) and 197 μL N-ethyl-N-isopropylpropan-2-amine was stirred at 23° C. overnight. Water and dichloromethane were added, the precipitate filtered off, washed with water, propan-2-ol and dried to give 94.9 mg (56%) of the title compound.

$^1$H-NMR (DMSO-d6): δ=1.01 (3H), 1.77 (1H), 2.04 (1H), 2.59 (1H), 2.89 (2H), 3.00-3.13 (3H), 3.20 (1H), 7.07 (1H), 7.41 (1H), 7.79 (1H), 7.94 (1H), 8.14 (1H), 8.30 (1H), 11.80 (1H) ppm.

Example 4

(RS)—N-Cyclopropyl-4-[(2-oxo-2,3-dihydro-1,3-benzothiazol-6-yl)amino]-5,6,7,8-tetrahydro[1]benzothieno[2,3-d]pyrimidine-7-carboxamide

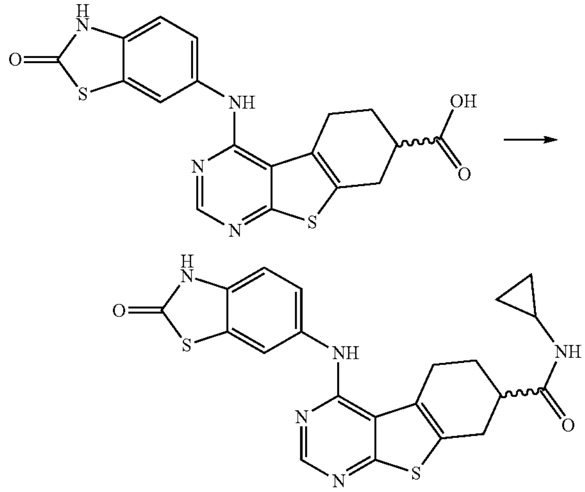

150 mg (376 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid which was prepared according to example 2 were transformed in analogy to example 3 using cyclopropanamine to give after working up and purification 126.7 mg (73%) of the title compound.

$^1$H-NMR (DMSO-d6): δ=0.39 (2H), 0.59 (2H), 1.76 (1H), 2.02 (1H), 2.54 (1H), 2.63 (1H), 2.88 (2H), 3.05 (1H), 3.19 (1H), 7.06 (1H), 7.41 (1H), 7.78 (1H), 8.00 (1H), 8.13 (1H), 8.229 (1H), 11.82 (1H) ppm.

Example 5

(RS)—N-Isopropyl-4-[(2-oxo-2,3-dihydro-1,3-benzothiazol-6-yl)amino]-5,6,7,8-tetrahydro[1]benzothieno[2,3-d]pyrimidine-7-carboxamide

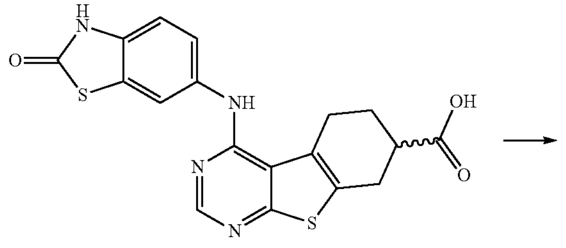

-continued

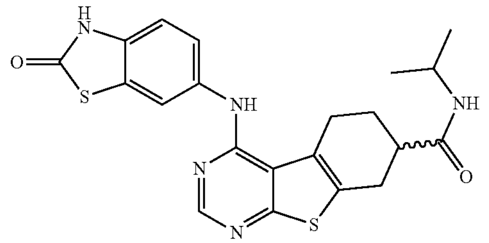

150 mg (376 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid which was prepared according to example 2 were transformed in analogy to example 3 using propan-2-amine to give after working up and purification 65 mg (37%) of the title compound.

$^1$H-NMR (DMSO-d6): δ=1.05 (6H), 1.76 (1H), 2.02 (1H), 2.57 (1H), 2.88 (2H), 3.05 (1H), 3.20 (1H), 3.84 (1H), 7.05 (1H), 7.38 (1H), 7.75 (1H), 7.80 (1H), 8.12 (1H), 8.29 (1H), 11.79 (1H) ppm.

Example 6

(RS)—N-Isobutyl-4-[(2-oxo-2,3-dihydro-1,3-benzothiazol-6-yl)amino]-5,6,7,8-tetrahydro[1]benzothieno[2,3-d]pyrimidine-7-carboxamide

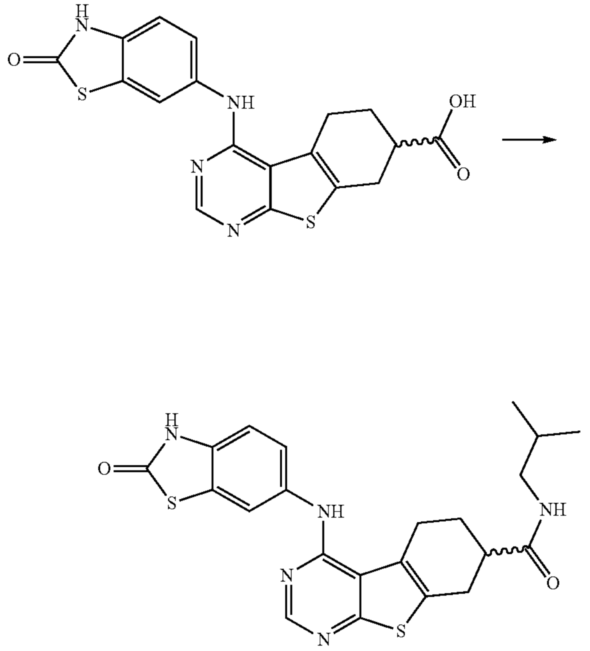

62 mg (156 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid which was prepared according to example 2 were transformed in analogy to example 3 using 2-methylpropan-1-amine to give after working up and purification 50.7 mg (68%) of the title compound.

$^1$H-NMR (DMSO-d6): δ=0.85 (6H), 1.65-1.90 (2H), 2.07 (1H), 2.67 (1H), 2.88-2.97 (4H), 3.04-3.23 (2H), 7.09 (1H), 7.43 (1H), 7.80 (1H), 7.97 (1H), 8.15 (1H), 8.32 (1H), 11.83 (1H) ppm.

Example 7

(RS)-4-[(2-Oxo-2,3-dihydro-1,3-benzothiazol-6-yl)amino]-N-(3,3,3-trifluoropropyl)-5,6,7,8-tetrahydro[1]benzothieno[2,3-d]pyrimidine-7-carboxamide

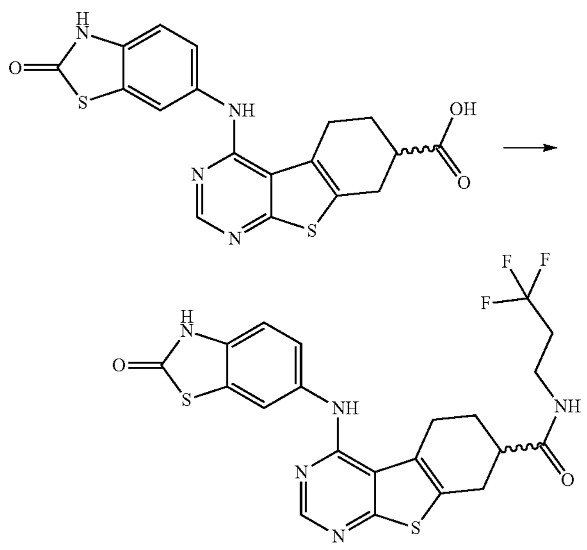

62 mg (156 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid which was prepared according to example 2 were transformed in analogy to example 3 using 3,3,3-trifluoropropan-1-amine to give after working up and purification 47.7 mg (59%) of the title compound.

$^1$H-NMR (DMSO-d6): δ=1.80 (1H), 2.07 (1H), 2.44 (2H), 2.65 (1H), 2.93 (2H), 3.10 (1H), 3.23 (1H), 3.35 (2H), 7.09 (1H), 7.44 (1H), 7.81 (1H), 8.16 (1H), 8.24 (1H), 8.332 (1H), 11.78 (1H) ppm.

Example 8

(RS)-4-[(2-Oxo-2,3-dihydro-1,3-benzothiazol-6-yl)amino]-N-phenyl-5,6,7,8-tetrahydro[1]benzothieno[2,3-d]pyrimidine-7-carboxamide

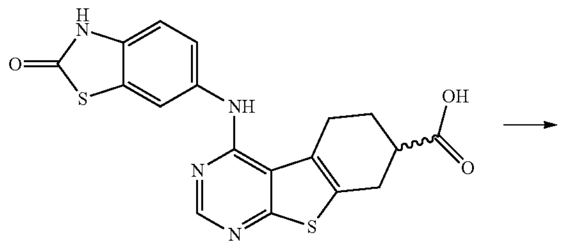

-continued

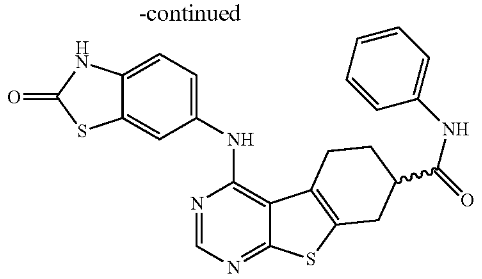

42 mg (156 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid which was prepared according to example 2 were transformed in analogy to example 3 using aniline to give after working up and purification 44.5 mg (57%) of the title compound.

$^1$H-NMR (DMSO-d6): δ=1.91 (1H), 2.21 (1H), 2.92 (1H), 2.99-3.22 (3H), 3.28 (1H), 7.04 (1H), 7.11 (1H), 7.30 (2H), 7.46 (1H), 7.65 (2H), 7.83 (1H), 8.22 (1H), 8.34 (1H), 10.15 (1H), 11.87 (1H) ppm.

Example 9

(RS)—N-Benzyl-4-[(2-oxo-2,3-dihydro-1,3-benzothiazol-6-yl)amino]-5,6,7,8-tetrahydro[1]benzothieno[2,3-d]pyrimidine-7-carboxamide

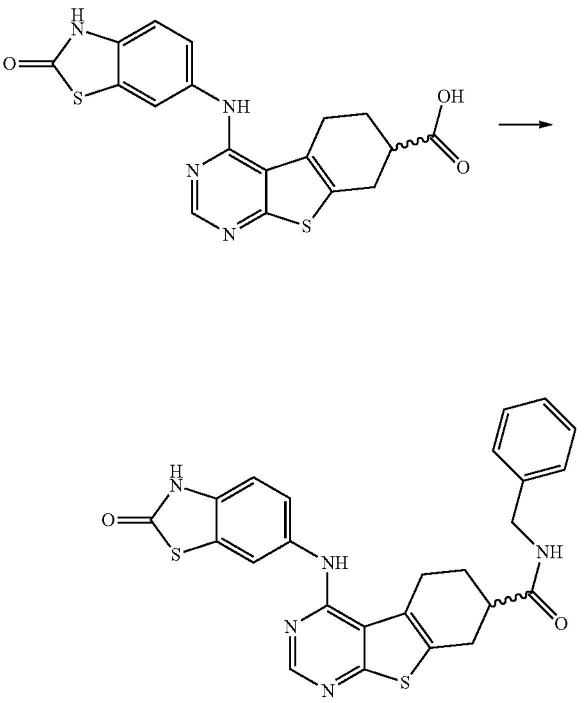

62 mg (156 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid which was prepared according to example 2 were transformed in analogy to example 3 using 1-phenylmethanamine to give after working up and purification 53.3 mg (67%) of the title compound.

$^1$H-NMR (DMSO-d6): δ=1.85 (1H), 2.12 (1H), 2.74 (1H), 2.98 (2H), 3.12 (1H), 3.23 (1H), 4.32 (2H), 7.09 (1H), 7.21-7.35 (5H), 7.43 (1H), 7.81 (1H), 8.16 (1H), 8.33 (1H), 8.52 (1H), 11.63 (1H) ppm.

Example 10

(RS)-4-[(2-Oxo-2,3-dihydro-1,3-benzothiazol-6-yl)amino]-N-[3-(trifluoromethyl)benzyl]-5,6,7,8-tetrahydro[1]benzothieno[2,3-d]pyrimidine-7-carboxamide

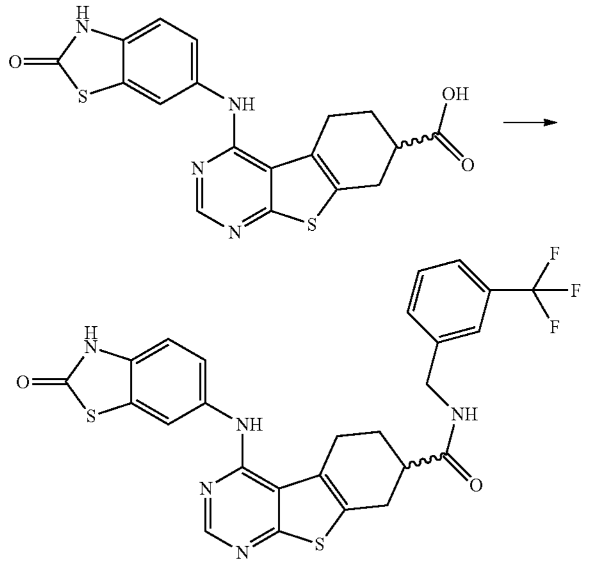

62 mg (156 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid which was prepared according to example 2 were transformed in analogy to example 3 using 1-[3-(trifluoromethyl)phenyl]methanamine to give after working up and purification 54.5 mg (60%) of the title compound.

$^1$H-NMR (DMSO-d6): δ=1.86 (1H), 2.12 (1H), 2.75 (1H), 2.99 (2H), 3.12 (1H), 3.23 (1H), 4.41 (2H), 7.09 (1H), 7.44 (1H), 7.54-7.64 (4H), 7.81 (1H), 8.16 (1H), 8.33 (1H), 8.64 (1H), 11.66 (1H) ppm.

Example 11

(RS)—N-Methyl-4-[(2-oxo-2,3-dihydro-1,3-benzothiazol-6-yl)amino]-5,6,7,8-tetrahydro[1]benzothieno[2,3-d]pyrimidine-7-carboxamide

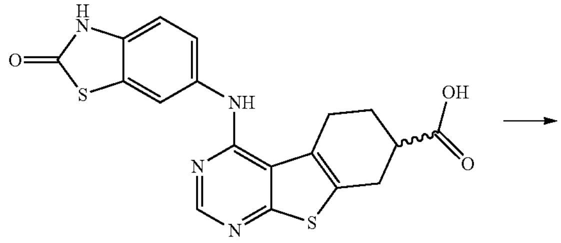

-continued

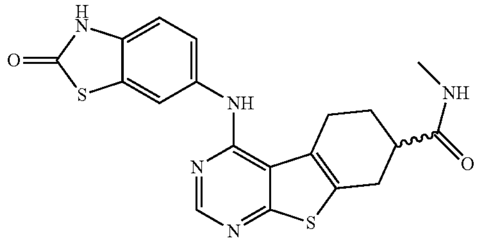

62 mg (156 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid which was prepared according to example 2 were transformed in analogy to example 3 using methanamine to give after working up and purification 57.1 mg (85%) of the title compound.

$^1$H-NMR (DMSO-d6): δ=1.78 (1H), 2.03 (1H), 2.58 (3H), 2.62 (2H), 2.89 (1H), 3.08 (1H), 3.19 (1H), 7.04 (1H), 7.36 (1H), 7.74 (1H), 7.97 (1H), 8.13 (1H), 8.28 (1H) ppm.

Example 12

(RS)—N-(Cyclopropylmethyl)-4-[(2-oxo-2,3-dihydro-1,3-benzothiazol-6-yl)amino]-5,6,7,8-tetrahydro[1]benzothieno[2,3-d]pyrimidine-7-carboxamide

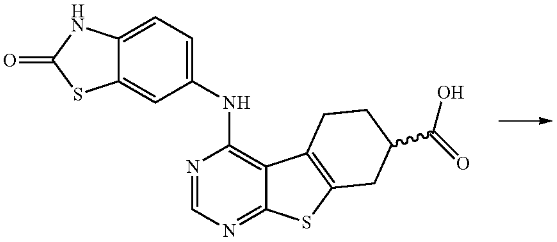

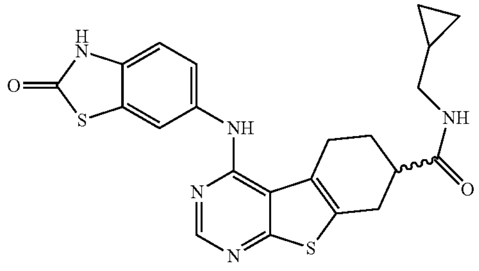

62 mg (156 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid which was prepared according to example 2 were transformed in analogy to example 3 using 1-cyclopropylmethanamine to give after working up and purification 41.9 mg (57%) of the title compound.

$^1$H-NMR (DMSO-d6): δ=0.13 (2H), 0.38 (2H), 0.88 (1H), 1.77 (1H), 2.04 (1H), 2.63 (1H), 2.85-3.22 (6H), 7.05 (1H), 7.37 (1H), 7.75 (1H), 8.06 (1H), 8.13 (1H), 8.29 (1H), 11.84 (1H) ppm.

Example 13

(RS)—N,N-Dimethyl-4-[(2-oxo-2,3-dihydro-1,3-benzothiazol-6-yl)amino]-5,6,7,8-tetrahydro[1]benzothieno[2,3-d]pyrimidine-7-carboxamide

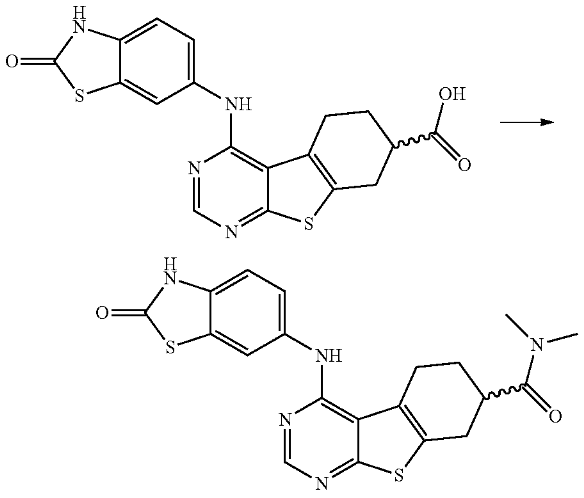

62 mg (156 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid which was prepared according to example 2 were transformed in analogy to example 3 using N-methylmethanamine to give after working up and purification 24.0 mg (34%) of the title compound.

$^1$H-NMR (DMSO-d6): δ=1.72 (1H), 2.02 (1H), 2.84 (3H), 2.88 (2H), 3.05 (3H), 3.08-3.22 (3H), 7.06 (1H), 7.41 (1H), 7.79 (1H), 8.14 (1H), 8.30 (1H), 11.83 (1H) ppm.

Example 14

(RS)—N-(3-Fluorobenzyl)-4-[(2-oxo-2,3-dihydro-1,3-benzothiazol-6-yl)amino]-5,6,7,8-tetrahydro[1]benzothieno[2,3-d]pyrimidine-7-carboxamide

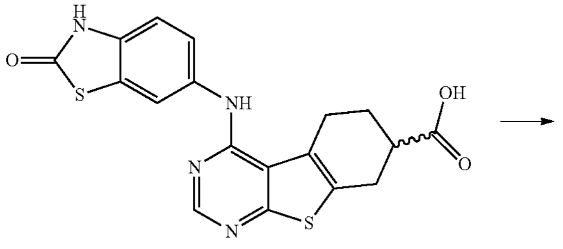

-continued

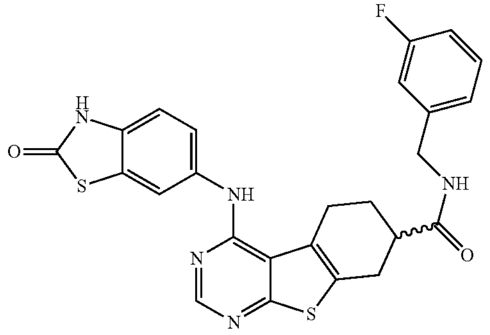

62 mg (156 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid which was prepared according to example 2 were transformed in analogy to example 3 using 1-(3-fluorophenyl)methanamine to give after working up and purification 15.5 mg (20%) of the title compound.

$^1$H-NMR (DMSO-d6): δ=1.84 (1H), 2.10 (1H), 2.68-2.81 (2H), 2.96 (2H), 3.10 (1H), 3.23 (1H), 4.31 (2H), 7.01-7.10 (4H), 7.34 (1H), 7.42 (1H), 7.80 (1H), 8.15 (1H), 8.30 (1H), 8.55 (1H) ppm.

Example 15

(RS)-4-[(2-oxo-2,3-dihydro-1,3-benzothiazol-6-yl)amino]-N-(2,2,2-trifluoroethyl)-5,6,7,8-tetrahydro[1]benzothieno[2,3-d]pyrimidine-7-carboxamide

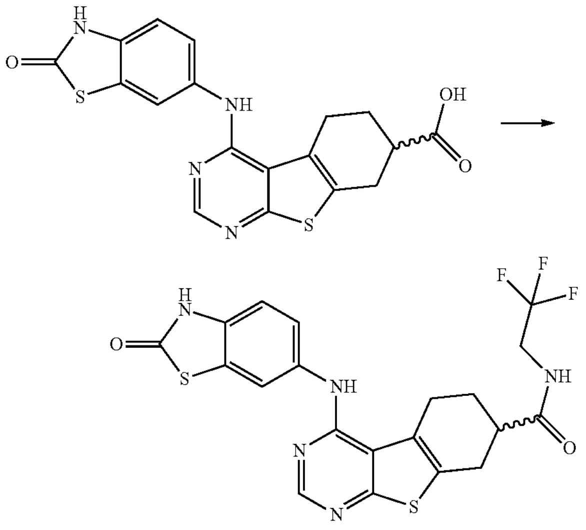

62 mg (151 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid which was prepared according to example 2 were transformed in analogy to example 3 using 2,2,2-trifluoroethanamine to give after working up and purification 61.2 mg (81%) of the title compound.

$^1$H-NMR (DMSO-d6): δ=1.80 (1H), 2.07 (1H), 2.75 (1H), 2.86-2.98 (2H), 3.04-3.21 (2H), 3.92 (2H), 7.07 (1H), 7.40 (1H), 7.77 (1H), 8.16 (1H), 8.30 (1H), 8.70 (1H), 11.78 (1H) ppm.

Example 16

(RS)-6-{[7-Methoxy-7-(methoxymethyl)-5,6,7,8-tetrahydro[1]benzothieno[2,3-d]pyrimidin-4-yl]amino}-1,3-benzothiazol-2(3H)-one

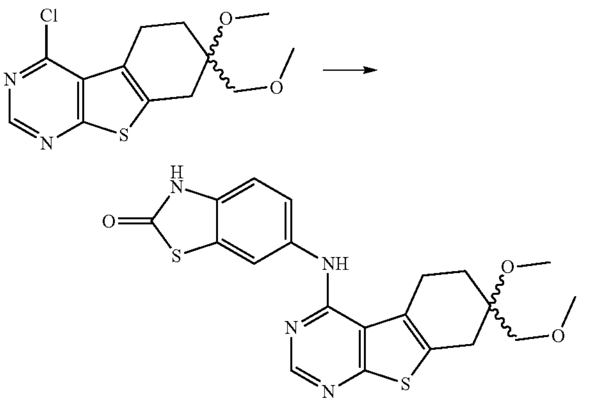

41 mg (234 μmol) (RS)-4-chloro-7-methoxy-7-(methoxymethyl)-5,6,7,8-tetrahydro[1]benzothieno[2,3-d]pyrimidine (prepared according to intermediate example 16a) were transformed in analogy to example 1 to give after working up and purification 19.2 mg (19%) of the title compound.

$^1$H-NMR (DMSO-d6): δ=1.78 (1H), 2.01 (1H), 2.82 (1H), 2.90 (1H), 3.06 (2H), 3.16 (3H), 3.28 (3H), 3.41-3.48 (2H), 7.07 (1H), 7.43 (1H), 7.80 (1H), 8.28 (1H) ppm.

Example 16a

(RS)-4-Chloro-7-methoxy-7-(methoxymethyl)-5,6,7,8-tetrahydro[1]benzothieno[2,3-d]pyrimidine

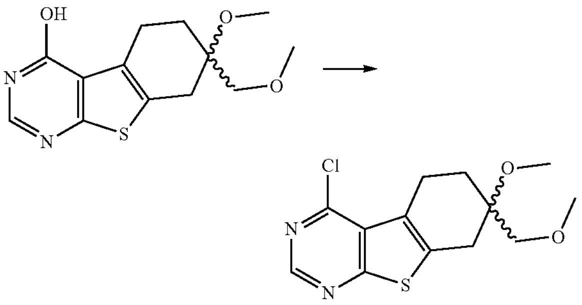

16.8 g (59.9 mmol) (RS)-7-methoxy-7-(methoxymethyl)-5,6,7,8-tetrahydro[1]benzothieno[2,3-d]pyrimidin-4-ol (prepared according to intermediate example 16b) were transformed in analogy to intermediate example 1a to give after working up and purification 15.5 mg (87%) of the title compound.

Example 16b

(RS)-7-Methoxy-7-(methoxymethyl)-5,6,7,8-tetrahydro[1]benzothieno[2,3-d]pyrimidin-4-ol

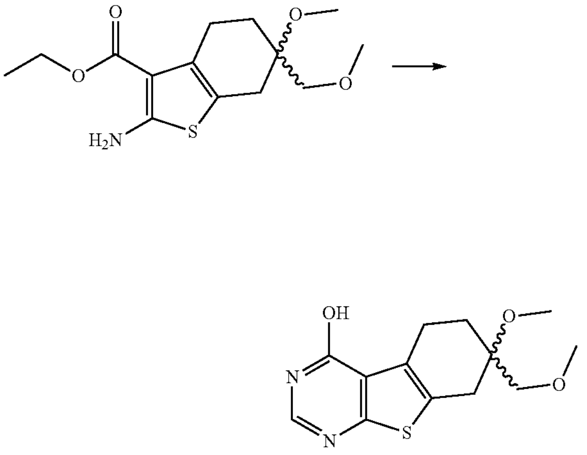

A mixture comprising 21.46 g (71.7 mmol) (RS)-ethyl 2-amino-6-methoxy-6-(methoxymethyl)-4,5,6,7-tetrahydro-1-benzothiophene-3-carboxylate (prepared according to intermediate example 16c), 114 mL methanamide and 7.23 g ammonium formate was stirred at 150° C. overnight. The reaction mixture was cooled in an ice bath, the precipitate was filtered off, washed with water and ethanol and dried to give 16.95 g (84%) of the title compound.

Example 16c

(RS)-Ethyl 2-amino-6-methoxy-6-(methoxymethyl)-4,5,6,7-tetrahydro-1-benzothiophene-3-carboxylate

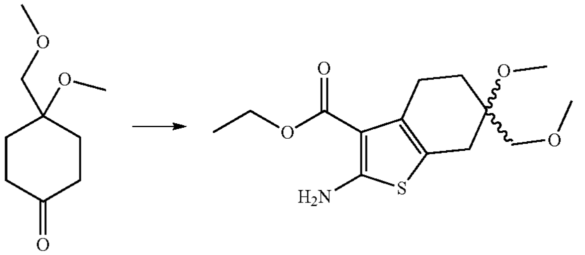

A mixture comprising 30 g (174 mmol) 4-methoxy-4-(methoxymethyl)cyclohexanone (prepared according to intermediate example 16d), 18.6 mL ethyl cyanoacetate, 5.59 g sulfur, 15.2 mL morpholine and 375 mL ethanol was stirred at 23° C. overnight. After filtration, the solvent was removed and the residue resolved in ethyl acetate, washed with brine and dried over sodium sulfate. After filtration and removal of the solvent, the crude product was digested with diisopropyl ether at 40° C. filtered and dried to give 21.7 g (42%) of the title compound.

Example 16d

4-Methoxy-4-(methoxymethyl)cyclohexanone

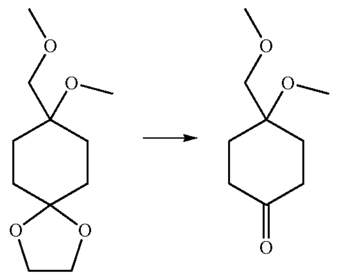

A mixture comprising 217 g (1.00 mol) 8-methoxy-8-(methoxymethyl)-1,4-dioxaspiro[4.5]decane (prepared according to intermediate example 16e), 1.7 L acetone, 0.86 L water and 30.5 g 4-methylbenzenesulfonic acid hydrate was stirred at 23° C. overnight. The acetone was removed, 0.5 L saturated aqueous sodium hydrogencarbonate added followed by 0.4 L brine. The mixture was extracted with ethyl acetate, the combined organic layers were washed with brine and dried over sodium sulfate. After filtration and removal of the solvent 180 g (max. 100%) of the title compound were obtained that was used without further purification.

Example 16e

8-Methoxy-8-(methoxymethyl)-1,4-dioxaspiro[4.5]decane

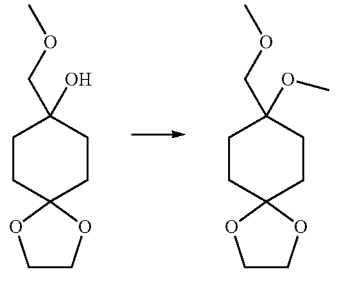

To a mixture of 82.27 g sodium hydride (80%) in 2.1 L tetrahydrofuran was slowly added the solution of 208 g (1.03 mol) 8-(methoxymethyl)-1,4-dioxaspiro[4.5]decan-8-ol (prepared according to intermediate example 16f) in 1 L tetrahydrofuran under cooling. After 0.5 hours at 23° C. 143 mL iodomethane were added and the mixture was stirred at 23° C. overnight. Water was added and the mixture was extracted with ethyl acetate. The combined organic layers were washed with brine and dried over sodium sulfate. After filtration and removal of the solvent 227.5 g (max. 100%) of the title compound were obtained that was used without further purification.

Example 16f 8-(Methoxymethyl)-1,4-dioxaspiro[4.5]decan-8-ol

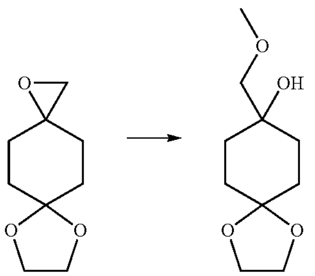

To a solution of 196 g (1.15 mol) 1,7,10-trioxadispiro[2.2.4.2]dodecane (prepared according to Synthetic Communications, 2003, vol. 33, #12, p. 2135-2144) in 2 L methanol were added 2 L sodium methanolate (25% in methanol) and the mixture was stirred at 60° C. for 8 hours. The solvent was removed, ethyl acetate added and washed with brine. The organic layer was dried over sodium sulfate. After filtration and removal of the solvent 272 g (max. 100%) of the title compound were obtained that was used without further purification.

Example 17

(RS)-6-[(7-Methyl-5,6,7,8-tetrahydro[1]benzothieno[2,3-d]pyrimidin-4-yl)amino]-1,3-benzothiazol-2(3H)-one

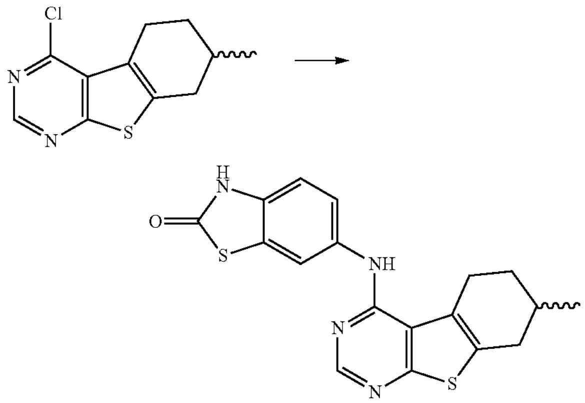

111 mg (637 μmol) (RS)-4-chloro-7-methyl-5,6,7,8-tetrahydro[1]benzothieno[2,3-d]pyrimidine (prepared according to intermediate example 17a) were transformed in analogy to example 1 to give after working up and purification 96.3 mg (39%) of the title compound.

$^1$H-NMR (DMSO-d6): δ=1.05 (3H), 1.44 (1H), 1.91 (2H), 2.38 (1H), 2.87 (1H), 3.01-3.22 (2H), 7.06 (1H), 7.42 (1H), 7.81 (1H), 8.10 (1H), 8.29 (1H), 11.81 (1H) ppm.

Example 17a (RS)-4-Chloro-7-methyl-5,6,7,8-tetrahydro[1]benzothieno[2,3-d]pyrimidine

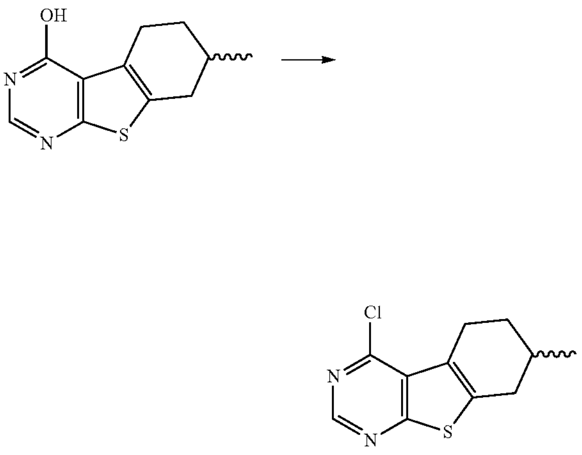

2.04 g (8.70 mmol) (RS)-7-methyl-5,6,7,8-tetrahydro[1]benzothieno[2,3-d]pyrimidin-4-ol (prepared according to intermediate example 17b) were transformed in analogy to intermediate example 1a to give after working up and purification 1.70 g (78%) of the title compound.

Example 17b (RS)-7-Methyl-5,6,7,8-tetrahydro[1]benzothieno[2,3-d]pyrimidin-4-ol

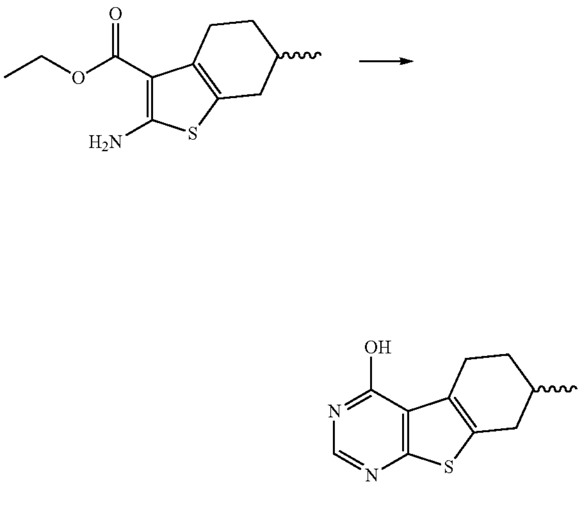

3.19 g (13.0 mmol) (RS)-ethyl 2-amino-6-methyl-4,5,6,7-tetrahydro-1-benzothiophene-3-carboxylate (prepared according to intermediate example 17c) were transformed in analogy to intermediate example 16b to give after working up and purification 2.71 g (90%) of the title compound.

Example 17c (RS)-Ethyl 2-amino-6-methyl-4,5,6,7-tetrahydro-1-benzothiophene-3-carboxylate

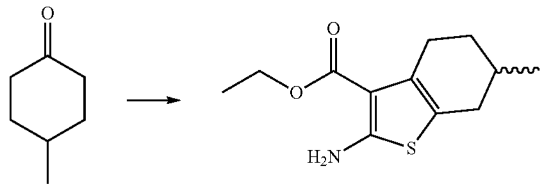

5.0 g (43.68 mmol) 4-methylcyclohexanone (CAS-No: 589-92-4) were transformed in analogy to intermediate example 16c to give after working up and purification 5.78 g (54%) of the title compound.

Example 18

(RS)-6-{[7-(Hydroxymethyl)-5,6,7,8-tetrahydro[1]benzothieno[2,3-d]pyrimidin-4-yl]amino}-1,3-benzothiazol-2(3H)-one

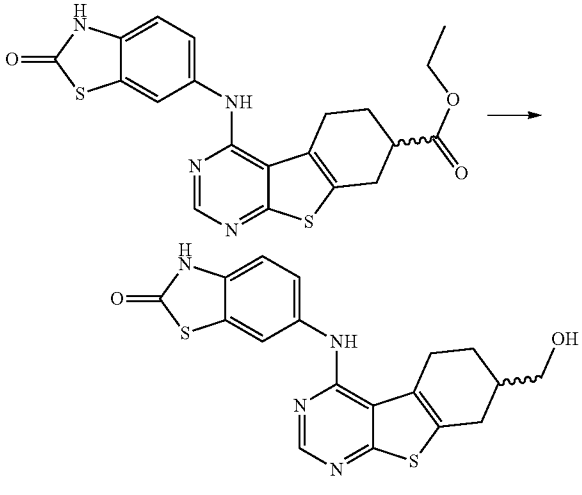

A mixture comprising 4.42 g (10.36 mmol) (RS)-ethyl 4-[(2-oxo-2,3-dihydro-1,3-benzothiazol-6-yl)amino]-5,6,7,8-tetrahydro[1]benzothieno[2,3-d]pyrimidine-7-carboxylate (prepared according to example 1) 350 mL tetrahydrofuran and 62.1 mL hydrido(diisobutyl)aluminum (1M in tetrahydrofuran) was stirred at 23° C. overnight. 40 mL saturated ammonium chloride was added carefully and stirring was continued for 0.5 hours. The precipitate was filtered off and washed with ethyl acetate. The product crystallized from the filtrate and was washed with water and a mixture of dichloromethane and methanol to give 3.13 g (79%) of the title compound.

$^1$H-NMR (DMSO-d6): δ=1.47 (1H), 1.85-2.04 (2H), 2.51 (1H), 2.86 (1H), 3.05 (1H), 3.17 (1H), 3.42 (2H), 4.63 (1H), 7.07 (1H), 7.43 (1H), 7.81 (1H), 8.10 (1H), 8.29 (1H), 11.74 (1H) ppm.

Example 19

(RS)-6-{[7-(Azidomethyl)-5,6,7,8-tetrahydro[1]benzothieno[2,3-d]pyrimidin-4-yl]amino}-1,3-benzothiazol-2(3H)-one

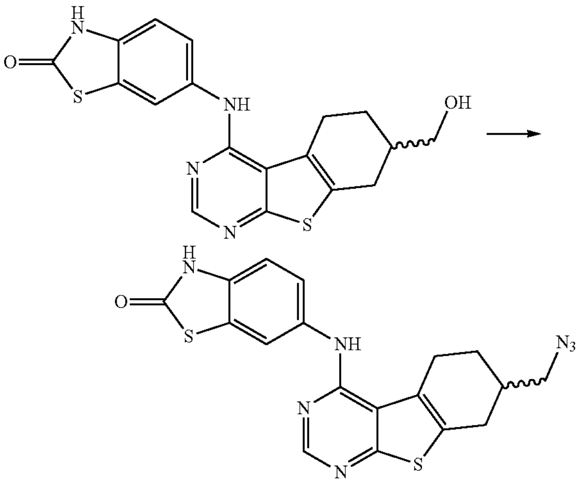

A mixture comprising 3.05 g (7.93 mmol) (RS)-6-{[7-(hydroxymethyl)-5,6,7,8-tetrahydro[1]benzothieno[2,3-d]pyrimidin-4-yl]amino}-1,3-benzothiazol-2(3H)-one (prepared according to example 18), 140 mL tetrahydrofuran, 2.91 mL diphenyl phosphorazidate and 1.66 mL 2,3,4,6,7,8,9,10-octahydropyrimido[1,2-a]azepine was heated in a pressure tube at 100° C. overnight. Water was added, the mixture extracted with ethylacetate, the combined organic layers were washed with brine and dried over sodium sulphate. After filtration and removal of the solvents, the residue was purified by crystallization from ethanol to give 2.01 g (62%) of the title compound.

$^1$H-NMR (DMSO-d6): δ=1.55 (1H), 1.95-2.13 (2H), 2.56 (1H), 2.92 (1H), 3.07 (1H), 3.20 (1H), 3.46 (2H), 7.07 (1H), 7.42 (1H), 7.80 (1H), 8.12 (1H), 8.30 (1H), 11.69 (1H) ppm.

Example 20

(RS)-6-{[7-(Aminomethyl)-5,6,7,8-tetrahydro[1]benzothieno[2,3-d]pyrimidin-4-yl]amino}-1,3-benzothiazol-2(3H)-one

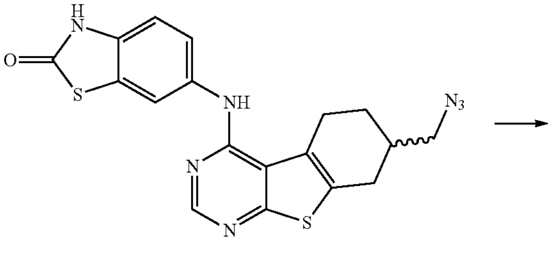

-continued

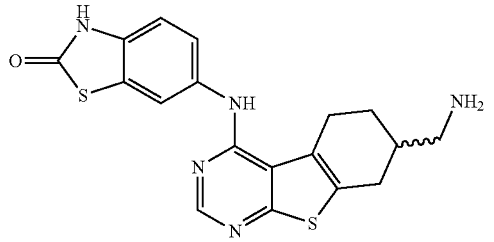

A mixture comprising 1.78 g (4.35 mmol) (RS)-6-{[7-(azidomethyl)-5,6,7,8-tetrahydro[1]benzothieno[2,3-d]pyrimidin-4-yl]amino}-1,3-benzothiazol-2(3H)-one (prepared according to example 19), 70 mL tetrahydrofuran and 2.54 g triphenylphosphine was stirred at 23° C. for 2 hours, 9.3 mL aqueous ammonia (25%) were added and stirring continued overnight. The solvents were removed and the residue was purified by chromatography to give 1.04 g (59%) of the title compound.

$^1$H-NMR (DMSO-d6): δ=1.45 (1H), 1.83 (1H), 2.01 (1H), 2.51 (1H), 2.64 (2H), 2.91 (1H), 3.03 (1H), 3.17 (1H), 7.03 (1H), 7.35 (1H), 7.73 (1H), 8.06 (1H), 8.28 (1H) ppm.

Example 21

(RS)-2-Methyl-N-({4-[(2-oxo-2,3-dihydro-1,3-benzothiazol-6-yl)amino]-5,6,7,8-tetrahydro[1]benzothieno[2,3-d]pyrimidin-7-yl}methyl)propanamide

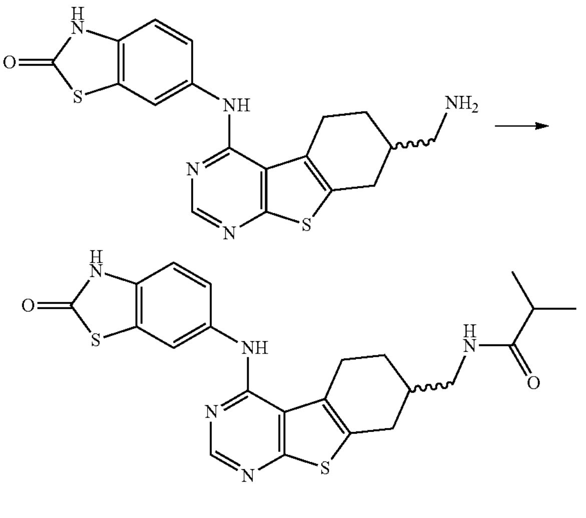

A mixture comprising 50 mg (130 μmol) (RS)-6-{[7-(aminomethyl)-5,6,7,8-tetrahydro[1]benzothieno[2,3-d]pyrimidin-4-yl]amino}-1,3-benzothiazol-2(3H)-one (prepared according to example 20), 5 mL N,N-dimethylformamide, 13.7 μL 2-methylpropanoyl chloride and 18.2 mL N,N-diethylethanamine was stirred at 23° C. overnight. Water was added and the solvents were removed. The residue was purified by chromatography to give 16 mg (26%) of the title compound.

$^1$H-NMR (DMSO-d6): δ=0.99 (6H), 1.46 (1H), 1.96-2.03 (2H), 2.37 (1H), 2.47 (1H), 2.85 (1H), 3.02-3.21 (4H), 7.06 (1H), 7.42 (1H), 7.78-7.85 (2H), 8.09 (1H), 8.30 (1H), 11.74 (1H) ppm.

Example 22

(RS)-1-({4-[(2-Oxo-2,3-dihydro-1,3-benzothiazol-6-yl)amino]-5,6,7,8-tetrahydro[1]benzothieno[2,3-d]pyrimidin-7-yl}methyl)-3-propan-2-ylurea

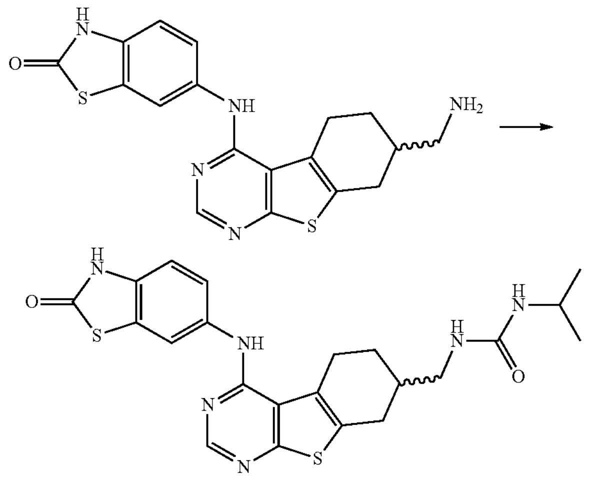

A mixture comprising 75 mg (196 μmol) (RS)-6-{[7-(aminomethyl)-5,6,7,8-tetrahydro[1]benzothieno[2,3-d]pyrimidin-4-yl]amino}-1,3-benzothiazol-2(3H)-one (prepared according to example 20), 6 mL N,N-dimethylformamide and 19.2 μL 2-isocyanatopropane was stirred at 23° C. overnight. The solvent was removed and the residue purified by chromatography to give 54 mg (56%) of the title compound.

$^1$H-NMR (DMSO-d6): δ=1.00 (6H), 1.45 (1H), 1.92 (2H), 2.46 (1H), 2.83 (1H), 2.99-3.12 (3H), 3.18 (1H), 3.63 (1H), 5.60 (1H), 5.86 (1H), 7.07 (1H), 7.42 (1H), 7.80 (1H), 8.09 (1H), 8.29 (1H), 11.72 (1H) ppm.

Example 23

(2R)-2-Hydroxy-N-({(7RS)-4-[(2-oxo-2,3-dihydro-1,3-benzothiazol-6-yl)amino]-5,6,7,8-tetrahydro[1]benzothieno[2,3-d]pyrimidin-7-yl}methyl)-3-phenylpropanamide

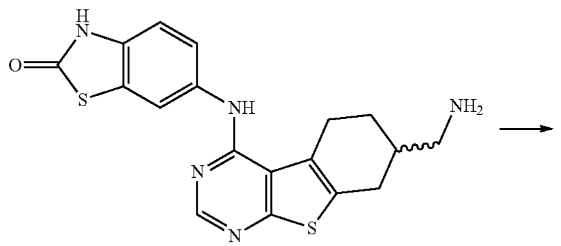

-continued

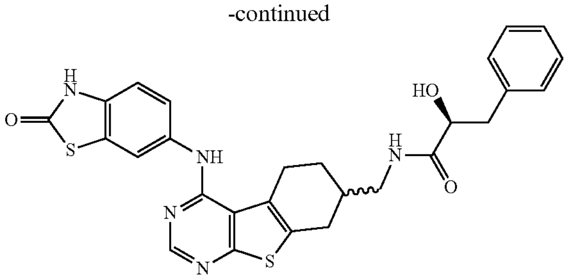

A mixture comprising 50 mg (130 μmol) (RS)-6-{[7-(aminomethyl)-5,6,7,8-tetrahydro[1]benzothieno[2,3-d]pyrimidin-4-yl]amino}-1,3-benzothiazol-2(3H)-one (prepared according to example 20), 4 mL N,N-dimethylformamide, 17.5 mg N,N-dimethylpyridin-4-amine, 21.7 mg (2S)-2-hydroxy-3-phenylpropanoic acid and 54.5 mg N-[(dimethylamino)(3H-[1,2,3]triazolo[4,5-b]pyridin-3-yloxy)methylene]-N-methylmethanaminium hexafluorophosphate was stirred at 23° C. overnight. The solvent was removed and the residue purified by chromatography to give 32 mg (45%) of the title compound.

$^1$H-NMR (DMSO-d6): δ=1.37 (1H), 1.81-2.02 (2H), 2.33 (1H), 2.58-2.81 (2H), 2.89-3.22 (5H), 4.09 (1H), 5.57 (1H), 7.07 (1H), 7.10-7.26 (5H), 7.42 (1H), 7.78-7.88 (2H), 8.10 (1H), 8.30 (1H), 11.80 (1H) ppm.

Example 24

(RS)-Propan-2-yl ({4-[(2-oxo-2,3-dihydro-1,3-benzothiazol-6-yl)amino]-5,6,7,8-tetrahydro[1]benzothieno[2,3-d]pyrimidin-7-yl}methyl)carbamate

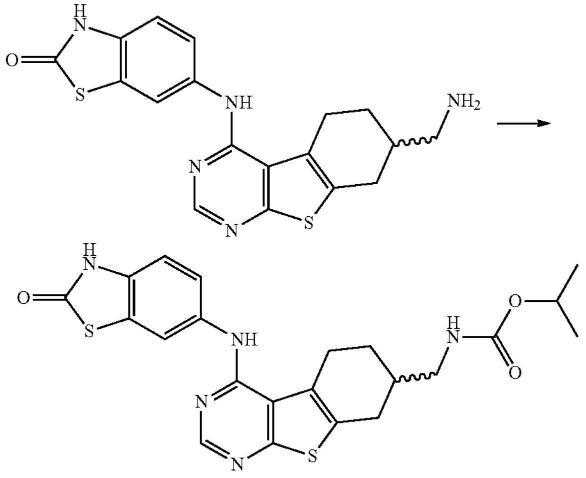

A mixture comprising 50 mg (130 μmol) (RS)-6-{[7-(aminomethyl)-5,6,7,8-tetrahydro[1]benzothieno[2,3-d]pyrimidin-4-yl]amino}-1,3-benzothiazol-2(3H)-one (prepared according to example 20), 5 mL N,N-dimethylformamide, 130 μL isopropyl carbonochloridate (1M in toluene) and 18.2 μL N,N-diethylethanamine was stirred at 23° C. overnight. Water was added, the solvents were removed and the residue purified by chromatography to give 25 mg (40%) of the title compound.

$^1$H-NMR (DMSO-d6): δ=1.14 (6H), 1.45 (1H), 1.95 (2H), 2.47 (1H), 2.85 (1H), 2.98-3.10 (3H), 3.17 (1H), 4.73 (1H), 7.07 (1H), 7.15 (1H), 7.42 (1H), 7.81 (1H), 8.09 (1H), 8.30 (1H), 11.80 (1H) ppm.

Example 25

(RS)-2-Hydroxy-2-methyl-N-({4-[(2-oxo-2,3-dihydro-1,3-benzothiazol-6-yl)amino]-5,6,7,8-tetrahydro[1]benzothieno[2,3-d]pyrimidin-7-yl}methyl)propanamide

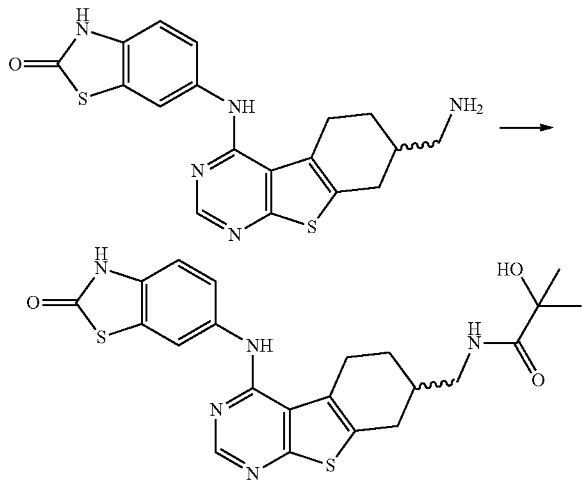

10 mg (130 μmol) (RS)-6-{[7-(aminomethyl)-5,6,7,8-tetrahydro[1]benzothieno[2,3-d]pyrimidin-4-yl]amino}-1,3-benzothiazol-2(3H)-one (prepared according to example 20) were transformed in analogy to example 23 using 2-hydroxy-2-methylpropanoic acid to give after working up and purification 23.8 mg (38%) of the title compound.

$^1$H-NMR (DMSO-d6): δ=1.23 (6H), 1.44 (1H), 1.87-2.12 (2H), 2.83 (1H), 2.91 (1H), 2.98-3.22 (4H), 5.34 (1H), 7.06 (1H), 7.42 (1H), 7.76-7.86 (2H), 8.10 (1H), 8.29 (1H), 11.79 (1H) ppm.

Example 26

(2RS)-2-Hydroxy-N-({(7RS)-4-[(2-oxo-2,3-dihydro-1,3-benzothiazol-6-yl)amino]-5,6,7,8-tetrahydro[1]benzothieno[2,3-d]pyrimidin-7-yl}methyl)propanamide

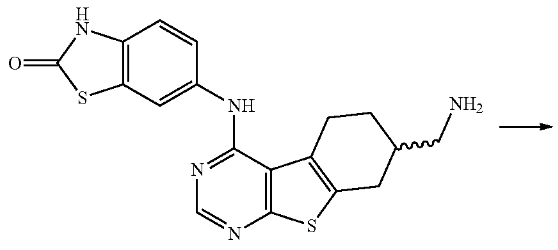

-continued

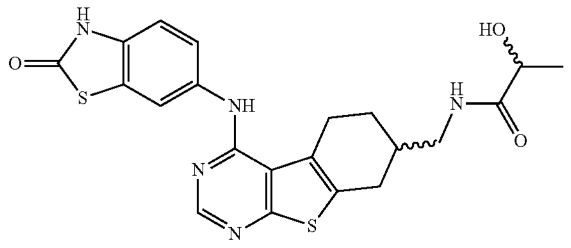

75 mg (196 μmol) (RS)-6-{[7-(aminomethyl)-5,6,7,8-tetrahydro[1]benzothieno[2,3-d]pyrimidin-4-yl]amino}-1,3-benzothiazol-2(3H)-one (prepared according to example 20) were transformed in analogy to example 23 using (RS)-2-hydroxypropanoic acid to give after working up and purification 6.0 mg (6%) of the title compound.

$^1$H-NMR (DMSO-d6): δ=1.20 (3H), 1.46 (1H), 1.87-2.09 (2H), 2.84 (1H), 3.08 (1H), 2.98-3.22 (4H), 3.96 (1H), 5.43 (1H), 7.07 (1H), 7.42 (1H), 7.81 (2H), 8.09 (1H), 8.29 (1H), 11.75 (1H) ppm.

Example 27 tert-Butyl {(2R)-4-hydroxy-1-oxo-1-[({(7RS)-4-[(2-oxo-2,3-dihydro-1,3-benzothiazol-6-yl)amino]-5,6,7,8-tetrahydro[1]benzothieno[2,3-d]pyrimidin-7-yl}methyl)amino]butan-2-yl}carbamate

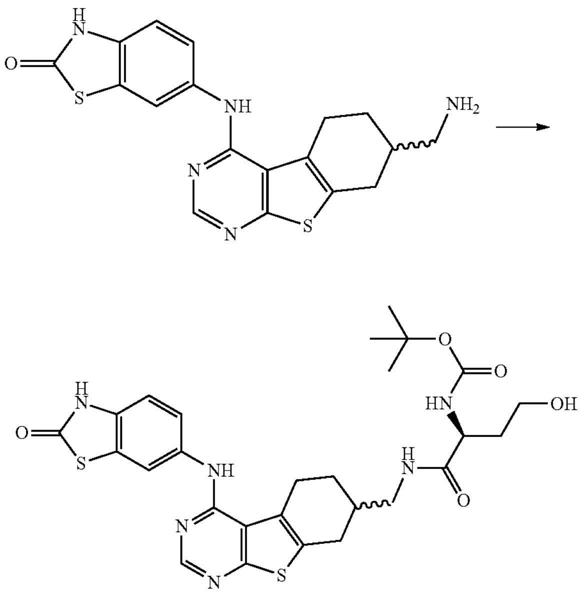

125 mg (326 μmol) (RS)-6-{[7-(aminomethyl)-5,6,7,8-tetrahydro[1]benzothieno[2,3-d]pyrimidin-4-yl]amino}-1,3-benzothiazol-2(3H)-one (prepared according to example 20) were transformed in analogy to example 23 using N-(tert-butoxycarbonyl)-L-homoserine to give after working up and purification 32.2 mg (16%) of the title compound.

$^1$H-NMR (DMSO-d6): δ=1.35 (9H), 1.47 (1H), 1.64 (1H), 1.73 (1H), 1.96 (2H), 2.46 (1H), 2.85 (1H), 2.99-3.21 (5H), 3.39 (2H), 3.94 (1H), 4.48 (1H), 6.83 (1H), 7.04 (1H), 7.36 (1H), 7.75 (1H), 7.86 (1H), 8.07 (1H), 8.28 (1H) ppm.

Example 28

(RS)—N-({4-[(2-Oxo-2,3-dihydro-1,3-benzothiazol-6-yl)amino]-5,6,7,8-tetrahydro[1]benzothieno[2,3-d]pyrimidin-7-yl}methyl)propane-2-sulfonamide

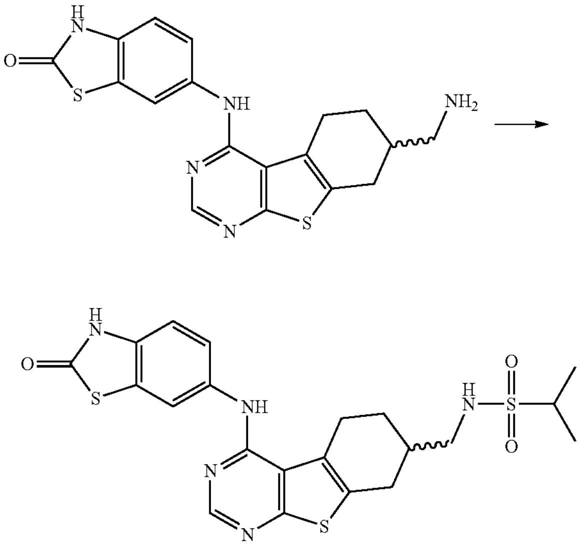

75 mg (196 μmol) (RS)-6-{[7-(aminomethyl)-5,6,7,8-tetrahydro[1]benzothieno[2,3-d]pyrimidin-4-yl]amino}-1,3-benzothiazol-2(3H)-one (prepared according to example 20), were transformed in analogy to example 21 using propane-2-sulfonyl chloride to give after working up and purification 5.7 mg (6%) of the title compound.

$^1$H-NMR (DMSO-d6): δ=1.21 (6H), 1.49 (1H), 1.92-2.09 (2H), 2.52 (1H), 2.92 (1H), 3.00 (2H), 3.09 (1H), 3.16 (2H), 7.07 (1H), 7.13 (1H), 7.42 (1H), 7.80 (1H), 8.10 (1H), 8.30 (1H), 11.05 (1H) ppm.

Example 29

(RS)-6-({7-[(4-Methylpiperazin-1-yl)carbonyl]-5,6,7,8-tetrahydro[1]benzothieno[2,3-d]pyrimidin-4-yl}amino)-1,3-benzothiazol-2(3H)-one

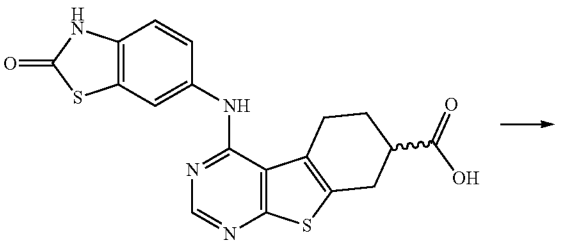

-continued

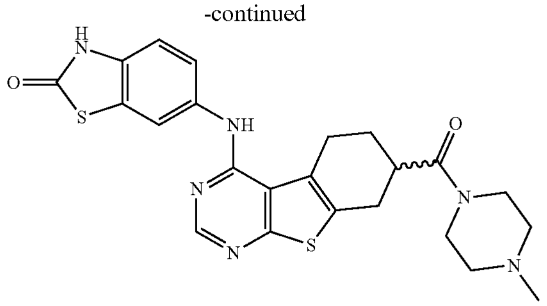

76.4 mg (192 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid (prepared according to example 2) were transformed in analogy to example 3 using 1-methylpiperazine to give after working up and purification 66.5 mg (69%) of the title compound.

$^1$H-NMR (DMSO-d6): δ=1.76 (1H), 2.00 (1H), 2.16 (3H), 2.24 (2H), 2.31 (2H), 2.85 (1H), 2.94 (1H), 3.08-3.21 (3H), 3.47 (2H), 3.52 (2H), 7.06 (1H), 7.42 (1H), 7.79 (1H), 8.12 (1H), 8.30 (1H), 11.67 (1H) ppm.

Example 30

(RS)-Ethyl 4-[(5-methoxy-2-oxo-2,3-dihydro-1,3-benzothiazol-6-yl)amino]-5,6,7,8-tetrahydro[1]benzothieno[2,3-d]pyrimidine-7-carboxylate

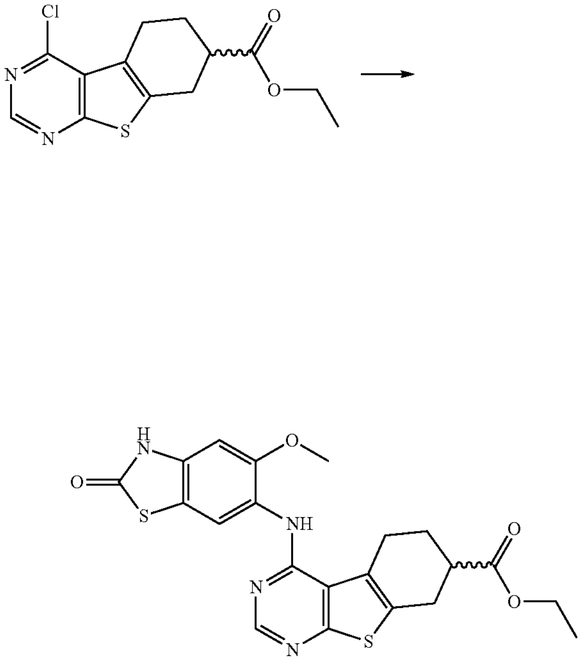

130 mg (438 μmol) (RS)-ethyl 4-chloro-5,6,7,8-tetrahydro[1]benzothieno[2,3-d]pyrimidine-7-carboxylate (prepared according to intermediate example 1a) were transformed in analogy to example 1 using 6-amino-5-methoxy-1,3-benzothiazol-2(3H)-one to give after working up and purification 98.1 mg (47%) of the title compound.

¹H-NMR (DMSO-d6): δ=1.19 (3H), 1.92 (1H), 2.26 (1H), 2.85-3.16 (5H), 3.86 (3H), 4.10 (2H), 6.79 (1H), 8.01 (1H), 8.37 (1H), 8.44 (1H), 11.74 (1H) ppm.

Example 31

(RS)-4-[(5-methoxy-2-oxo-2,3-dihydro-1,3-benzothiazol-6-yl)amino]-Nropan-2-yl)-5,6,7,8-tetrahydro[1]benzothieno[2,3-d]pyrimidine-7-carboxamide

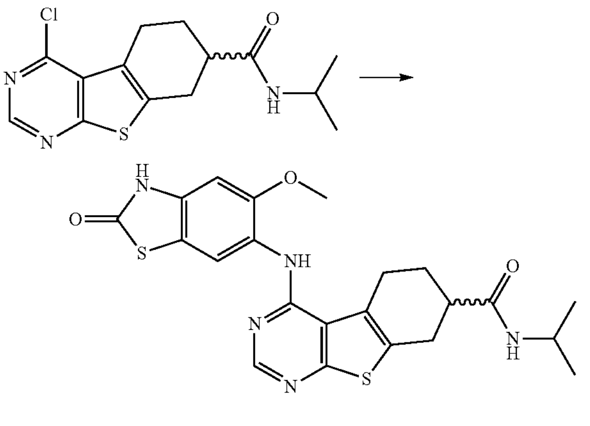

30 mg (97 μmol) (RS)-4-chloro-N-isopropyl-5,6,7,8-tetrahydro[1]benzothieno[2,3-d]pyrimidine-7-carboxamide (prepared according to intermediate example 31a) were transformed in analogy to example 1 using 6-amino-5-methoxy-1,3-benzothiazol-2(3H)-one to give after working up and purification 22 mg (46%) of the title compound.

¹H-NMR (DMSO-d6): δ=1.00-1.09 (6H), 1.81 (1H), 2.11 (1H), 2.60 (1H), 2.89 (2H), 3.02 (1H), 3.16 (1H), 3.84 (1H), 3.86 (3H), 6.79 (1H), 7.79 (1H), 8.02 (1H), 8.37 (1H), 8.47 (1H), 11.75 (1H) ppm.

Example 31a (RS)-4-Chloro-N-isopropyl-5,6,7,8-tetrahydro[1]benzothieno[2,3-d]pyrimidine-7-carboxamide

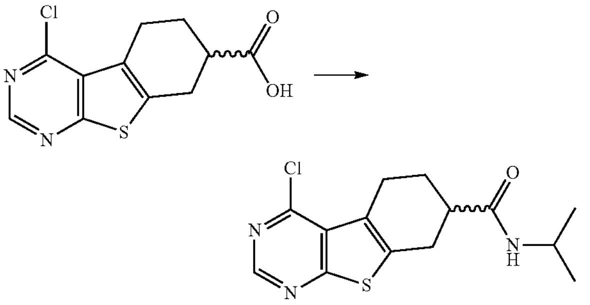

13.18 g (49.05 mmol) (RS)-4-chloro-5,6,7,8-tetrahydro[1]benzothieno[2,3-d]pyrimidine-7-carboxylic acid (prepared according to intermediate example 31b) were transformed in analogy to example 3 using propan-2-amine to give after working up and purification 11.39 g (71%) of the title compound.

Example 31b (RS)-4-Chloro-5,6,7,8-tetrahydro[1]benzothieno[2,3-d]pyrimidine-7-carboxylic acid

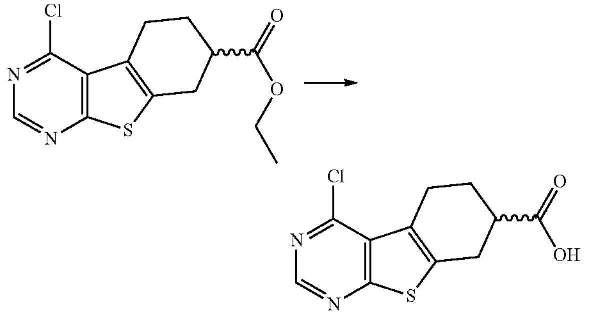

5.0 g (16.85 mmol) (RS)-ethyl 4-chloro-5,6,7,8-tetrahydro[1]benzothieno[2,3-d]pyrimidine-7-carboxylate (prepared according to intermediate example 1a) were transformed in analogy to example 2 to give after working up and purification 4.45 g (88%) of the title compound.

Example 32

N-({4-[(2-Oxo-2,3-dihydro-1,3-benzothiazol-6-yl)amino]-5,6,7,8-tetrahydro[1]benzothieno[2,3-d]pyrimidin-7-(RS)-yl}methyl)-L-homoserinamide

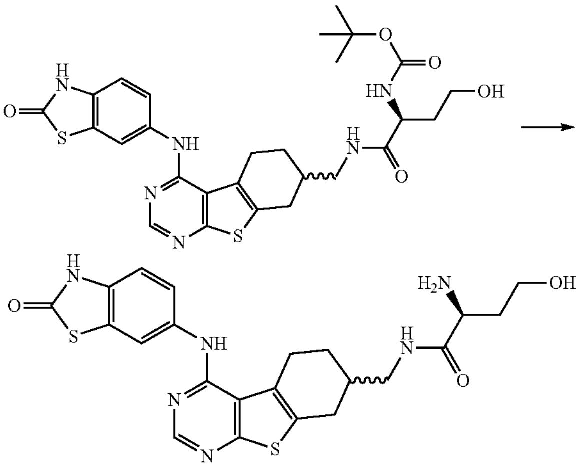

A mixture comprising 32.5 mg (56 μmol) tert-butyl {(2R)-4-hydroxy-1-oxo-1-[({(7RS)-4-[(2-oxo-2,3-dihydro-1,3-benzothiazol-6-yl)amino]-5,6,7,8-tetrahydro[1]benzothieno[2,3-d]pyrimidin-7-yl}methyl)amino]butan-2-yl}carbamate (prepared according to example 27), 1.0 mL 1,4-dioxane and 42.7 μL hydrochloric acid (4M in 1,4-dioxane) was stirred at 23° C. overnight. 1 mL N,N-diethylethanamine was added, the solvents removed and the residue purified by chromatography to give 6.3 mg (22%) of the title compound.

$^1$H-NMR (DMSO-d6): δ=1.48 (2H), 1.73 (1H), 1.95 (2H), 2.47 (1H), 2.86 (1H), 2.98-3.29 (6H), 3.47 (2H), 7.05 (1H), 7.39 (1H), 7.78 (1H), 7.99 (1H), 8.09 (1H), 8.29 (1H) ppm.

Example 33

4-[(5-Methoxy-2-oxo-2,3-dihydro-1,3-benzothiazol-6-yl)amino]-5,6,7,8-tetrahydro[1]benzothieno[2,3-d]pyrimidine-7-carboxylic acid

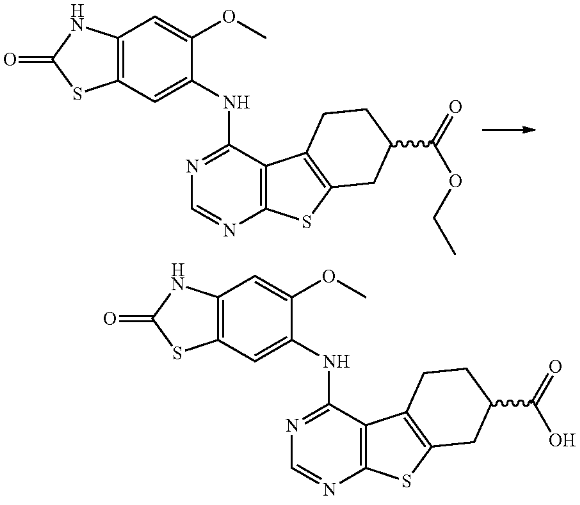

85 mg (186 μmol) (RS)-ethyl 4-[(5-methoxy-2-oxo-2,3-dihydro-1,3-benzothiazol-6-yl)amino]-5,6,7,8-tetrahydro[1]benzothieno[2,3-d]pyrimidine-7-carboxylate (prepared according to example 30) were transformed in analogy to example 2 to give after working up and purification 72.2 mg (86%) of the title compound.

$^1$H-NMR (DMSO-d6): δ=1.91 (1H), 2.26 (1H), 2.82 (1H), 2.93 (1H), 3.03 (1H), 3.12 (2H), 3.86 (3H), 6.78 (1H), 8.01 (1H), 8.37 (1H), 8.44 (1H), 11.76 (1H), 12.43 (1H) ppm.

Examples 34-84

The compounds of examples 34-84 listed in Table 1 were prepared and purified in analogy to example 3.

The compounds of examples 34-84 were analyzed according to the equipment and conditions given below:

Instrument MS: Waters ZQ;

Instrument HPLC: Waters UPLC Acquity;

Column: Acquity BEH C18 (Waters), 50 mm×2.1 mm, 1.7 μm; Eluent A: $H_2O$+0.1 vol % formic acid, Eluent B: Acetonitrile (Lichrosolv Merck);

Gradient: 0.0 min 99% A-1.6 min 1% A-1.8 min 1% A-1.81 min 99% A-2.0 min 99% A;

Oven temperature: 60° C.; Flow: 0.800 ml/min;

UV-Detection PDA 210-400 nm

TABLE 1

| A | B | C | D | E |
|---|---|---|---|---|
| 34 | 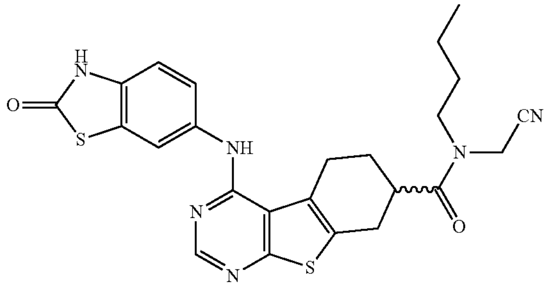 | (RS)-N-butyl-N-(cyanonmethyl)-4-[(2-oxo-2,3-dihydro-1,3-benzothiazol-6-yl)amino]-5,6,7,8-tetrahydro[1]benzothieno[2,3-d]pyrimidine-7-carboxamide | 1.09 | 493 |
| 35 | 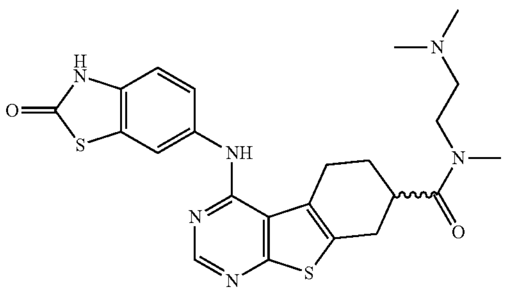 | (RS)-N-[2-(dimethylamino)ethyl]-N-methyl-4-[(2-oxo-2,3-dihydro-1,3-benzothiazol-6-yl)amino]-5,6,7,8-tetrahydro[1]benzothieno[2,3-d]pyrimidine-7-carboxamide | 0.65 | 483 |

TABLE 1-continued

| A | B | C | D | E |
|---|---|---|---|---|
| 36 | 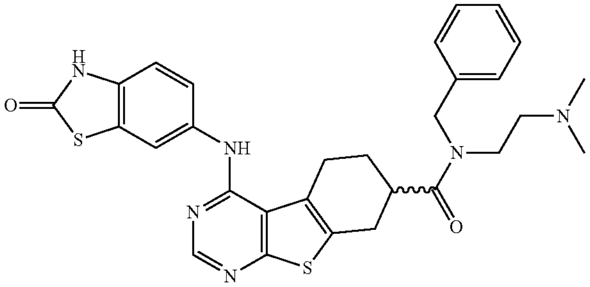 | (RS)-N-benzyl-N-[2-(dimethylamino)ethyl]-4-[(2-oxo-2,3-dihydro-1,3-benzothiazol-6-yl)amino]-5,6,7,8-tetrahydro[1]benzothieno[2,3-d]pyrimidine-7-carboxamide | 0.78 | 559 |
| 37 | 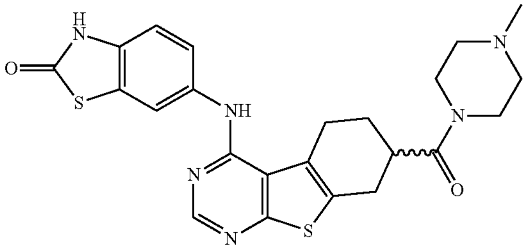 | (RS)-6-({7-[(4-methylpiperazin-1-yl)carbonyl]-5,6,7,8-tetrahydro[1]benzothieno[2,3-d]pyrimidin-4-yl}amino)-1,3-benzothiazol-2(3H)-one | 0.64 | 481 |
| 38 | 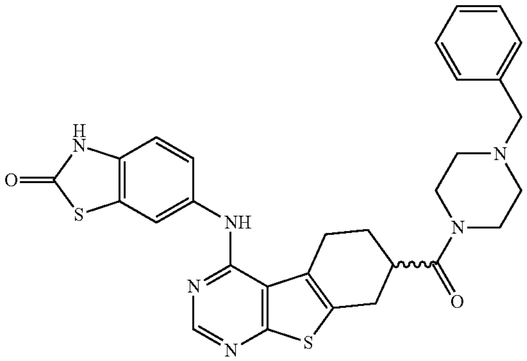 | 6-({7-[(4-benzylpiperazin-1-yl)carbonyl]-5,6,7,8-tetrahydro[1]benzothieno[2,3-d]pyrimidin-4-yl}amino)-1,3-benzothiazol-2(3H)-one | 0.74 | 557 |
| 39 | 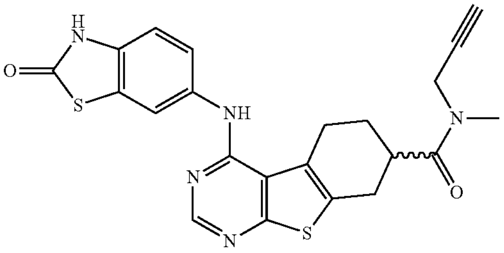 | (RS)-N-methyl-4-[(2-oxo-2,3-dihydro-1,3-benzothiazol-6-yl)amino]-N-(prop-2-yn-1-yl)-5,6,7,8-tetrahydro[1]benzothieno[2,3-d]pyrimidine-7-carboxamide | 0.97 | 450 |
| 40 | 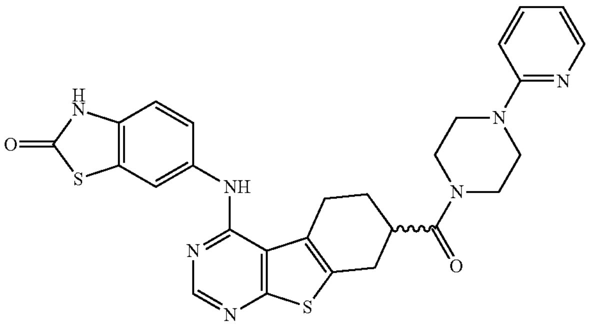 | (RS)-6-[(7-{[4-(pyridin-2-yl)piperazin-1-yl]carbonyl}-5,6,7,8-tetrahydro[1]benzothieno[2,3-d]pyrimidin-4-yl)amino]-1,3-benzothiazol-2(3H)-one | 0.76 | 544 |

TABLE 1-continued

| A | B | C | D | E |
|---|---|---|---|---|
| 41 | 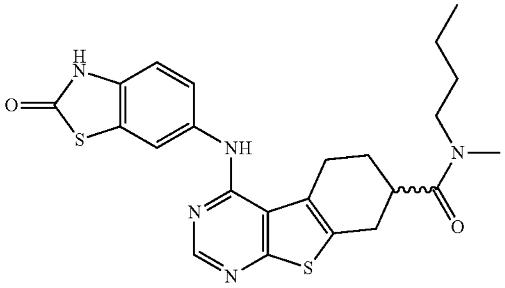 | (RS)-N-butyl-N-methyl-4-[(2-oxo-2,3-dihydro-1,3-benzothiazol-6-yl)amino]-5,6,7,8-tetrahydro[1]benzothieno[2,3-d]pyrimidine-7-carboxamide | 1.12 | 468 |
| 42 | 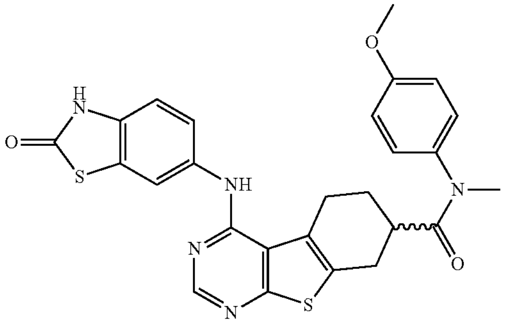 | (RS)-N-(4-methoxyphenyl)-N-methyl-4-[(2-oxo-2,3-dihydro-1,3-benzothiazol-6-yl)amino]-5,6,7,8-tetrahydro[1]benzothieno[2,3-d]pyrimidine-7-carboxamide | 1.11 | 518 |
| 43 | 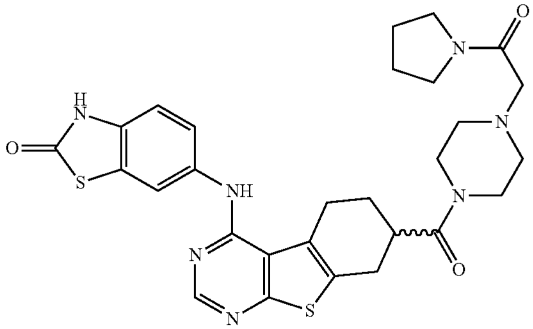 | (RS)-6-{[7-({4-[2-oxo-2-(pyrrolidin-1-yl)ethyl]piperazin-1-yl}carbonyl)-5,6,7,8-tetrahydro[1]benzothieno[2,3-d]pyrimidin-4-yl]amino}-1,3-benzothiazol-2(3H)-one | 0.69 | 578 |
| 44 | 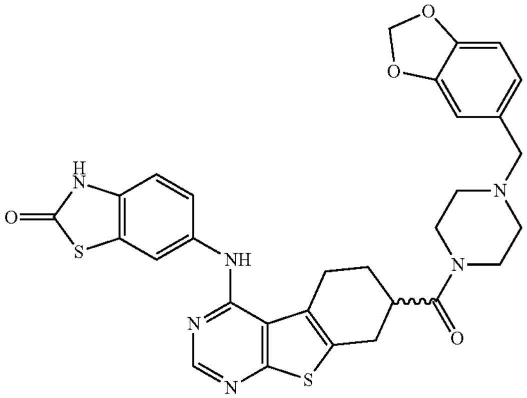 | (RS)-6-[(7-{[4-(1,3-benzodioxol-5-ylmethyl)piperazin-1-yl]carbonyl}-5,6,7,8-tetrahydro[1]benzothieno[2,3-d]pyrimidin-4-yl)amino]-1,3-benzothiazol-2(3H)-one | 0.75 | 601 |
| 45 | 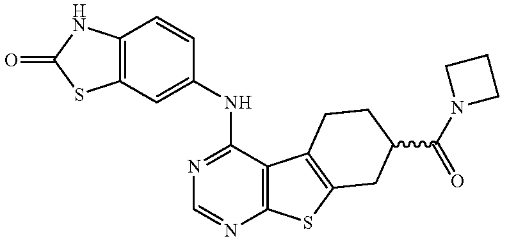 | (RS)-6-{[7-(azetidin-1-ylcarbonyl)-5,6,7,8-tetrahydro[1]benzothieno[2,3-d]pyrimidin-4-yl]amino}-1,3-benzothiazol-2(3H)-one | 0.89 | 438 |

TABLE 1-continued

| A | B | C | D | E |
|---|---|---|---|---|
| 46 | 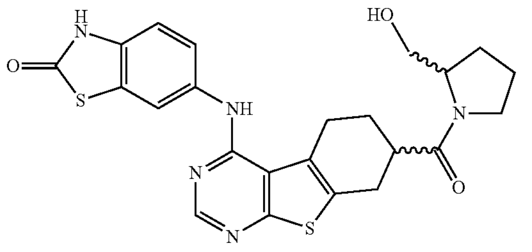 | 6-{[(7RS)-7-{[(2RS)-2-(hydroxymethyl)pyrrolidin-1-yl]carbonyl}-5,6,7,8-tetrahydro[1]benzothieno[2,3-d]pyrimidin-4-yl]amino}-1,3-benzothiazol-2(3H)-one | 0.87 | 482 |
| 47 | 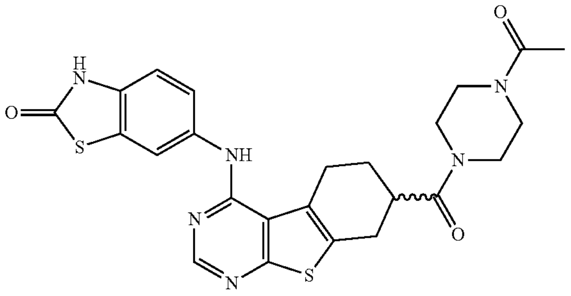 | (RS)-6-({7-[(4-acetylpiperazin-1-yl)carbonyl]-5,6,7,8-tetrahydro[1]benzothieno[2,3-d]pyrimidin-4-yl}amino)-1,3-benzothiazol-2(3H)-one | 0.83 | 509 |
| 48 | 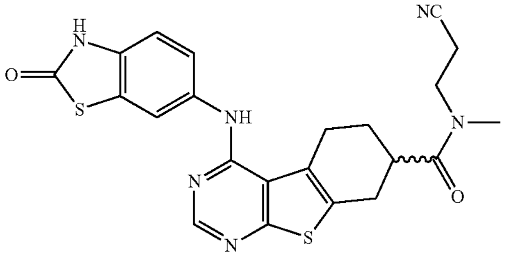 | (RS)-N-(2-cyanoethyl)-N-methyl-4-[(2-oxo-2,3-dihydro-1,3-benzothiazol-6-yl)amino]-5,6,7,8-tetrahydro[1]benzothieno[2,3-d]pyrimidine-7-carboxamide | 0.88 | 465 |
| 49 | 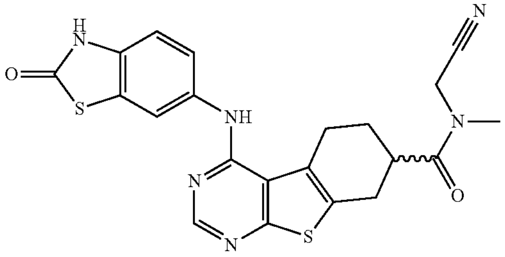 | (RS)-N-(cyanomethyl)-N-methyl-4-[(2-oxo-2,3-dihydro-1,3-benzothiazol-6-yl)amino]-5,6,7,8-tetrahydro[1]benzothieno[2,3-d]pyrimidine-7-carboxamide | 0.9 | 451 |
| 50 | 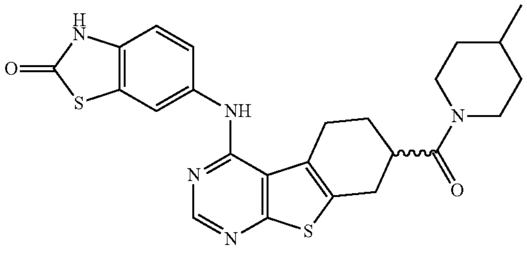 | (RS)-6-({7-[(4-methylpiperidin-1-yl)carbonyl]-5,6,7,8-tetrahydro[1]benzothieno[2,3-d]pyrimidin-4-yl}amino)-1,3-benzothiazol-2(3H)-one | 1.14 | 480 |

TABLE 1-continued

| A | B | C | D | E |
|---|---|---|---|---|
| 51 | 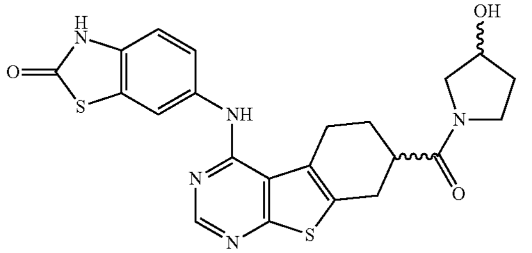 | 6-{[(7RS)-7-{[(3RS)-3-hydroxypyrrolidin-1-yl]carbonyl}-5,6,7,8-tetrahydro[1]benzothieno[2,3-d]pyrimidin-4-yl]amino}-1,3-benzothiazol-2(3H)-one | 0.79 | 468 |
| 52 | 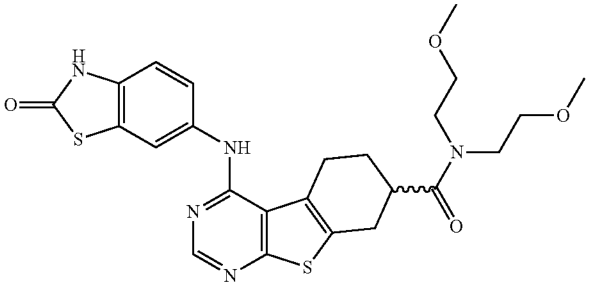 | (RS)-N,N-bis(2-methoxyethyl)-4-[(2-oxo-2,3-dihydro-1,3-benzothiazol-6-yl)amino]-5,6,7,8-tetrahydro[1]benzothieno[2,3-d]pyrimidine-7-carboxamide | 0.98 | 514 |
| 53 | 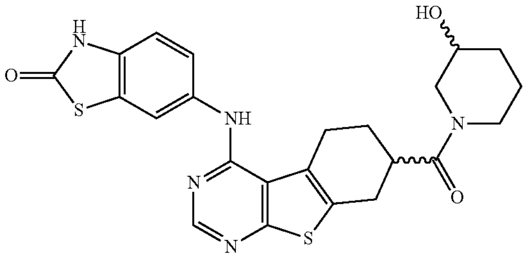 | 6-{[(7RS)-7-{[(3RS)-3-hydroxypiperidin-1-yl]carbonyl}-5,6,7,8-tetrahydro[1]benzothieno[2,3-d]pyrimidin-4-yl]amino}-1,3-benzothiazol-2(3H)-one | 0.85 | 482 |
| 54 | 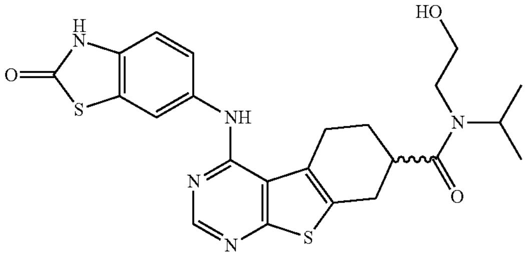 | (RS)-N-(2-hydroxyethyl)-N-isopropyl-4-[(2-oxo-2,3-dihydro-1,3-benzothiazol-6-yl)amino]-5,6,7,8-tetrahydro[1]benzothieno[2,3-d]pyrimidine-7-carboxamide | 0.7 | 484 |
| 55 | 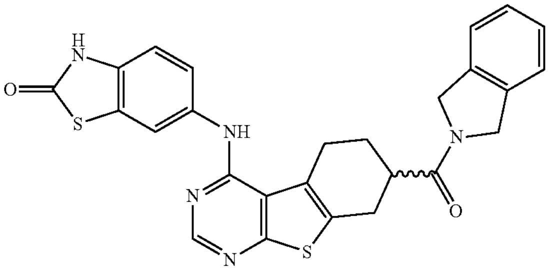 | (RS)-6-{[7-(1,3-dihydro-2H-isoindol-2-ylcarbonyl)-5,6,7,8-tetrahydro[1]benzothieno[2,3-d]pyrimidin-4-yl]amino}-1,3-benzothiazol-2(3H)-one | 1.11 | 500 |

TABLE 1-continued

| A | B | C | D | E |
|---|---|---|---|---|
| 56 | 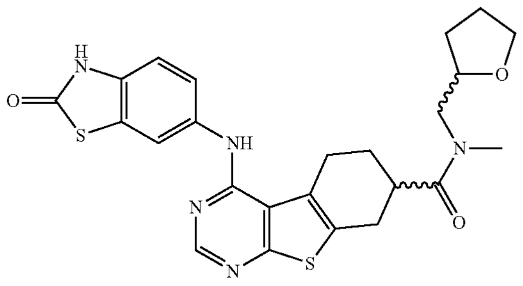 | (7RS)-N-methyl-4-[(2-oxo-2,3-dihydro-1,3-benzothiazol-6-yl)amino]-N-[(2RS)-tetrahydrofuran-2-ylmethyl]-5,6,7,8-tetrahydro[1]benzothieno[2,3-d]pyrimidine-7-carboxamide | 0.98 | 496 |
| 57 | 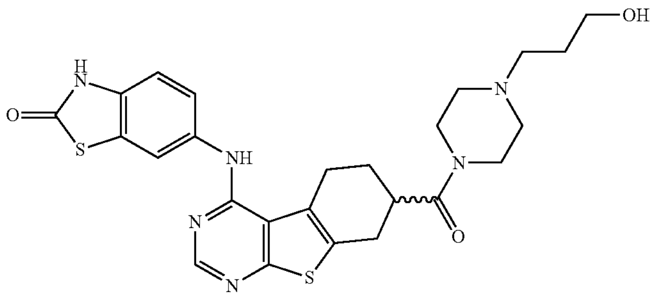 | (RS)-6-[(7-{[4-(3-hydroxypropyl)piperazin-1-yl]carbonyl}-5,6,7,8-tetrahydro[1]benzothieno[2,3-d]pyrimidin-4-yl)amino]-1,3-benzothiazol-2(3H)-one | 0.64 | 525 |
| 58 | 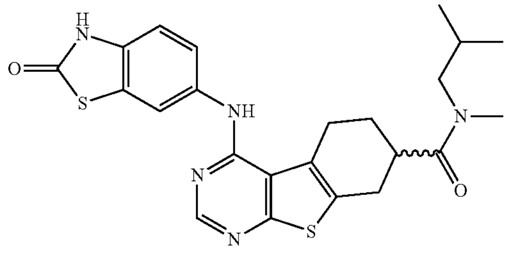 | (RS)-N-isobutyl-N-methyl-4-[(2-oxo-2,3-dihydro-1,3-benzothiazol-6-yl)amino]-5,6,7,8-tetrahydro[1]benzothieno[2,3-d]pyrimidine-7-carboxamide | 1.11 | 468 |
| 59 | 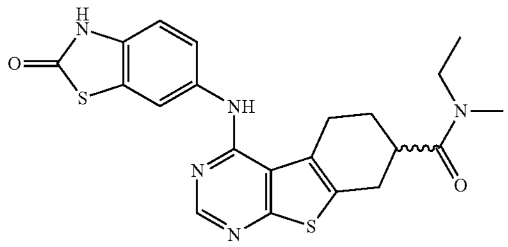 | (RS)-N-ethyl-N-methyl-4-[(2-oxo-2,3-dihydro-1,3-benzothiazol-6-yl)amino]-5,6,7,8-tetrahydro[1]benzothieno[2,3-d]pyrimidine-7-carboxamide | 0.96 | 440 |
| 60 | 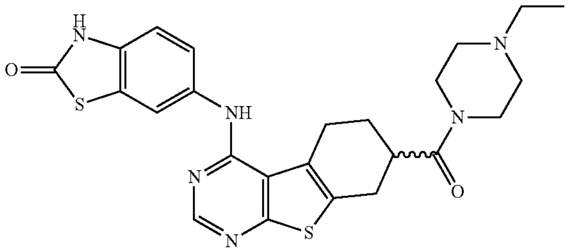 | (RS)-6-({7-[(4-ethylpiperazin-1-yl)carbonyl]-5,6,7,8-tetrahydro[1]benzothieno[2,3-d]pyrimidin-4-yl}amino)-1,3-benzothiazol-2(3H)-one | 0.65 | 495 |

TABLE 1-continued

| A | B | C | D | E |
|---|---|---|---|---|
| 61 | 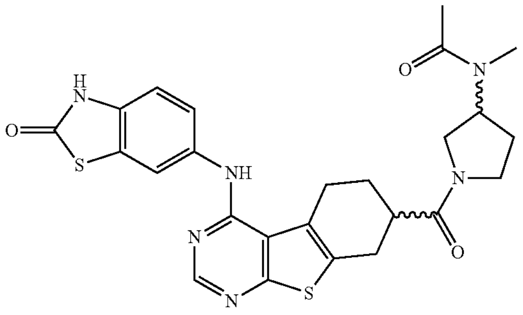 | N-methyl-N-[(3RS)-1-({(7RS)-4-[(2-oxo-2,3-dihydro-1,3-benzothiazol-6-yl)amino]-5,6,7,8-tetrahydro[1]benzothieno[2,3-d]pyrimidin-7-yl}carbonyl)pyrrolidin-3-yl]acetamide | 0.84 | 523 |
| 62 | 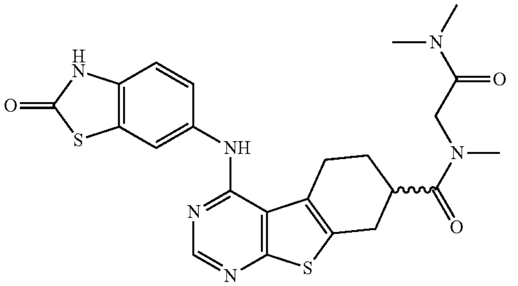 | (RS)-N-[2-(dimethylamino)-2-oxoethyl]-N-methyl-4-[(2-oxo-2,3-dihydro-1,3-benzothiazol-6-yl)amino]-5,6,7,8-tetrahydro[1]benzothieno[2,3-d]pyrimidine-7-carboxamide | 0.84 | 497 |
| 63 | 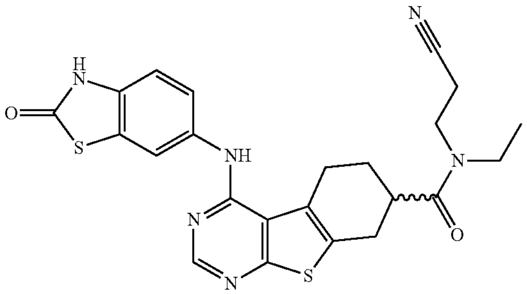 | (RS)-N-(2-cyanoethyl)-N-ethyl-4-[(2-oxo-2,3-dihydro-1,3-benzothiazol-6-yl)amino]-5,6,7,8-tetrahydro[1]benzothieno[2,3-d]pyrimidine-7-carboxamide | 0.94 | 479 |
| 64 | 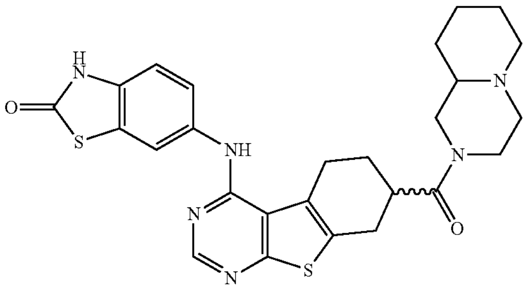 | 6-({(7RS)-7-[(9aRS)-octahydro-2H-pyrido[1,2-a]pyrazin-2-ylcarbonyl]-5,6,7,8-tetrahydro[1]benzothieno[2,3-d]pyrimidin-4-yl}amino)-1,3-benzothiazol-2(3H)-one | 0.67 | 521 |
| 65 | 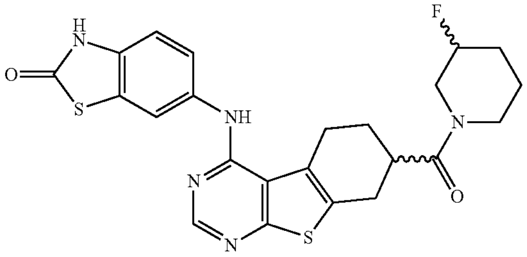 | 6-{[(7RS)-7-{[(3RS)-3-fluoropiperidin-1-yl]carbonyl}-5,6,7,8-tetrahydro[1]benzothieno[2,3-d]pyrimidin-4-yl]amino}-1,3-benzothiazol-2(3H)-one | 0.99 | 484 |

TABLE 1-continued

| A | B | C | D | E |
|---|---|---|---|---|
| 66 | 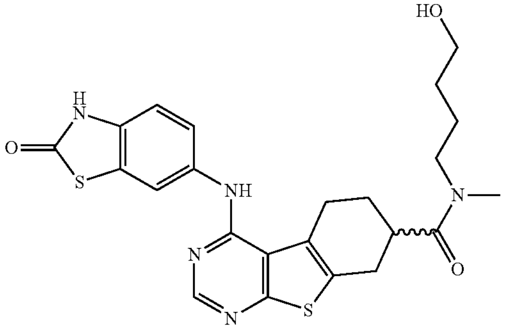 | (RS)-N-(4-hydroxybutyl)-N-methyl-4-[(2-oxo-2,3-dihydro-1,3-benzothiazol-6-yl)amino]-5,6,7,8-tetrahydro[1]benzothieno[2,3-d]pyrimidine-7-carboxamide | 0.86 | 484 |
| 67 | 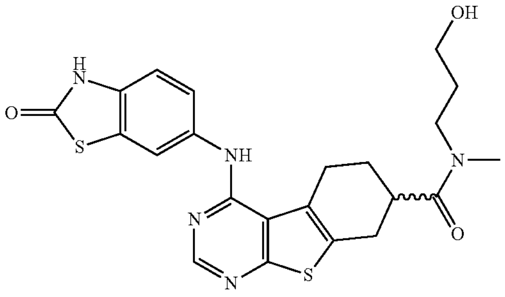 | (RS)-N-(3-hydroxypropyl)-N-methyl-4-[(2-oxo-2,3-dihydro-1,3-benzothiazol-6-yl)amino]-5,6,7,8-tetrahydro[1]benzothieno[2,3-d]pyrimidine-7-carboxamide | 0.83 | 470 |
| 68 | 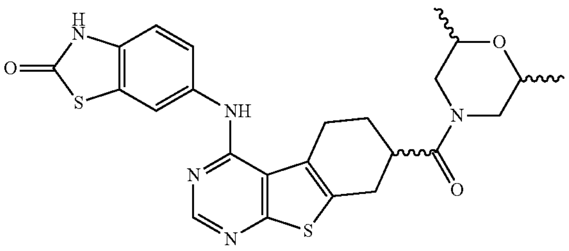 | 6-{[(7RS)-7-{[(2RS,6RS)-2,6-dimethylmorpholin-4-yl]carbonyl}-5,6,7,8-tetrahydro[1]benzothieno[2,3-d]pyrimidin-4-yl]amino}-1,3-benzothiazol-2(3H)-one | 1.02 | 496 |
| 69 | 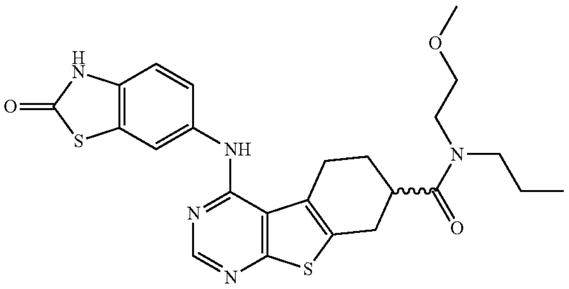 | (RS)-N-(2-methoxyethyl)-4-[(2-oxo-2,3-dihydro-1,3-benzothiazol-6-yl)amino]-N-propyl-5,6,7,8-tetrahydro[1]benzothieno[2,3-d]pyrimidine-7-carboxamide | 1.07 | 498 |
| 70 | 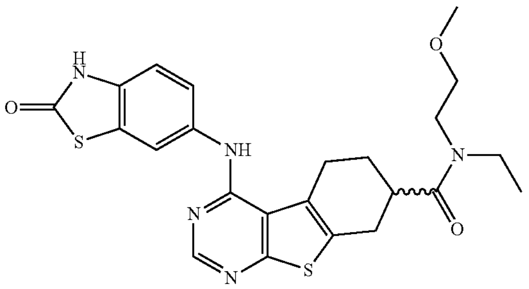 | (RS)-N-ethyl-N-(2-methoxyethyl)-4-[(2-oxo-2,3-dihydro-1,3-benzothiazol-6-yl)amino]-5,6,7,8-tetrahydro[1]benzothieno[2,3-d]pyrimidine-7-carboxamide | 1.0 | 484 |

TABLE 1-continued

| A | B | C | D | E |
|---|---|---|---|---|
| 71 | 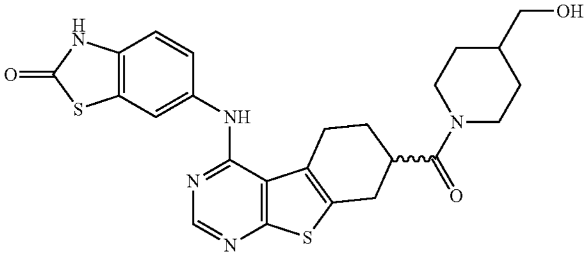 | (RS)-6-[(7-{[4-(hydroxymethyl)piperidin-1-yl]carbonyl}-5,6,7,8-tetrahydro[1]benzothieno[2,3-d]pyrimidin-4-yl)amino]-1,3-benzothiazol-2(3H)-one | 0.86 | 496 |
| 72 | 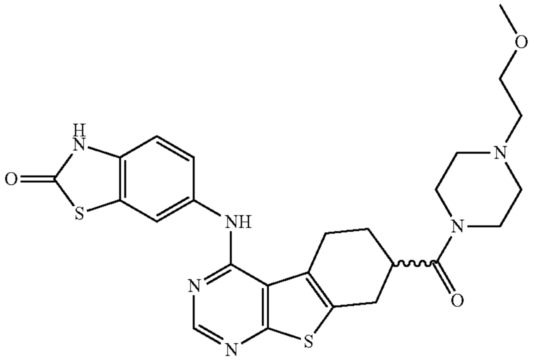 | (RS)-6-[(7-{[4-(2-methoxyethyl)piperazin-1-yl]carbonyl}-5,6,7,8-tetrahydro[1]benzothieno[2,3-d]pyrimidin-4-yl)amino]-1,3-benzothiazol-2(3H)-one | 0.66 | 525 |
| 73 | 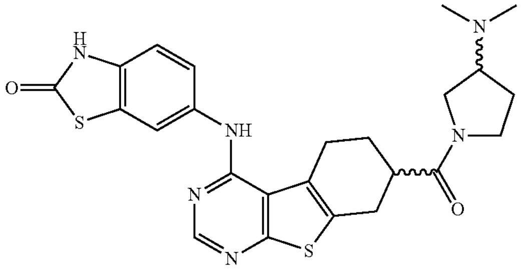 | 6-{[(7RS)-7-{[(3RS)-3-(dimethylamino)pyrrolidin-1-yl]carbonyl}-5,6,7,8-tetrahydro[1]benzothieno[2,3-d]pyrimidin-4-yl]amino}-1,3-benzothiazol-2(3H)-one | 0.63 | 495 |
| 74 | 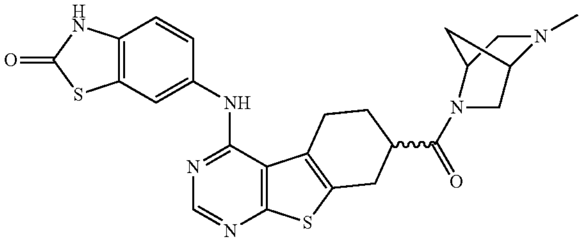 | 6-{[(7RS)-7-{[(1RS,4RS)-5-methyl-2,5-diazabicyclo[2.2.1]hept-2-yl]carbonyl}-5,6,7,8-tetrahydro[1]benzothieno[2,3-d]pyrimidin-4-yl]amino}-1,3-benzothiazol-2(3H)-one | 0.63 | 493 |
| 75 | 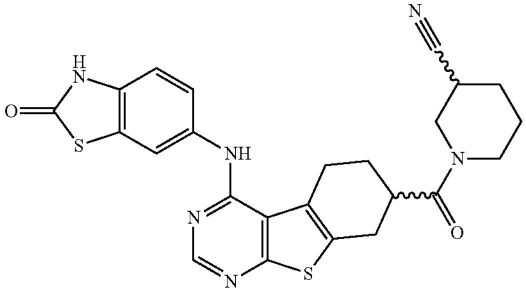 | (3RS)-1-({(7RS)-4-[(2-oxo-2,3-dihydro-1,3-benzothiazol-6-yl)amino]-5,6,7,8-tetrahydro[1]benzothieno[2,3-d]pyrimidin-7-yl}carbonyl)piperidine-3-carbonitrile | 0.94 | 491 |

TABLE 1-continued

| A | B | C | D | E |
|---|---|---|---|---|
| 76 | 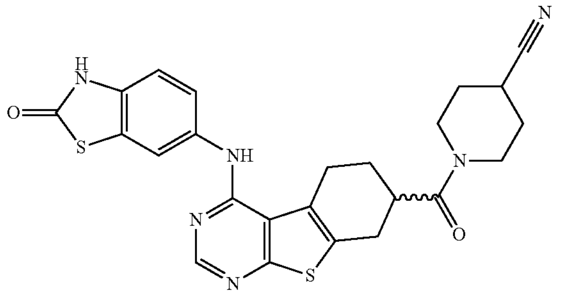 | (RS)-1-({4-[(2-oxo-2,3-dihydro-1,3-benzothiazol-6-yl)amino]-5,6,7,8-tetrahydro[1]benzothieno[2,3-d]pyrimidin-7-yl}carbonyl)piperidine-4-carbonitrile | 0.93 | 491 |
| 77 | 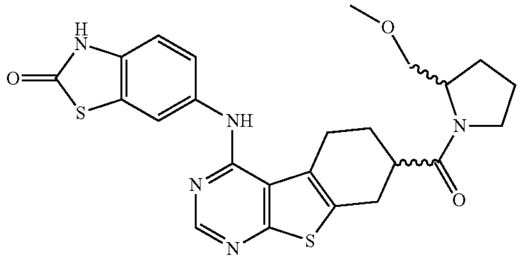 | 6-{[(7RS)-7-{[(2RS)-2-(methoxymethyl)pyrrolidin-1-yl]carbonyl}-5,6,7,8-tetrahydro[1]benzothieno[2,3-d]pyrimidin-4-yl]amino}-1,3-benzothiazol-2(3H)-one | 1.01 | 496 |
| 78 | 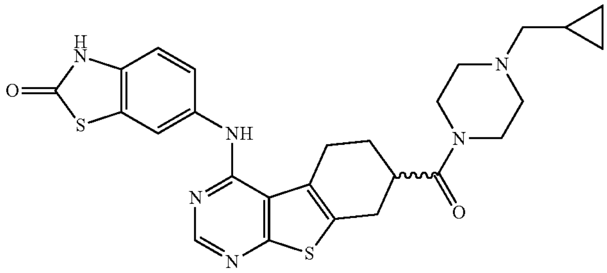 | (RS)-6-[(7-{[4-(cyclopropylmethyl)piperazin-1-yl]carbonyl}-5,6,7,8-tetrahydro[1]benzothieno[2,3-d]pyrimidin-4-yl)amino]-1,3-benzothiazol-2(3H)-one | 0.68 | 521 |
| 79 | 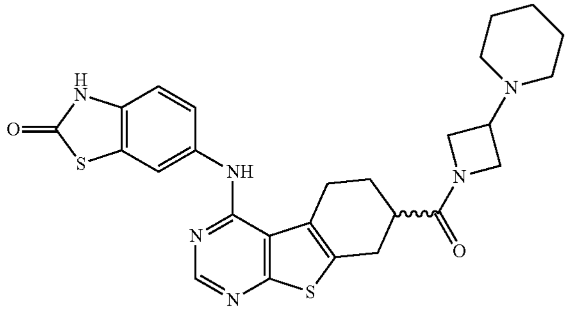 | (RS)-6-[(7-{[3-(piperidin-1-yl)azetidin-1-yl]carbonyl}-5,6,7,8-tetrahydro[1]benzothieno[2,3-d]pyrimidin-4-yl)amino]-1,3-benzothiazol-2(3H)-one | 0.65 | 521 |
| 80 | 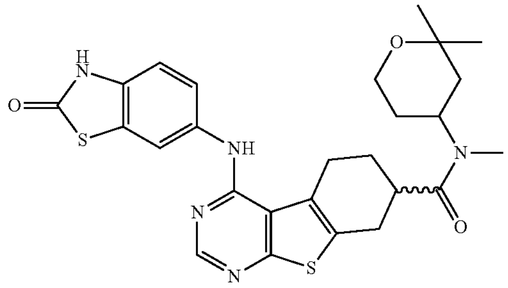 | (RS)-N-(2,2-dimethyltetrahydro-2H-pyran-4-yl)-N-methyl-4-[(2-oxo-2,3-dihydro-1,3-benzothiazol-6-yl)amino]-5,6,7,8-tetrahydro[1]benzothieno[2,3-d]pyrimidine-7-carboxamide | 1.03 | 524 |

TABLE 1-continued

| A | B | C | D | E |
|---|---|---|---|---|
| 81 | 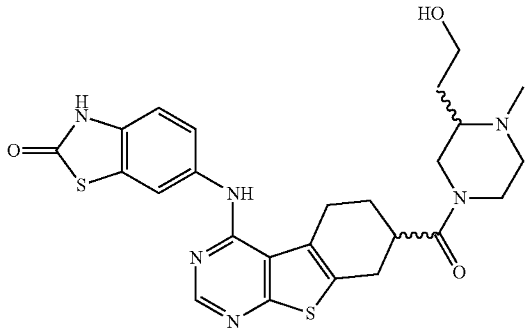 | 6-{[(7RS)-7-{[(3RS)-3-(2-hydroxyethyl)-4-methylpiperazin-1-yl]carbonyl}-5,6,7,8-tetrahydro[1]benzothieno[2,3-d]pyrimidin-4-yl]amino}-1,3-benzothiazol-2(3H)-one | 0.64 | 525 |
| 82 | 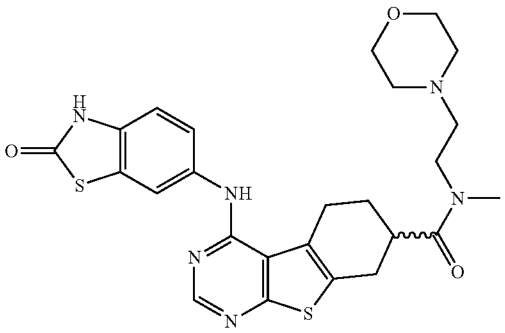 | (RS)-N-methyl-N-[2-(morpholin-4-yl)ethyl]-4-[(2-oxo-2,3-dihydro-1,3-benzothiazol-6-yl)amino]-5,6,7,8-tetrahydro[1]benzothieno[2,3-d]pyrimidine-7-carboxamide | 0.66 | 525 |
| 83 | 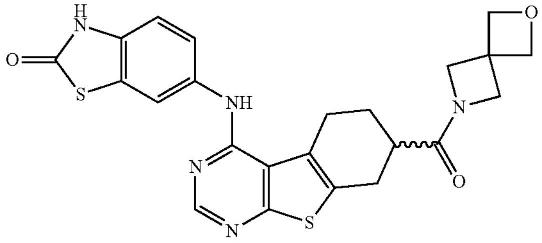 | (RS)-6-{[7-(2-oxa-6-azaspiro[3.3]hept-6-ylcarbonyl)-5,6,7,8-tetrahydro[1]benzothieno[2,3-d]pyrimidin-4-yl]amino}-1,3-benzothiazol-2(3H)-one | 0.83 | 480 |
| 84 | 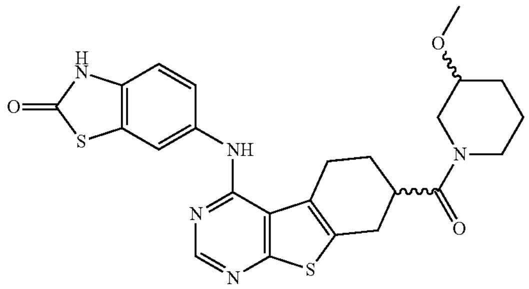 | 6-{[(7RS)-7-{[(3RS)-3-methoxypiperidin-1-yl]carbonyl}-5,6,7,8-tetrahydro[1]benzothieno[2,3-d]pyrimidin-4-yl]amino}-1,3-benzothiazol-2(3H)-one | 0.99 | 496 |

Column header:
A: Example
B: Structure
C: IUPAC Name
D: Retention time [min]
E: MS (ESIpos) m/z $[M + H]^+$ Example 85

(RS)-4-[(5-methoxy-2-oxo-2,3-dihydro-1,3-benzothiazol-6-yl)amino]-N,N-dimethyl-5,6,7,8-tetrahydro[1]benzothieno[2,3-d]pyrimidine-7-carboxamide

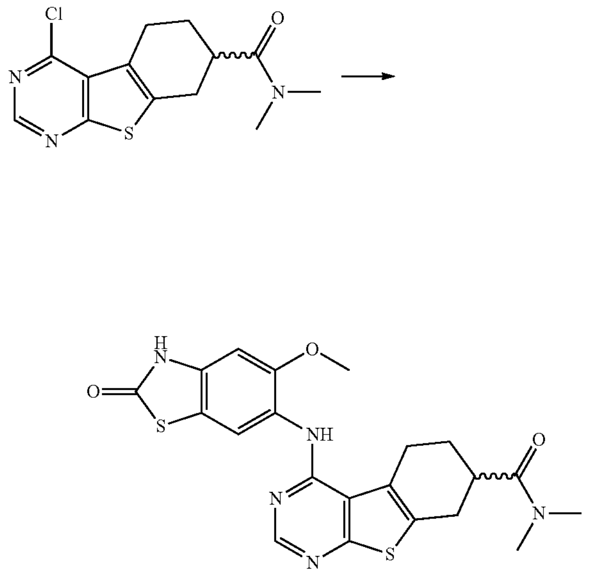

30 mg (101 μmol) (RS)-4-chloro-N,N-dimethyl-5,6,7,8-tetrahydro[1]benzothieno[2,3-d]pyrimidine-7-carboxamide (prepared according to intermediate example 85a) were transformed in analogy to example 1 using 6-amino-5-methoxy-1,3-benzothiazol-2(3H)-one to give after working up and purification 5.8 mg (12%) of the title compound.

$^{1}$H-NMR (DMSO-d6): δ=1.78 (1H), 2.11 (1H), 2.80-3.22 (5H), 2.87 (3H), 3.10 (3H), 3.88 (3H), 6.78 (1H), 8.02 (1H), 8.39 (1H), 8.48 (1H), 11.80 (1H) ppm.

Example 85a (RS)-4-chloro-N,N-dimethyl-5,6,7,8-tetrahydro[1]benzothieno[2,3-d]pyrimidine-7-carboxamide

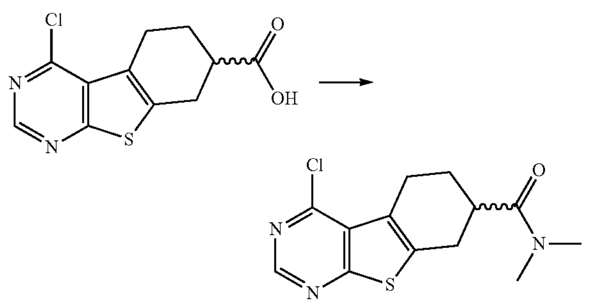

2.00 g (7.44 mmol) (RS)-4-chloro-5,6,7,8-tetrahydro[1]benzothieno[2,3-d]pyrimidine-7-carboxylic acid (prepared according to intermediate example 31b) were transformed in analogy to example 3 using N-methylmethanamine to give after working up and purification 1.68 g (76%) of the title compound.

Example 86

(RS)—N-Ethyl-N-isopropyl-4-[(5-methoxy-2-oxo-2,3-dihydro-1,3-benzothiazol-6-yl)amino]-5,6,7,8-tetrahydro[1]benzothieno[2,3-d]pyrimidine-7-carboxamide

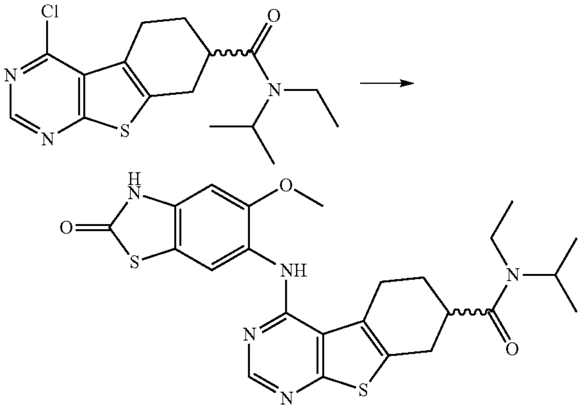

40 mg (118 μmol) (RS)-4-chloro-N-ethyl-N-isopropyl-5,6,7,8-tetrahydro[1]benzothieno[2,3-d]pyrimidine-7-carboxamide (prepared according to intermediate example 86a) were transformed in analogy to example 1 using 6-amino-5-methoxy-1,3-benzothiazol-2(3H)-one to give after working up and purification 10.9 mg (18%) of the title compound.

$^{1}$H-NMR (DMSO-d6): δ=1.01-1.24 (9H), 1.85 (1H), 2.07 (1H), 2.82-3.07 (3H), 3.11-3.30 (4H), 3.89 (3H), 4.25+4.55 (1H), 6.81 (1H), 8.05 (1H), 8.40 (1H), 8.49 (1H), 11.82 (1H) ppm.

Example 86a (RS)-4-Chloro-N-ethyl-N-isopropyl-5,6,7,8-tetrahydro[1]benzothieno[2,3-d]pyrimidine-7-carboxamide

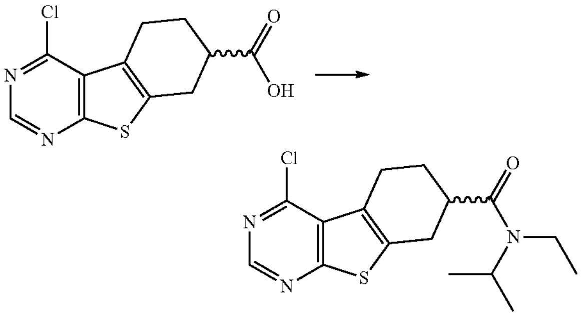

500 mg (1.86 mmol) (RS)-4-chloro-5,6,7,8-tetrahydro[1]benzothieno[2,3-d]pyrimidine-7-carboxylic acid (prepared according to intermediate example 31b) were transformed in analogy to example 3 using N-ethylpropan-2-amine to give after working up and purification 513 mg (82%) of the title compound.

Example 87

(RS)—N-(2-Methoxyethyl)-4-[(5-methoxy-2-oxo-2,3-dihydro-1,3-benzothiazol-6-yl)amino]-N-propyl-5,6,7,8-tetrahydro[1]benzothieno[2,3-d]pyrimidine-7-carboxamide

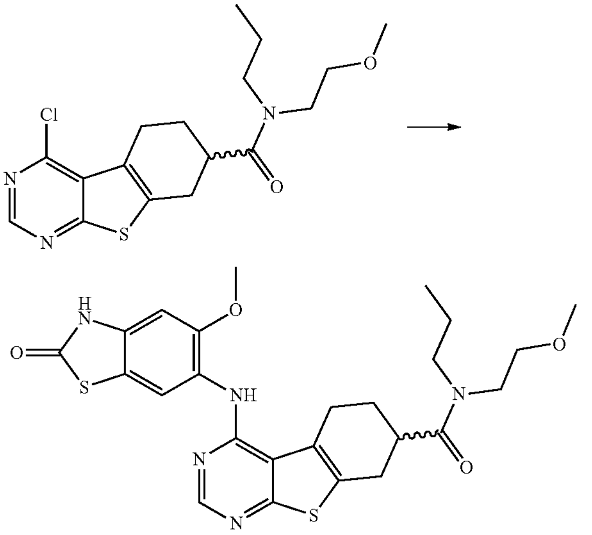

100 mg (272 μmol) (RS)-4-chloro-N-(2-methoxyethyl)-N-propyl-5,6,7,8-tetrahydro[1]benzothieno[2,3-d]pyrimidine-7-carboxamide (prepared according to intermediate example 87a) were transformed in analogy to example 1 using 6-amino-5-methoxy-1,3-benzothiazol-2(3H)-one to give after working up and purification 11.7 mg (8%) of the title compound.

$^{1}$H-NMR (DMSO-d6): δ=0.84 (3H), 1.52 (2H), 1.83 (1H), 2.07 (1H), 2.52-3.61 (11H), 3.25 (3H), 3.89 (3H), 6.81 (1H), 8.05 (1H), 8.40 (1H), 8.50 (1H), 11.80 (1H) ppm.

Example 87a (RS)-4-Chloro-N-(2-methoxyethyl)-N-propyl-5,6,7,8-tetrahydro[1]benzothieno[2,3-d]pyrimidine-7-carboxamide

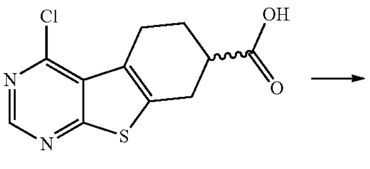

-continued

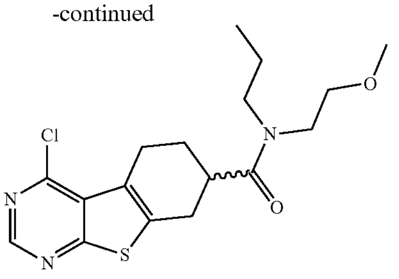

300 mg (1.16 mmol) (RS)-4-chloro-5,6,7,8-tetrahydro[1]benzothieno[2,3-d]pyrimidine-7-carboxylic acid (prepared according to intermediate example 31b) were transformed in analogy to example 3 using N-(2-methoxyethyl)propan-1-amine to give after working up and purification 293 mg (71%) of the title compound.

Example 88

(RS)—N-Butyl-N-(cyanomethyl)-4-[(5-methoxy-2-oxo-2,3-dihydro-1,3-benzothiazol-6-yl)amino]-5,6,7,8-tetrahydro[1]benzothieno[2,3-d]pyrimidine-7-carboxamide

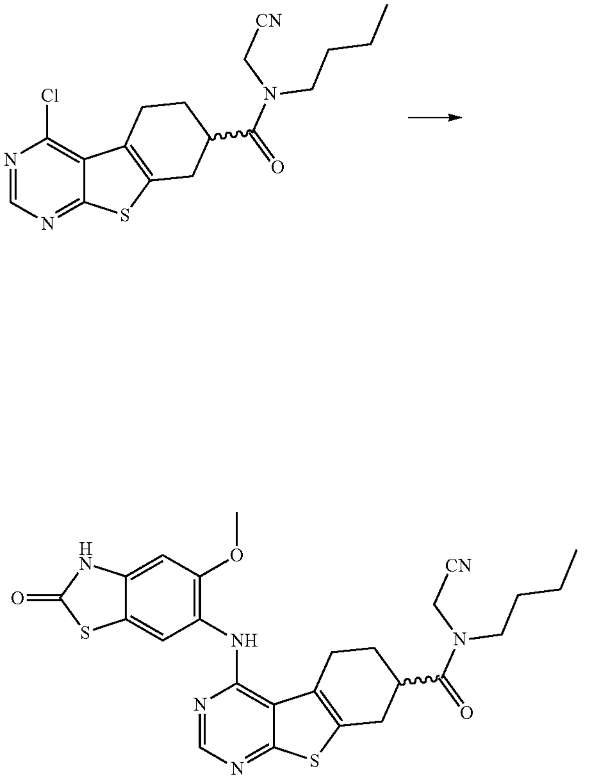

100 mg (276 μmol) (RS)—N-butyl-4-chloro-N-(cyanomethyl)-5,6,7,8-tetrahydro[1]benzothieno[2,3-d]pyrimidine-7-carboxamide (prepared according to intermediate example 88a) were transformed in analogy to example 1 using 6-amino-5-methoxy-1,3-benzothiazol-2(3H)-one to give after working up and purification 15.9 mg (10%) of the title compound.

$^1$H-NMR (DMSO-d6): δ=0.91 (3H), 1.30 (2H), 1.46-1.67 (2H), 1.86 (1H), 2.11 (1H), 2.95 (2H), 3.12-3.26 (3H), 3.51 (2H), 3.89 (3H), 4.38 (2H), 6.80 (1H), 8.04 (1H), 8.40 (1H), 8.47 (1H), 11.80 (1H) ppm.

Example 88a (RS)—N-Butyl-4-chloro-N-(cyanomethyl)-5,6,7,8-tetrahydro[1]benzothieno[2,3-d]pyrimidine-7-carboxamide

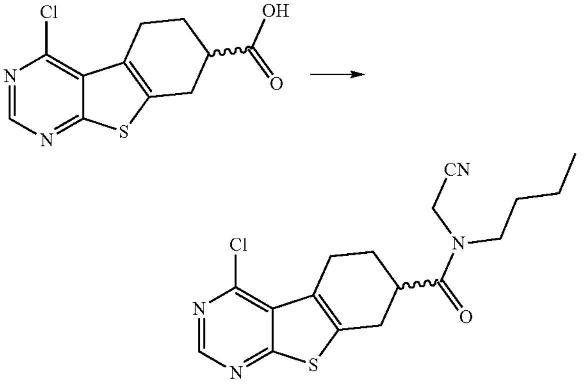

300 mg (1.12 mmol) (RS)-4-chloro-5,6,7,8-tetrahydro[1]benzothieno[2,3-d]pyrimidine-7-carboxylic acid (prepared according to intermediate example 31b) were transformed in analogy to example 3 using (butylamino)acetonitrile to give after working up and purification 280 mg (69%) of the title compound.

Example 89

(RS)—N-Butyl-4-[(5-methoxy-2-oxo-2,3-dihydro-1,3-benzothiazol-6-yl)amino]-N-methyl-5,6,7,8-tetrahydro[1]benzothieno[2,3-d]pyrimidine-7-carboxamide

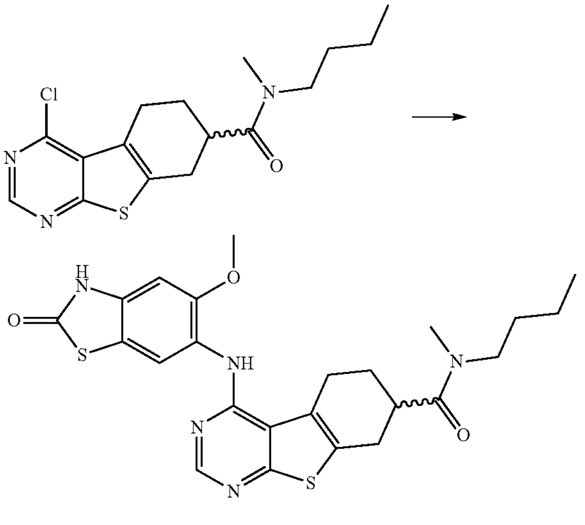

100 mg (296 μmol) (RS)—N-butyl-4-chloro-N-methyl-5,6,7,8-tetrahydro[1]benzothieno[2,3-d]pyrimidine-7-carboxamide (prepared according to intermediate example 89a) were transformed in analogy to example 1 using 6-amino-5-methoxy-1,3-benzothiazol-2(3H)-one to give after working up and purification 8.8 mg (6%) of the title compound.

$^1$H-NMR (DMSO-d6): δ=0.90 (3H), 1.26 (2H), 1.37-1.59 (2H), 1.81 (1H), 2.09 (1H), 2.81-3.45 (7H), 2.84+3.07 (3H), 3.89 (3H), 6.80 (1H), 8.04 (1H), 8.40 (1H), 8.47+8.50 (1H), 11.81 (1H) ppm.

Example 89a (RS)—N-Butyl-4-chloro-N-methyl-5,6,7,8-tetrahydro[1]benzothieno[2,3-d]pyrimidine-7-carboxamide

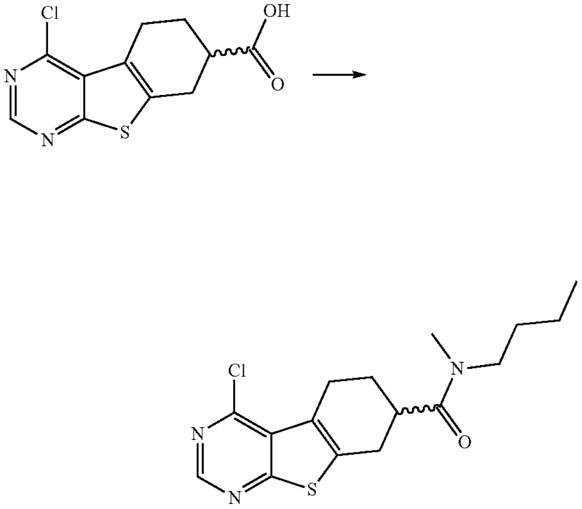 [SMILES: O=C(O)C1CCc2c(sc3ncnc(Cl)c23)C1 ; CCCCN(C)C(=O)C1CCc2c(sc3ncnc(Cl)c23)C1]

300 mg (1.12 mmol) (RS)-4-chloro-5,6,7,8-tetrahydro[1]benzothieno[2,3-d]pyrimidine-7-carboxylic acid (prepared according to intermediate example 31b) were transformed in analogy to example 3 using N-methylbutan-1-amine to give after working up and purification 249 mg (66%) of the title compound.

Example 90

(RS)—N-Ethyl-N-(2-methoxyethyl)-4-[(5-methoxy-2-oxo-2,3-dihydro-1,3-benzothiazol-6-yl)amino]-5,6,7,8-tetrahydro[1]benzothieno[2,3-d]pyrimidine-7-carboxamide

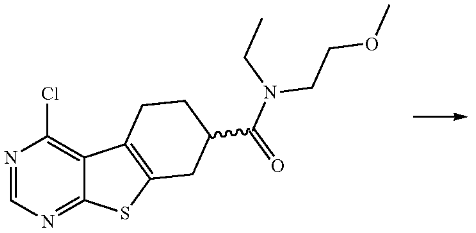

-continued

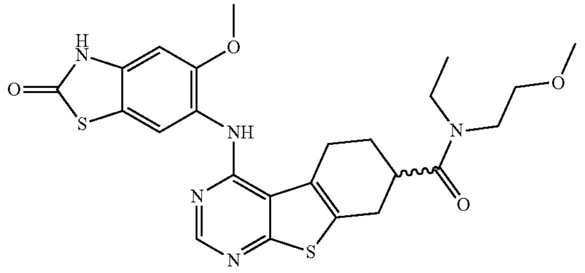

100 mg (283 μmol) (RS)-4-chloro-N-ethyl-N-(2-methoxyethyl)-5,6,7,8-tetrahydro[1]benzothieno[2,3-d]pyrimidine-7-carboxamide (prepared according to intermediate example 90a) were transformed in analogy to example 1 using 6-amino-5-methoxy-1,3-benzothiazol-2(3H)-one to give after working up and purification 11.0 mg (7%) of the title compound.

$^1$H-NMR (DMSO-d6): δ=1.03+1.14 (3H), 1.84 (1H), 2.07 (1H), 2.80-3.65 (11H), 3.25+3.26 (3H), 3.89 (3H), 6.80 (1H), 8.04 (1H), 8.40 (1H), 8.50 (1H), 11.81 (1H) ppm.

Example 90a (RS)-4-Chloro-N-ethyl-N-(2-methoxyethyl)-5,6,7,8-tetrahydro[1]benzothieno[2,3-d]pyrimidine-7-carboxamide

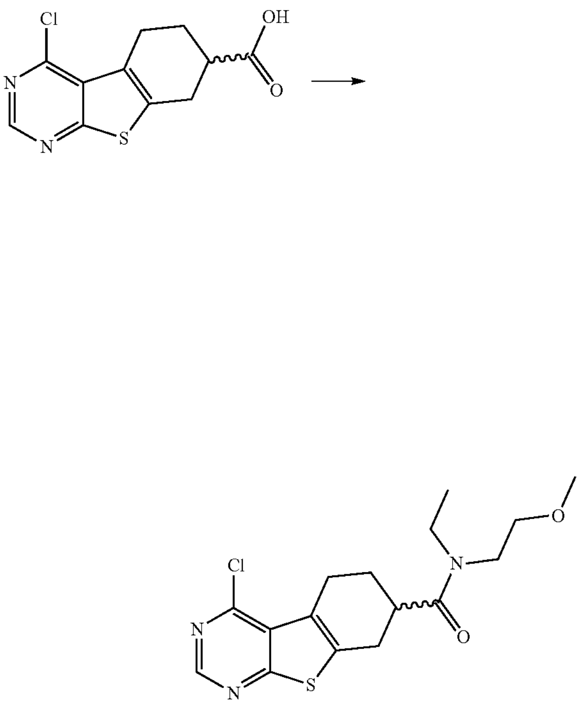

300 mg (1.12 mol) (RS)-4-chloro-5,6,7,8-tetrahydro[1]benzothieno[2,3-d]pyrimidine-7-carboxylic acid (prepared according to intermediate example 31b) were transformed in analogy to example 3 using N-ethyl-2-methoxyethanamine to give after working up and purification 317 mg (80%) of the title compound.

Example 91

(RS)-1-({4-[(2-Oxo-2,3-dihydro-1,3-benzothiazol-6-yl)amino]-5,6,7,8-tetrahydro[1]benzothieno[2,3-d]pyrimidin-7-yl}carbonyl)azetidine-3-carbonitrile

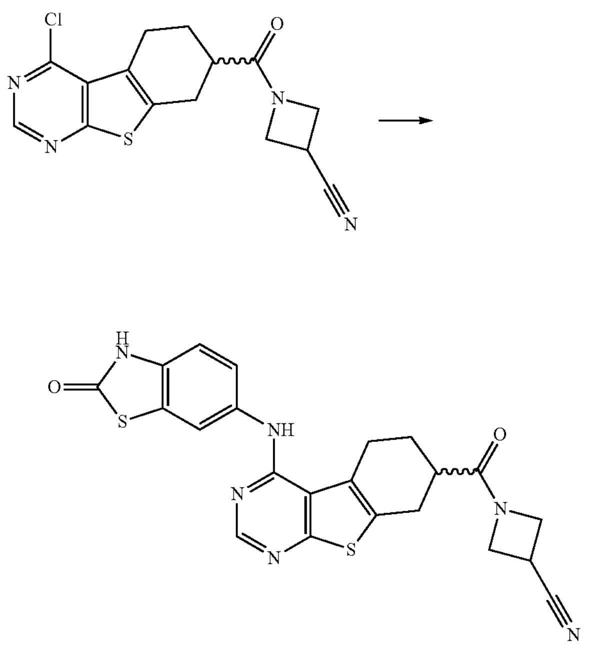

34 mg (102 μmol) (RS)-1-[(4-chloro-5,6,7,8-tetrahydro[1]benzothieno[2,3-d]pyrimidin-7-yl)carbonyl]azetidine-3-carbonitrile (prepared according to intermediate example 91a) were transformed in analogy to example 1 to give after working up and purification 25.6 mg (51%) of the title compound.

$^1$H-NMR (DMSO-d6): δ=1.75 (1H), 2.06 (1H), 2.68-3.24 (5H), 3.81 (1H), 4.04 (1H), 4.17 (1H), 4.40-4.64 (2H), 7.09 (1H), 7.44 (1H), 7.82 (1H), 8.17 (1H), 8.32 (1H), 11.81 (1H) ppm.

Example 91a (RS)-1-[(4-Chloro-5,6,7,8-tetrahydro[1]benzothieno[2,3-d]pyrimidin-7-yl)carbonyl]azetidine-3-carbonitrile

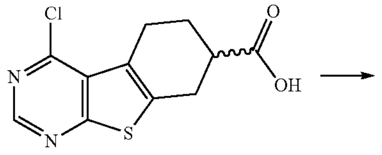

-continued

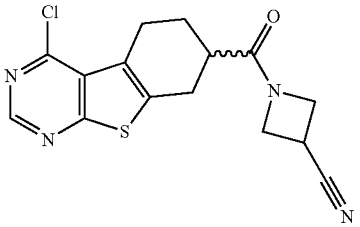

150 mg (558 μmol) (RS)-4-chloro-5,6,7,8-tetrahydro[1]benzothieno[2,3-d]pyrimidine-7-carboxylic acid (prepared according to intermediate example 31b) were transformed in analogy to example 3 using azetidine-3-carbonitrile to give after working up and purification 72 mg (39%) of the title compound.

Example 92

(RS)—N-Benzyl-N-[2-(dimethylamino)ethyl]-4-[(5-methoxy-2-oxo-2,3-dihydro-1,3-benzothiazol-6-yl)amino]-5,6,7,8-tetrahydro[1]benzothieno[2,3-d]pyrimidine-7-carboxamide

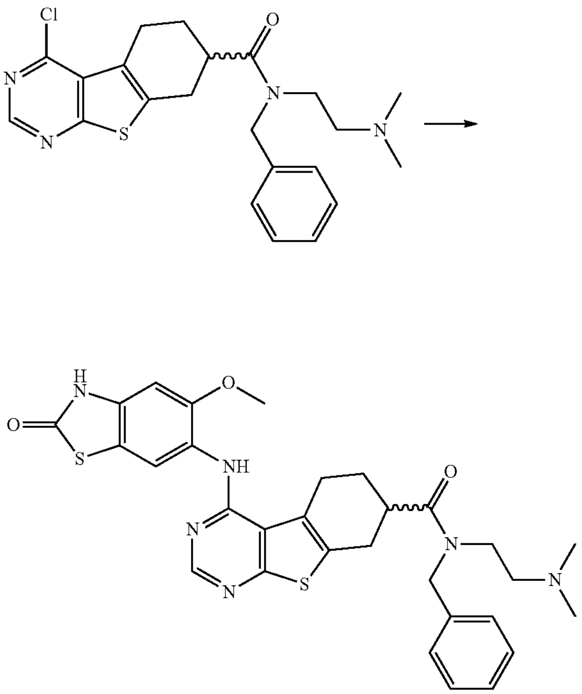 [SMILES: CN(C)CCN(Cc1ccccc1)C(=O)C1CCc2c(sc3ncnc(Cl)c23)C1 ; COc1cc2[nH]c(=O)sc2cc1Nc1ncnc2sc3c(c12)CCC(C(=O)N(CCN(C)C)Cc1ccccc1)C3]

146 mg (340 μmol) (RS)—N-benzyl-4-chloro-N-[2-(dimethylamino)ethyl]-5,6,7,8-tetrahydro[1]benzothieno[2,3-d]pyrimidine-7-carboxamide (prepared according to intermediate example 92a) were transformed in analogy to example 1 using 6-amino-5-methoxy-1,3-benzothiazol-2(3H)-one to give after working up and purification 8.4 mg (4%) of the title compound.

$^1$H-NMR (DMSO-d6): δ=1.76-2.03 (2H), 2.13 (6H), 2.17 (1H), 2.29-2.43 (2H), 2.79-3.55 (5H), 3.87+3.89 (3H), 4.48-4.83 (2H), 6.79 (2H), 7.22-7.41 (5H), 7.96+8.03 (1H), 8.37+8.40 (1H), 8.48+8.51 (1H), 11.77 (1H) ppm.

Example 92a (RS)—N-Benzyl-4-chloro-N-[2-(dimethylamino)ethyl]-5,6,7,8-tetrahydro[1]benzothieno[2,3-d]pyrimidine-7-carboxamide

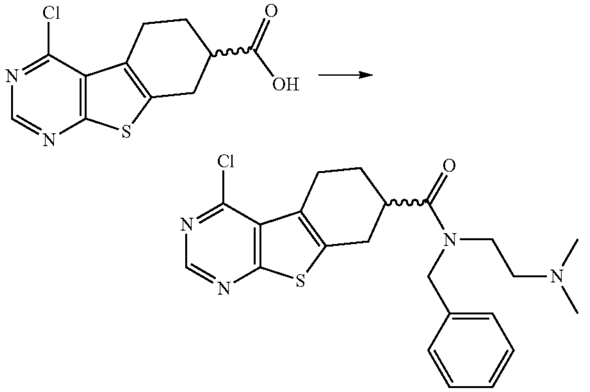

300 mg (1.12 mmol) (RS)-4-chloro-5,6,7,8-tetrahydro[1]benzothieno[2,3-d]pyrimidine-7-carboxylic acid (prepared according to intermediate example 31b) were transformed in analogy to example 3 using N'-benzyl-N,N-dimethylethane-1,2-diamine to give after working up and purification 152 mg (32%) of the title compound.

Example 93

(RS)—N,N-bis(2-methoxyethyl)-4-[(5-methoxy-2-oxo-2,3-dihydro-1,3-benzothiazol-6-yl)amino]-5,6,7,8-tetrahydro[1]benzothieno[2,3-d]pyrimidine-7-carboxamide

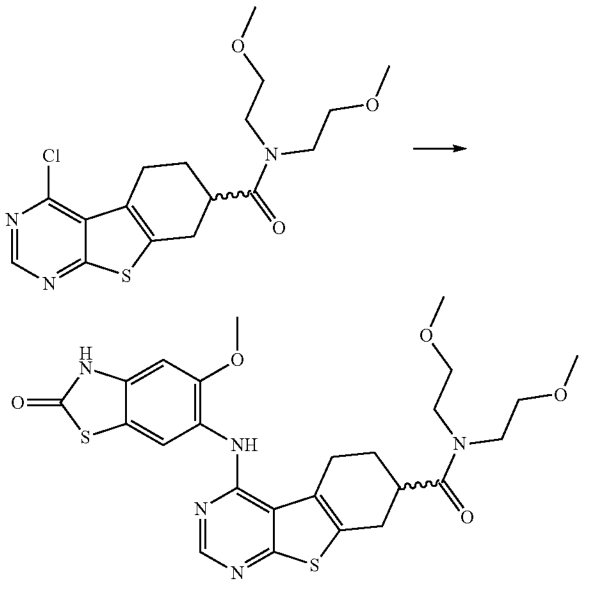

150 mg (391 μmol) (RS)-4-chloro-N,N-bis(2-methoxyethyl)-5,6,7,8-tetrahydro[1]benzothieno[2,3-d]pyrimidine-7-carboxamide (prepared according to intermediate example 93a) were transformed in analogy to example 1 using 6-amino-5-methoxy-1,3-benzothiazol-2(3H)-one to give after working up and purification 27.1 mg (12%) of the title compound.

$^1$H-NMR (DMSO-d6): δ=1.83 (1H), 2.08 (1H), 2.81-3.02 (2H), 3.05-3.22 (3H), 3.25 (3H), 3.26 (3H), 3.29-3.74 (9H), 3.89 (3H), 6.81 (1H), 8.05 (1H), 8.40 (1H), 11.80 (1H) ppm.

Example 92a (RS)-4-chloro-N,N-bis(2-methoxyethyl)-5,6,7,8-tetrahydro[1]benzothieno[2,3-d]pyrimidine-7-carboxamide

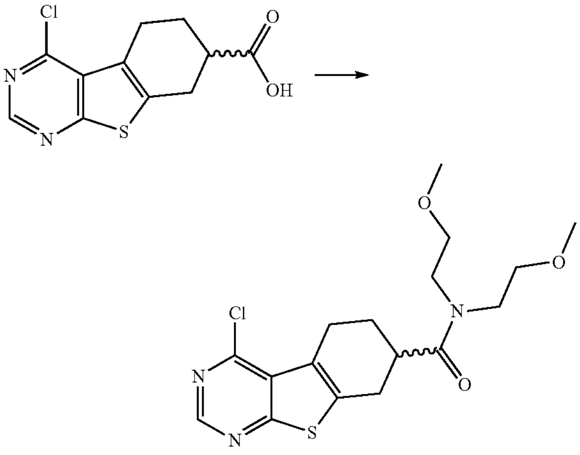

300 mg (1.12 mmol) (RS)-4-chloro-5,6,7,8-tetrahydro[1]benzothieno[2,3-d]pyrimidine-7-carboxylic acid (prepared according to intermediate example 31b) were transformed in analogy to example 3 using 2-methoxy-N-(2-methoxyethyl)ethanamine to give after working up and purification 340 mg (79%) of the title compound.

Example 94

(RS)-6-{[7-(1-Oxa-6-azaspiro[3.3]hept-6-ylcarbonyl)-5,6,7,8-tetrahydro[1]benzothieno[2,3-d]pyrimidin-4-yl]amino}-1,3-benzothiazol-2(3H)-one

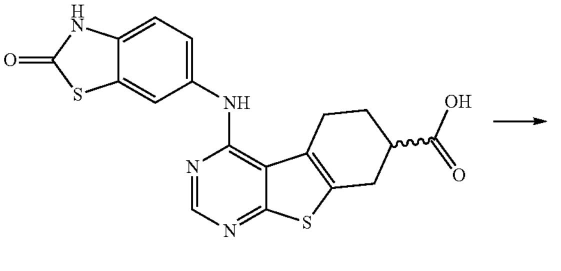

-continued

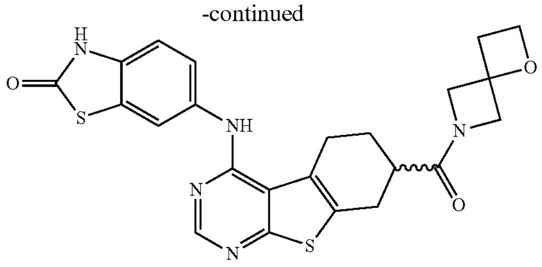

50 mg (125 μmol) (RS)-4-[(2-oxo-2,3-dihydro-1,3-benzothiazol-6-yl)amino]-5,6,7,8-tetrahydro[1]benzothieno[2,3-d]pyrimidine-7-carboxylic acid (prepared according to example 2) were transformed in analogy to example 3 using 1-oxa-6-azaspiro[3.3]heptane ethanedioate (1:1) to give after working up and purification 31.7 mg (50%) of the title compound.

$^1$H-NMR (DMSO-d6): δ=1.74 (1H), 2.03 (1H), 2.74 (1H), 2.79-2.94 (4H), 3.06-3.17 (1H), 3.23 (1H), 3.95 (1H), 4.13 (1H), 4.29-4.53 (4H), 7.09 (1H), 7.44 (1H), 7.82 (1H), 8.16 (1H), 8.32 (1H), 11.83 (1H) ppm.

Further, the compounds of formula I of the present invention can be converted to any salt as described herein, by any method which is known to the person skilled in the art. Similarly, any salt of a compound of formula I of the present invention can be converted into the free compound, by any method which is known to the person skilled in the art.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease. Therefore, the present invention includes pharmaceutical compositions that are comprised of a pharmaceutically acceptable carrier and a pharmaceutically effective amount of a compound, or salt thereof, of the present invention. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is preferably that amount which produces a result or exerts an influence on the particular condition being treated. The compounds of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC—CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution:

A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilised Powder for IV Administration:

A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular Suspension:

The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules:

A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules:

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets:

A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules:

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Combination Therapies

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The compounds of this invention can be administered as the sole pharmaceutical agent or in combination with one or more other pharmaceutical agents where the combination causes no unacceptable adverse effects. The present invention relates also to such combinations. For example, the compounds of this invention can be combined with known chemotherapeutic agents or anti-cancer agents, e.g. anti-hyperproliferative or other indication agents, and the like, as well as with admixtures and combinations thereof. Other indication agents include, but are not limited to, anti-angiogenic agents, mitotic inhibitors, alkylating agents, anti-metabolites, DNA-intercalating antibiotics, growth factor inhibitors, cell cycle inhibitors, enzyme inhibitors, toposisomerase inhibitors, biological response modifiers, or anti-hormones.

The term "(chemotherapeutic) anti-cancer agents", includes but is not limited to 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin.

In a preferred embodiment, a compound of general formula (I) as defined herein is administered in combination with one or more inhibitors of the PI3K-AKT-mTOR pathway. Examples of inhibitors of the mammalian Target of Rapamycin (mTOR) are Afinitor, Votubia (everolimus).

Generally, the use of cytotoxic and/or cytostatic agents in combination with a compound or composition of the present invention will serve to:

(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent combinations produce antagonistic effects.

Methods of Sensitizing Cells to Radiation

In a distinct embodiment of the present invention, a compound of the present invention may be used to sensitize a cell to radiation. That is, treatment of a cell with a compound of the present invention prior to radiation treatment of the cell renders the cell more susceptible to DNA damage and cell death than the cell would be in the absence of any treatment with a compound of the invention. In one aspect, the cell is treated with at least one compound of the invention.

Thus, the present invention also provides a method of killing a cell, wherein a cell is administered one or more compounds of the invention in combination with conventional radiation therapy.

The present invention also provides a method of rendering a cell more susceptible to cell death, wherein the cell is treated with one or more compounds of the invention prior to the treatment of the cell to cause or induce cell death. In one aspect, after the cell is treated with one or more compounds of the invention, the cell is treated with at least one compound, or at least one method, or a combination thereof, in order to cause DNA damage for the purpose of inhibiting the function of the normal cell or killing the cell.

In one embodiment, a cell is killed by treating the cell with at least one DNA damaging agent. That is, after treating a cell with one or more compounds of the invention to sensitize the cell to cell death, the cell is treated with at least one DNA damaging agent to kill the cell. DNA damaging agents useful in the present invention include, but are not limited to, chemotherapeutic agents (e.g., cisplatinum), ionizing radiation (X-rays, ultraviolet radiation), carcinogenic agents, and mutagenic agents.

In another embodiment, a cell is killed by treating the cell with at least one method to cause or induce DNA damage. Such methods include, but are not limited to, activation of a cell signalling pathway that results in DNA damage when the pathway is activated, inhibiting of a cell signalling pathway that results in DNA damage when the pathway is inhibited, and inducing a biochemical change in a cell, wherein the change results in DNA damage. By way of a non-limiting example, a DNA repair pathway in a cell can be inhibited, thereby preventing the repair of DNA damage and resulting in an abnormal accumulation of DNA damage in a cell.

In one aspect of the invention, a compound of the invention is administered to a cell prior to the radiation or other induction of DNA damage in the cell. In another aspect of the invention, a compound of the invention is administered to a cell concomitantly with the radiation or other induction of DNA damage in the cell. In yet another aspect of the invention, a compound of the invention is administered to a cell immediately after radiation or other induction of DNA damage in the cell has begun.

In another aspect, the cell is in vitro. In another embodiment, the cell is in vivo.

As mentioned supra, the compounds of the present invention have surprisingly been found to effectively inhibit MKNK-1 and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

In accordance with another aspect therefore, the present invention covers a compound of general formula I, or a stereoisomer, a tautomer, an N-oxide, a hydrate, a solvate, or a salt thereof, particularly a pharmaceutically acceptable salt thereof, or a mixture of same, as described and defined herein, for use in the treatment or prophylaxis of a disease, as mentioned supra.

Another particular aspect of the present invention is therefore the use of a compound of general formula I, described supra, or a stereoisomer, a tautomer, an N-oxide, a hydrate, a solvate, or a salt thereof, particularly a pharmaceutically acceptable salt thereof, or a mixture of same, for the prophylaxis or treatment of a disease.

Another particular aspect of the present invention is therefore the use of a compound of general formula I described supra for manufacturing a pharmaceutical composition for the treatment or prophylaxis of a disease.

The diseases referred to in the two preceding paragraphs are diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK-1, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, wherein the diseases are haemotological tumours, solid tumours and/or metastases thereof.

Method of Treating Hyper-Proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophtalmic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opthalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death or apoptosis of such cell types.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Preferably, the diseases of said method are haematological tumours, solid tumour and/or metastases thereof.

The compounds of the present invention can be used in particular in therapy and prevention, i.e. prophylaxis, of tumour growth and metastases, especially in solid tumours of all indications and stages with or without pre-treatment of the tumour growth.

Methods of testing for a particular pharmacological or pharmaceutical property are well known to persons skilled in the art.

The example testing experiments described herein serve to illustrate the present invention and the invention is not limited to the examples given.

Biological Assays

Examples were tested in selected biological assays one or more times. When tested more than once, data are reported as either average values or as median values, wherein

- the average value, also referred to as the arithmetic mean value, represents the sum of the values obtained divided by the number of times tested, and
- the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values or median values calculated utilizing data sets obtained from testing of one or more synthetic batch.

MKNK1 Kinase Assay

MKNK1-inhibitory activity of compounds of the present invention was quantified employing the MKNK1 TR-FRET assay as described in the following paragraphs.

A recombinant fusion protein of Glutathione-S-Transferase (GST, N-terminally) and human full-length MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (C-terminus in amide form) was used which can be purchased e.g. form the company Biosyntan (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 μL of a solution of MKNK1 in aqueous assay buffer [50 mM HEPES pH 7.5, 5 mM $MgCl_2$, 1.0 mM dithiothreitol, 0.005% (v/v) Nonidet-P40 (Sigma)] was added and the mixture was incubated for 15 min at 22° C. to allow pre-binding of the test compounds to the enzyme before the start of the kinase reaction. Then the kinase reaction was started by the addition of 3 μL of a solution of adenosine-tri-phosphate (ATP, 16.7 μM=>final conc. in the 5 μL assay volume is 10 μM) and substrate (0.1 μM=>final conc. in the 5 μL assay volume is 0.06 μM) in assay buffer and the resulting mixture was incubated for a reaction time of 45 min at 22° C. The concentration of MKNK1 was adjusted depending of the activity of the enzyme lot and was chosen appropriate to have the assay in the linear range, typical concentrations were in the range of 0.05 μg/ml. The reaction was stopped by the addition of 5 μL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and IC50 values were calculated by a 4 parameter fit using an inhouse software.

MKNK1 Kinase High ATP Assay

MKNK1-inhibitory activity at high ATP of compounds of the present invention after their preincubation with MKNK1 was quantified employing the TR-FRET-based MKNK1 high ATP assay as described in the following paragraphs.

A recombinant fusion protein of Glutathione-S-Transferase (GST, N-terminally) and human full-length MKNK1 (amino acids 1-424 and T344D of accession number BAA 19885.1), expressed in insect cells using baculovirus expression system and purified via glutathione sepharose affinity chromatography, was purchased from Carna Biosciences (product no 02-145) and used as enzyme. As substrate for the kinase reaction the biotinylated peptide biotin-Ahx-IKKRKLTRRKSLKG (C-terminus in amide form) was used, which can be purchased e.g. from the company Biosyntan (Berlin-Buch, Germany).

For the assay 50 nL of a 100 fold concentrated solution of the test compound in DMSO was pipetted into a black low volume 384 well microtiter plate (Greiner Bio-One, Frickenhausen, Germany), 2 μL of a solution of MKNK1 in aqueous assay buffer [50 mM HEPES pH 7.5, 5 mM $MgCl_2$, 1.0 mM dithiothreitol, 0.005% (v/v) Nonidet-P40 (Sigma)] was added and the mixture was incubated for 15 min at 22° C. to allow pre-binding of the test compounds to the enzyme before the start of the kinase reaction. Then the kinase reaction was started by the addition of 3 μL of a solution of adenosine-tri-phosphate (ATP, 3.3 mM=>final conc. in the 5 μL assay volume is 2 mM) and substrate (0.1 μM=>final conc. in the 5 μL assay volume is 0.06 μM) in assay buffer and the resulting mixture was incubated for a reaction time of 30 min at 22° C. The concentration of MKNK1 was adjusted depending of the activity of the enzyme lot and was chosen appropriate to have the assay in the linear range, typical concentrations were in the range of 0.003 μg/mL. The reaction was stopped by the addition of 5 μL of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL. Therefore, the fluorescence emissions at 620 nm and 665 nm after excitation at 350 nm were measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and IC50 values were calculated by a 4 parameter fit using an inhouse software. Data are presented in Table 2.

TABLE 2

| Example | MKNK1 $IC_{50}$ [nM] |
|---|---|
| 1 | 47 |
| 2 | 108 |
| 3 | 39 |
| 4 | 57 |
| 5 | 36 |
| 6 | 40 |
| 7 | 42 |
| 8 | 33 |
| 9 | 9 |
| 10 | 11 |
| 11 | 91 |
| 12 | 48 |
| 13 | 41 |
| 14 | 25 |
| 15 | 85 |
| 16 | 304 |
| 17 | 128 |
| 18 | 60 |
| 19 | 93 |
| 20 | 103 |
| 21 | 37 |
| 22 | 59 |
| 23 | 43 |
| 24 | 62 |
| 25 | 42 |
| 26 | 84 |
| 27 | 100 |
| 28 | 139 |
| 29 | 48 |
| 30 | 15 |
| 31 | 4 |
| 32 | 92 |
| 33 | 42 |
| 34 | 20 |
| 35 | 36 |
| 36 | 9 |
| 37 | 22 |
| 38 | 44 |
| 39 | nd |
| 40 | 65 |
| 41 | 21 |
| 42 | 47 |
| 43 | 69 |
| 44 | 67 |
| 45 | 70 |
| 46 | 35 |
| 47 | 47 |
| 48 | 65 |
| 49 | 45 |
| 50 | 43 |
| 51 | 75 |
| 52 | 30 |
| 53 | 52 |
| 54 | 28 |
| 55 | 72 |
| 56 | 27 |
| 57 | 39 |
| 58 | 63 |
| 59 | 40 |
| 60 | 36 |
| 61 | 32 |
| 62 | 40 |
| 63 | 38 |
| 64 | 27 |
| 65 | 81 |
| 66 | 34 |
| 67 | 62 |
| 68 | 32 |
| 69 | 19 |
| 70 | 24 |
| 71 | 47 |
| 72 | 44 |
| 73 | 34 |
| 74 | 47 |
| 75 | 32 |
| 76 | 54 |
| 77 | 41 |
| 78 | 34 |
| 79 | 38 |
| 80 | 42 |
| 81 | 34 |
| 82 | 46 |
| 83 | 52 |
| 84 | 30 |
| 85 | 4 |
| 86 | 3 |
| 87 | 2.0 |
| 88 | 1.0 |
| 89 | 1.9 |
| 90 | 1.0 |
| 91 | 38.7 |
| 92 | 0.6 |
| 93 | 0.7 |

Mnk2 Kinase High ATP Assay

Mnk2-inhibitory activity at high ATP of compounds of the present invention after their preincubation with Mnk2 was quantified employing the TR-FRET-based Mnk2 high ATP assay as described in the following paragraphs.

A recombinant fusion protein of Glutathione-S-Transferase (GST, N-terminally) and human full-length Mnk2 (Genbank accession number NP_060042.2), expressed in insect cells using baculovirus expression system, purified via glutathione sepharose affinity chromatography, and activated in vitro with MAPK12, was purchased from Invitrogen (product no PV5608) and used as enzyme. As substrate for the kinase reaction the biotinylated peptide biotin-Ahx-IKKRKLTRRKSLKG (C-terminus in amide form) was used which can be purchased e.g. form the company Biosyntan (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 μl of a solution of Mnk2 in aqueous assay buffer [50 mM HEPES pH 7.5, 5 mM $MgCl_2$, 1.0 mM dithiothreitol, 0.005% (v/v) Nonidet-P40 (G-Biosciences, St. Louis, USA)] was added and the mixture was incubated for 15 min at 22° C. to allow pre-binding of the test compounds to the enzyme before the start of the kinase reaction. Then the kinase reaction was started by the addition of 3 μl of a solution of adenosine-tri-phosphate (ATP, 3.3 mM=>final conc. in the 5 μl assay volume is 2 mM) and substrate (0.1 μM=>final conc. in the 5 μl assay volume is 0.06 μM) in assay buffer and the resulting mixture was incubated for a reaction time of 30 min at 22° C. The concentration of Mnk2 was adjusted depending of the activity of the enzyme lot and was chosen appropriate to have the assay in the linear range, typical concentrations were in the range of 0.0045 μg/ml. The reaction was stopped by the addition of 5 μl of a solution of TR-FRET detection reagents (5 nM streptavidine-XL665 [Cisbio Bioassays, Codolet, France] and 1 nM anti-ribosomal protein S6 (pSer236)-antibody from Invitrogen [#44921G] and 1 nM LANCE EU-W1024 labeled ProteinG [Perkin-Elmer, product no. AD0071]) in an aqueous EDTA-solution (100 mM EDTA, 0.1% (w/v) bovine serum albumin in 50 mM HEPES pH 7.5).

The resulting mixture was incubated for 1 h at 22° C. to allow the formation of complex between the phosphorylated biotinylated peptide and the detection reagents. Subsequently the amount of phosphorylated substrate was evaluated by measurement of the resonance energy transfer from the Eu-chelate to the streptavidine-XL665. Therefore, the fluorescence emissions at 620 nm and 665 nm after excitation at 350 nm were measured in a TR-FRET reader, e.g. a Pherastar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Usually the test compounds were tested on the same microtiterplate in 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and 1050 values were calculated by a 4 parameter fit using an inhouse software.

EGFR Kinase Assay

EGFR inhibitory activity of compounds of the present invention can be quantified employing the TR-FRET based EGFR assay as described in the following paragraphs.

Epidermal Growth Factor Receptor (EGFR) affinity purified from human carcinoma A431 cells (Sigma-Aldrich, # E3641) is used as kinase. As substrate for the kinase reaction the biotinylated peptide biotin-Ahx-AEEEEYFELVAKKK (C-terminus in amid form) is used which can be purchased e.g. form the company Biosynthan GmbH (Berlin-Buch, Germany).

For the assay 50 nL of a 100 fold concentrated solution of the test compound in DMSO is pipetted into a black low volume 384 well microtiter plate (Greiner Bio-One, Frickenhausen, Germany), 2 μL of a solution of EGFR in aqueous assay [50 mM Hepes/HCl pH 7.0, 1 mM $MgCl_2$, 5 mM $MnCl_2$, 0.5 mM activated sodium ortho-vanadate, 0.005% (v/v) Tween-20] are added and the mixture is incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (1.67 μM=>final conc. in the 5 μL assay volume is 1 μM) in assay buffer and the resulting mixture is incubated for a reaction time of 30 min at 22° C. The concentration of EGFR is adjusted depending of the activity of the enzyme lot and is chosen appropriate to have the assay in the linear range, typical concentration are in the range of 3 U/ml. The reaction is stopped by the addition of 5 μl of a solution of HTRF detection reagents (0.1 μM streptavidine-XL665 [Cis Biointernational] and 1 nM PT66-Tb-Chelate, an terbium-chelate labelled anti-phospho-tyrosine antibody from Cis Biointernational [instead of the PT66-Tb-chelate PT66-Eu-Cryptate from Perkin Elmer can also be used]) in an aqueous EDTA-solution (80 mM EDTA, 0.2% (w/v) bovine serum albumin in 50 mM HEPES pH 7.5).

The resulting mixture is incubated 1 h at 22° C. to allow the binding of the biotinylated phosphorylated peptide to the streptavidine-XL665 and the PT66-Eu-Chelate. Subsequently the amount of phosphorylated substrate is evaluated by measurement of the resonance energy transfer from the PT66-Eu-Chelate to the streptavidine-XL665. Therefore, the fluorescence emissions at 620 nm and 665 nm after excitation at 337 nm are measured in a HTRF reader, e.g. a Pherastar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Usually the test compounds are tested on the same microtiterplate in 11 different concentrations in the range of 20 μM to 0.1 nM (e.g. 20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial dilutions, the exact concentrations may vary depending on the pipettor used) in duplicate values for each concentration and $IC_{50}$ values are calculated by a 4 parameter fit using an inhouse software.

CDK2/CycE Kinase Assay

CDK2/CycE-inhibitory activity of compounds of the present invention is quantified employing the CDK2/CycE TR-FRET assay as described in the following paragraphs.

Recombinant fusion proteins of GST and human CDK2 and of GST and human CycE, expressed in insect cells (Sf9) and purified by Glutathion-Sepharose affinity chromatography, are purchased from ProQinase GmbH (Freiburg, Germany). As substrate for the kinase reaction biotinylated peptide biotin-Ttds-YISPLKSPYKISEG (C-terminus in amid form) is used which can be purchased e.g. form the company JERINI peptide technologies (Berlin, Germany).

For the assay 50 nL of a 100 fold concentrated solution of the test compound in DMSO is pipetted into a black low volume 384 well microtiter plate (Greiner Bio-One, Frickenhausen, Germany), 2 μL of a solution of CDK2/CycE in aqueous assay buffer [50 mM Tris/HCl pH 8.0, 10 mM $MgCl_2$, 1.0 mM dithiothreitol, 0.1 mM sodium ortho-vanadate, 0.01% (v/v) Nonidet-P40 (Sigma)] are added and the mixture is incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (1.25 μM=>final conc. in the 5 μL assay volume is 0.75 μM) in assay buffer and the resulting mixture is incubated for a reaction time of 25 min at 22° C. The concentration of CDK2/CycE is adjusted depending of the activity of the enzyme lot and is chosen appropriate to have the assay in the linear range, typical concentrations are in the range of 130 ng/ml. The reaction is stopped by the addition of 5 μL of a solution of TR-FRET detection reagents (0.2 μM streptavidine-XL665 [Cisbio Bioassays, Codolet, France] and 1 nM anti-RB(pSer807/pSer811)-antibody from BD Pharmingen [#558389] and 1.2 nM LANCE EU-W1024 labeled anti-mouse IgG antibody [Perkin-Elmer, product no. AD0077, as an alternative a Terbium-cryptate-labeled anti-mouse IgG antibody from Cisbio Bioassays can be used]) in an aqueous EDTA-solution (100 mM EDTA, 0.2% (w/v) bovine serum albumin in 100 mM HEPES/NaOH pH 7.0).

The resulting mixture is incubated 1 h at 22° C. to allow the formation of complex between the phosphorylated biotinylated peptide and the detection reagents. Subsequently the amount of phosphorylated substrate is evaluated by measurement of the resonance energy transfer from the Eu-chelate to the streptavidine-XL. Therefore, the fluorescence emissions at 620 nm and 665 nm after excitation at 350 nm is measured in a TR-FRET reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Usually the test compounds are tested on the same microtiterplate in 11 different concentrations in the range of 20 μM to 0.1 nM (20 μM, 5.9 μM, 1.7 μM, 0.51 μM, 0.15 μM, 44 nM, 13 nM, 3.8 nM, 1.1 nM, 0.33 nM and 0.1 nM, the dilution series prepared separately before the assay on the level of the 100 fold concentrated solutions in DMSO by serial 1:3.4 dilutions) in duplicate values for each concentration and 1050 values are calculated by a 4 parameter fit using an inhouse software.

PDGFRβ Kinase Assay

PDGFRβ inhibitory activity of compounds of the present invention is quantified employing the PDGFRβ HTRF assay as described in the following paragraphs.

As kinase, a GST-His fusion protein containing a C-terminal fragment of human PDGFRβ (amino acids 561-1106, expressed in insect cells [SF9] and purified by affinity chromatography, purchased from Proqinase [Freiburg i.Brsg., Germany] is used. As substrate for the kinase reaction the biotinylated poly-Glu,Tyr (4:1) copolymer (#61GT0BLA) from Cis Biointernational (Marcoule, France) is used.

For the assay 50 nL of a 100 fold concentrated solution of the test compound in DMSO is pipetted into a black low volume 384 well microtiter plate (Greiner Bio-One, Frickenhausen, Germany), 2 μL of a solution of PDGFRβ in aqueous assay buffer [50 mM HEPES/NaOH pH 7.5, 10 mM $MgCl_2$, 2.5 mM dithiothreitol, 0.01% (v/v) Triton-X100 (Sigma)] are added and the mixture was incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (2.27 μg/ml=>final conc. in the 5 μL assay volume is 1.36 μg/ml [~30 nM]) in assay buffer and the resulting mixture is incubated for a reaction time of 25 min at 22° C. The concentration of PDGFRβ in the assay is adjusted depending of the activity of the enzyme lot and is chosen appropriate to have the assay in the linear range, typical enzyme concentrations are in the range of about 125 pg/μL (final conc. in the 5 μL assay volume). The reaction is stopped by the addition of 5 μL of a solution of HTRF detection reagents (200 nM streptavidine-XLent [Cis Biointernational] and 1.4 nM PT66-Eu-Chelate, an europium-chelate labelled anti-phospho-tyrosine antibody from Perkin Elmer [instead of the PT66-Eu-chelate PT66-Tb-Cryptate from Cis Biointernational can also be used]) in an aqueous EDTA-solution (100 mM EDTA, 0.2% (w/v) bovine serum albumin in 50 mM HEPES/NaOH pH 7.5).

The resulting mixture is incubated 1 h at 22° C. to allow the binding of the biotinylated phosphorylated peptide to the streptavidine-XLent and the PT66-Eu-Chelate. Subsequently the amount of phosphorylated substrate is evaluated by measurement of the resonance energy transfer from the PT66-Eu-Chelate to the streptavidine-XLent. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compound are tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values are calculated by a 4 parameter fit using an inhouse software.

Fyn Kinase Assay

C-terminally His6-tagged human recombinant kinase domain of the human T-Fyn expressed in baculovirus infected insect cells (purchased from Invitrogen, P3042) is used as kinase. As substrate for the kinase reaction the biotinylated peptide biotin-KVEKIGEGTYGVV (C-terminus in amid form) is used which can be purchased e.g. form the company Biosynthan GmbH (Berlin-Buch, Germany).

For the assay 50 nL of a 100 fold concentrated solution of the test compound in DMSO is pipetted into a black low volume 384 well microtiter plate (Greiner Bio-One, Frickenhausen, Germany), 2 μL of a solution of T-Fyn in aqueous assay buffer [25 mM Tris/HCl pH 7.2, 25 mM $MgCl_2$, 2 mM dithiothreitol, 0.1% (w/v) bovine serum albumin, 0.03% (v/v) Nonidet-P40 (Sigma)]. are added and the mixture is incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (2 μM=>final conc. in the 5 μL assay volume is 1.2 μM) in assay buffer and the resulting mixture is incubated for a reaction time of 60 min at 22° C. The concentration of Fyn is adjusted depending of the activity of the enzyme lot and is chosen appropriate to have the assay in the linear range, typical concentration was 0.13 nM. The reaction is stopped by the addition of 5 μL of a solution of HTRF detection reagents (0.2 μM streptavidine-XL [Cisbio Bioassays, Codolet, France) and 0.66 nM PT66-Eu-Chelate, an europium-chelate labelled anti-phospho-tyrosine antibody from Perkin Elmer [instead of the PT66-Eu-chelate PT66-Tb-Cryptate from Cisbio Bioassays can also be used]) in an aqueous EDTA-solution (125 mM EDTA, 0.2% (w/v) bovine serum albumin in 50 mM HEPES/NaOH pH 7.0).

The resulting mixture is incubated 1 h at 22° C. to allow the binding of the biotinylated phosphorylated peptide to the streptavidine-XL and the PT66-Eu-Chelate. Subsequently the amount of phosphorylated substrate is evaluated by measurement of the resonance energy transfer from the PT66-Eu-Chelate to the streptavidine-XL. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compounds are tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and 1050 values are calculated by a 4 parameter fit using an inhouse software.

Flt4 Kinase Assay

Flt4 inhibitory activity of compounds of the present invention can be quantified employing the Flt4 TR-FRET assay as described in the following paragraphs.

As kinase, a GST-His fusion protein containing a C-terminal fragment of human Flt4 (amino acids 799-1298, expressed in insect cells [SF9] and purified by affinity chromatography, purchased from Proqinase [Freiburg i.Brsg., Germany] is used. As substrate for the kinase reaction the biotinylated peptide Biotin-Ahx-GGEEEEYFELVKKKK (C-terminus in amide form, purchased from Biosyntan, Berlin-Buch, Germany) is used.

For the assay 50 nL of a 100 fold concentrated solution of the test compound in DMSO is pipetted into a black low volume 384 well microtiter plate (Greiner Bio-One, Frickenhausen, Germany), 2 μL of a solution of Flt4 in aqueous assay buffer [25 mM HEPES pH 7.5, 10 mM $MgCl_2$, 2 mM dithiothreitol, 0.01% (v/v) Triton-X100 (Sigma), 0.5 mM EGTA, and 5 mM β-phospho-glycerol] are added and the mixture is incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (1.67 μM=>final conc. in the 5 μL assay volume is 1 μM) in assay buffer and the resulting mixture is incubated for a reaction time of 45 min at 22° C. The concentration of Flt4 in the assay is adjusted depending of the activity of the enzyme lot and is chosen appropriate to have the assay in the linear range, typical enzyme concentrations are in the range of about 120 pg/μL (final conc. in the 5 μL assay volume). The reaction is stopped by the addition of 5 μL of a solution of HTRF detection reagents (200 nM streptavidine-XL665 [Cis Biointernational] and 1 nM PT66-Tb-Cryptate, an terbium-cryptate labelled anti-phospho-tyrosine antibody from Cisbio Bioassays (Codolet, France) in an aqueous EDTA-solution (50 mM EDTA, 0.2% (w/v) bovine serum albumin in 50 mM HEPES pH 7.5).

The resulting mixture is incubated 1 h at 22° C. to allow the binding of the biotinylated phosphorylated peptide to the streptavidine-XL665 and the PT66-Tb-Cryptate. Subsequently the amount of phosphorylated substrate is evaluated by measurement of the resonance energy transfer from the PT66-Tb-Cryptate to the streptavidine-XL665. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compound are tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and 1050 values are calculated by a 4 parameter fit using an inhouse software.

TrkA Kinase Assay

TrkA inhibitory activity of compounds of the present invention can be quantified employing the TrkA HTRF assay as described in the following paragraphs.

As kinase, a GST-His fusion protein containing a C-terminal fragment of human TrkA (amino acids 443-796, expressed in insect cells [SF9] and purified by affinity chromatography, purchased from Proqinase [Freiburg i.Brsg., Germany] is used. As substrate for the kinase reaction the biotinylated poly-Glu,Tyr (4:1) copolymer (#61GT0BLA) from Cis Biointernational (Marcoule, France) is used.

For the assay 50 nL of a 100 fold concentrated solution of the test compound in DMSO is pipetted into a black low volume 384 well microtiter plate (Greiner Bio-One, Frickenhausen, Germany), 2 μL of a solution of TrkA in aqueous assay buffer [8 mM MOPS/HCl pH 7.0, 10 mM $MgCl_2$, 1 mM dithiothreitol, 0.01% (v/v) NP-40 (Sigma), 0.2 mM EDTA] are added and the mixture was incubated for 15 min at 22° C. to allow pre-binding of the test compounds to the enzyme before the start of the kinase reaction. Then the kinase reaction is started by the addition of 3 μL of a solution of adenosine-tri-phosphate (ATP, 16.7 μM=>final conc. in the 5 μL assay volume is 10 μM) and substrate (2.27 μg/ml=>final conc. in the 5 μL assay volume is 1.36 μg/ml [~30 nM]) in assay buffer and the resulting mixture is incubated for a reaction time of 60 min at 22° C. The concentration of TrkA in the assay is adjusted depending of the activity of the enzyme lot and is chosen appropriate to have the assay in the linear range, typical enzyme concentrations are in the range of about 20 pg/μL (final conc. in the 5 μL assay volume). The reaction is stopped by the addition of 5 μL of a solution of HTRF detection reagents (30 nM streptavidine-XL665 [Cis Biointernational] and 1.4 nM PT66-Eu-Chelate, an europium-chelate labelled anti-phospho-tyrosine antibody from Perkin Elmer [instead of the PT66-Eu-chelate PT66-Tb-Cryptate from Cis Biointernational can also be used]) in an aqueous EDTA-solution (100 mM EDTA, 0.2% (w/v) bovine serum albumin in 50 mM HEPES/NaOH pH 7.5).

The resulting mixture is incubated 1 h at 22° C. to allow the binding of the biotinylated phosphorylated peptide to the streptavidine-XL665 and the PT66-Eu-Chelate. Subsequently the amount of phosphorylated substrate is evaluated by measurement of the resonance energy transfer from the PT66-Eu-Chelate to the streptavidine-XL665. Therefore, the fluorescence emissions at 620 nm and 665 nm after excitation at 350 nm is measured in a HTRF reader, e.g. a Rubystar (BMG Labtechnologies, Offenburg, Germany) or a Viewlux (Perkin-Elmer). The ratio of the emissions at 665 nm and at 622 nm is taken as the measure for the amount of phosphorylated substrate. The data are normalised (enzyme reaction without inhibitor=0% inhibition, all other assay components but no enzyme=100% inhibition). Normally test compound are tested on the same microtiter plate at 10 different concentrations in the range of 20 μM to 1 nM (20 μM, 6.7 μM, 2.2 μM, 0.74 μM, 0.25 μM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values are calculated by a 4 parameter fit using an inhouse software.

AlphaScreen SureFire eIF4E Ser209 Phosphorylation Assay

The AlphaScreen SureFire eIF4E Ser209 phoshorylation assay is used to measure the phosphorylation of endogenous eIF4E in cellular lysates. The AlphaScreen SureFire technology allows the detection of phosphorylated proteins in cellular lysates. In this assay, sandwich antibody complexes, which are only formed in the presence of the analyte (p-eIF4E Ser209), are captured by AlphaScreen donor and acceptor beads, bringing them into close proximity. The excitation of the donor bead provokes the release of singlet oxygen molecules that triggers a cascade of energy transfer in the Acceptor beads, resulting in the emission of light at 520-620 nm.

Surefire EIF4e Alphascreen in A549 Cells with 20% FCS Stimulation

For the assay the AlphaScreen SureFire p-eIF4E Ser209 10K Assay Kit and the AlphaScreen ProteinA Kit (for 10K assay points) both from Perkin Elmer are used.

On day one 50.000 A549 cells are plated in a 96-well plate in 100 μL per well in growth medium (DMEM/Hams' F12 with stable Glutamin, 10% FCS) and incubated at 37° C. After attachment of the cells, medium is changed to starving medium (DMEM, 0.1% FCS, without Glucose, with Glutamin, supplemented with 5 g/L Maltose). On day two, test compounds are serially diluted in 50 μL starving medium with a final DMSO concentration of 1% and are added to A549 cells in test plates at a final concentration range from as high 10 μM to as low 10 nM depending on the activities of the tested compounds. Treated cells are incubated at 37° C. for 2 h. 37 ul FCS is added to the wells (=final FCS concentration 20%) for 20 min. Then medium is removed and cells are lysed by adding 50 μL lysis buffer. Plates are then agitated on a plate shaker for 10 min. After 10 min lysis time, 4 μL of the lysate is transferred to a 384 well plate (Proxiplate from Perkin Elmer) and 5 μL Reaction Buffer plus Activation Buffer mix containing AlphaScreen Acceptor beads is added. Plates are sealed with TopSeal-A adhesive film, gently agitated on a plate shaker for 2 hours at room temperature. Afterwards 2 μL Dilution buffer with AlphaScreen Donor beads are added under subdued light and plates are sealed again with TopSeal-A adhesive film and covered with foil. Incubation takes place for further 2 h gently agitation at room temperature. Plates are then measured in an EnVision reader (Perkin Elmer) with the AlphaScreen program. Each data point (compound dilution) is measured as triplicate.

The IC50 values are determined by means of a 4-parameter fit using the company's own software.

Proliferation Assays

The tumor cell proliferation assay which can be used to test the compounds of the present invention involves a readout called Cell Titer-Glow® Luminescent Cell Viability Assay developed by Promega® (B. A. Cunningham, "A Growing Issue: Cell Proliferation Assays, Modern kits ease quantification of cell growth", *The Scientist* 2001, 15(13), 26; S. P. Crouch et al., "The use of ATP bioluminescence as a measure of cell proliferation and cytotoxicity", *Journal of Immunological Methods* 1993, 160, 81-88), that measures inhibition of cell proliferation. Generation of a luminescent signal corresponds to the amount of ATP present, which is directly proportional to the number of metabolically active (proliferating) cells.

In Vitro Tumor Cell Proliferation Assay:

Cultivated tumour cells (MOLM-13 (human acute myeloid leukemia cells obtained from DSMZ # ACC 554), JJN-3 (human plasma cell leukemia cells obtained from DSMZ # ACC 541), Ramos (RA1) (human Burkitt's lymphoma cells obtained from ATCC # CRL-159)) are plated at a density of 2,500 cells/well (JJN-3), 3,000 cells/well (MOLM-13), 4,000 cells/well (Ramos (RA1)), in a 96-well multititer plate (Costar 3603 black/clear bottom) in 100 μL of their respective growth medium supplemented with 10% fetal calf serum. After 24 hours, the cells of one plate (zero-point plate) are measured for viability. Therefore, 70 μL/well CTG solution (Promega Cell Titer Glo solution (catalog # G755B and G756B)) is added to zero-point plate. The plates are mixed for two minutes on orbital shaker to ensure cell lysis and incubated for ten minutes at room temperature in the dark to stabilize luminescence signal. The samples are read on a VICTOR 3 plate reader. In parallel, serially test compounds are diluted in growth medium, and 50 μL of 3× dilutions/well are pipetted into the test plates (final concentrations: 0 μM, as well as in the range of 0.001-30 μM). The final concentration of the solvent dimethyl sulfoxide is 0.3-0.4%. The cells are incubated for 3 days in the presence of test substances. 105 μL/well CTG solution (Promega Cell Titer Glo solution (catalog # G755B and G756B)) is added to the test wells. The plates are mixed for 2 minutes on an orbital shaker to ensure cell lysis and incubated for 10 min at room temperature in the dark to stabilize luminescence signal. The samples are read on a VICTOR 3 plate reader. The change of cell number, in percent, is calculated by normalization of the measured values to the extinction values of the zero-point plate (=0%) and the extinction of the untreated (0 μm) cells (=100%). The $IC_{50}$ values (inhibitory concentration at 50% of maximal effect) are determined by means of a 4 parameter fit using the company's own software.

Overview Cell Lines for Proliferation Assays

| Cell line | Origin | Cell number/well | Culture Medium |
|---|---|---|---|
| MOLM-13 (obtained from DSMZ # ACC 554) | human acute myeloid leukemia | 3000 | RPMI 1640 with stable Glutamin with 10% Fetal Bovine Serum |
| JJN-3 (obtained from DSMZ # ACC 541) | human plasma cell leukemia | 2500 | 45% Dulbecco's Modified Eagle Medium with stable Glutamin, 45% Iscove's Modified Dulbecco's Media with stable Glutamin and 10% Fetal Bovine Serum |
| Ramos (RA1) (obtained from ATCC # CRL-159) | human Burkitt's lymphoma | 4000 | RPMI 1640 media with stable Glutamin with 10% Fetal Bovine Serum |

Kinase Selectivity Profiling

Often, kinase inhibitors show inhibitory action with respect to different kinases. In order to prevent undesirable side effects, the selectivity of a kinase inhibitor should be high. The selectivity can be determined e.g. by a target profiling in which the selectivity of compounds against various kinases is tested e.g. by Merck Millipore in a service called KinaseProfiler.

The compounds of the present invention are characterized by a high selectivity with respect to MKNK.

Thus the compounds of the present invention effectively inhibit MKNK1 and/or MKNK2 and are therefore suitable for the treatment or prophylaxis of diseases of uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by MKNK, more particularly in which the diseases of uncontrolled cell growth, proliferation and/or survival, inappropriate cellular immune responses, or inappropriate cellular inflammatory responses are haemotological tumours, solid tumours and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The invention claimed is:

1. A compound of general formula I:

I

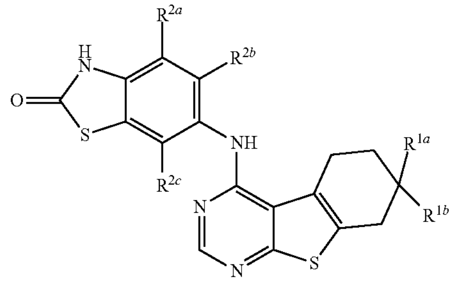

in which:

$R^{1a}$ represents a hydrogen atom or a group selected from: —O—$C_1$-$C_6$-alkyl, —$(CH_2)_r$—$R^8$, —$(CH_2)_r$—$NR^3R^4$, —$(CH_2)_r$—$N(R^4)C(=O)R^3$, —$(CH_2)_r$—$N(R^4)S(=O)_2R^3$, —$(CH_2)_r$—$C(=O)OR^3$, —$(CH_2)_r$—$C(=O)NR^3R^4$, —$(CH_2)_r$—$N(R^4)C(=O)OR^3$, —$(CH_2)_r$—$N(R^4)C(=O)N(H)R^3$, $R^{1b}$ represents a hydrogen atom or a group selected from: $C_1$-$C_6$-alkyl-, —$(CH_2)_r$—O—($C_1$-$C_6$-alkyl); or $R^{1a}$ and $R^{1b}$ together form an oxygen atom or a —O—($C_2$-$C_6$-alkylene)-O— group;

$R_{2a}$ represents a hydrogen atom or a halogen atom or a group selected from: $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —$N(H)R^5$, —$NR^5R^4$;

$R^{2b}$ represents a hydrogen atom or a halogen atom or a group selected from: $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —$N(H)R^5$, —$NR^5R^4$, —$N(H)C(=O)R^5$, —$N(R^4)C(=O)R^5$, —$N(H)C(=O)NR^5R^4$, —$N(R^4)C(=O)NR^5R^4$, —$C(=O)N(H)R^5$, —$C(=O)NR^5R^4$;

$R^{2c}$ represents a hydrogen atom or a halogen atom or a group selected from: $C_1$-$C_3$-alkyl-, $C_1$-$C_3$-alkoxy-, halo-$C_1$-$C_3$-alkyl-, halo-$C_1$-$C_3$-alkoxy-, hydroxy-, cyano-, —$N(H)R^5$, —$NR^5R^4$;

$R^3$ represents a hydrogen atom or a group selected from: $C_1$-$C_6$-alkyl-, $C_2$-$C_6$-alkynyl-, $C_3$-$C_6$-cycloalkyl-, —$(CH_2)_q$—($C_3$-$C_6$-cycloalkyl), —$(CH_2)_q$—O—($C_3$-$C_6$-cycloalkyl), 3- to 10-membered heterocycloalkyl, —$(CH_2)_q$-(3- to 10-membered heterocycloalkyl), —$(CH_2)_q$—O-(3- to 10-membered heterocycloalkyl), 4- to 10-membered heterocycloalkenyl, —$(CH_2)_q$-(4- to 10-membered heterocycloalkenyl), —$(CH_2)_q$—O-(4- to 10-membered heterocycloalkenyl), aryl, —$(CH_2)_q$-aryl, —$(CH_2)_q$—O-aryl, heteroaryl, —$(CH_2)_q$-heteroaryl, —$(CH_2)_q$—O-heteroaryl, —(3- to 10-membered heterocycloalkyl)-$(CH_2)_q$-(3- to 10-membered heterocycloalkyl), -(3- to 10-membered heterocycloalkyl)-$(CH_2)_q$-aryl, -(3- to 10-membered heterocycloalkyl)-$(CH_2)_q$-heteroaryl, said group being optionally substituted, identically or differently, with 1, 2, 3, 4 or 5 $R^8$ groups; or when 2 $R^8$ groups are present ortho to each other on an aryl- or heteroaryl-ring, said 2 $R^8$ groups together form a bridge:

*$O(CH_2)_pO$*, * NH(C(=O))NH*, wherein * represent the point of attachment to said aryl- or heteroaryl-ring;

$R^4$ represents a hydrogen atom or a group selected from: $C_1$-$C_6$-alkyl-, —$(CH_2)_q$-aryl, $C_1$-$C_6$-alkoxy-$C_1$-$C_6$-alkyl-; or $NR^3R^4$ together represent a 3- to 10-membered heterocycloalkyl group, a benzo fused 3- to 10-membered heterocycloalkyl group or a 4- to 10-membered heterocycloalkenyl group;

said 3- to 10-membered heterocycloalkyl or 4- to 10-membered heterocycloalkenyl group being optionally substituted, one or more times, identically or differently, with halo-, hydroxyl-, cyano-, nitro-, $C_1$-$C_6$-alkyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $C_2$-$C_6$-alkenyl-, $C_2$-$C_6$-alkynyl-, $C_3$-$C_6$-cycloalkyl-, —$(CH_2)_q$-aryl, —$(CH_2)_q$-heteroaryl, —$N(R^4)C(=O)R^5$, —$NR^5R^4$ or —$(CH_2)_r$—$C(=O)NR^6R^7$;

$R^5$ represents a hydrogen atom, a $C_1$-$C_6$-alkyl- or a $C_3$-$C_6$-cycloalkyl-group;

$R^6$ represents a hydrogen atom, a $C_1$-$C_6$-alkyl- or a $C_3$-$C_6$-cycloalkyl-group;

$R^7$ represents a hydrogen atom, a $C_1$-$C_6$-alkyl- or a $C_3$-$C_6$-cycloalkyl-group; or $NR^6R^7$ together represent a 3- to 10-membered heterocycloalkyl group;

$R^8$ represents halo-, azido-, hydroxy-, oxo-(O=), cyano-, nitro-, $C_1$-$C_6$-alkyl-, $C_2$-$C_6$-alkenyl-, $C_2$-$C_6$-alkynyl-, halo-$C_1$-$C_6$-alkyl-, $C_1$-$C_6$-alkoxy-, halo-$C_1$-$C_6$-alkoxy-, hydroxy-$C_1$-$C_6$-alkyl-, $C_1$-$C_6$-alkoxy-$C_1$-$C_6$-alkyl-, halo-$C_1$-$C_6$-alkoxy-$C_1$-$C_6$-alkyl-, $R^5$—O—, —$C(=O)R^5$, —$C(=O)O$—$R^5$, —$OC(=O)$—$R^5$, —$N(H)C(=O)R^5$, —$N(R^4)C(=O)R^5$, —$N(H)C(=O)NR^5R^4$, —$N(R_4)C(=O)NR^5R^4$, —$N(R^4)C(=O)OR^5$, —$N(H)R^5$, —$NR^5R^4$, —$C(=O)N(H)R^5$, —$C(=O)NR^5R^4$, $R^4$—S—, $R^4$—S(=O)—, $R^4$—$S(=O)_2$—, —$N(H)S(=O)R^4$, —$N(R^4)S(=O)R^4$, —$S(=O)N(H)R^5$, —$S(=O)NR^5R^4$, —$N(H)S(=O)_2R^4$, —$N(R^4)S(=O)_2R^4$, —S(=O)2N(H)$R^5$, —S(=O)2$NR^5R^4$, —$S(=O)(=NR^5)R^4$, —$S(=O)(=NR^4)R^5$ or —$N=S(=O)(R^5)R^4$;

p represents an integer of 1 or 2;

q represents an integer of 1, 2 or 3;

r represents an integer of 0, 1 or 2;

or a tautomer, an N-oxide, a hydrate, a solvate, or a salt thereof.

2. The compound of claim 1, wherein $R^{1a}$ represents a group selected from:

—C(═O)O—$R^3$, —C(═O)N(H)$R^3$, —C(═O)$NR^3R^4$;

$R^{1b}$ represents a hydrogen atom;

or a tautomer, an N-oxide, a hydrate, a solvate, or a salt thereof.

3. The compound of claim 1, wherein $R^{2a}$ represents a hydrogen atom;

$R^{2b}$ represents a hydrogen atom or a halogen atom or a $C_1$-$C_3$-alkoxy-group;

$R^{2c}$ represents a hydrogen atom;

or a tautomer, an N-oxide, a hydrate, a solvate, or a salt thereof.

4. The compound of claim 1, wherein $R^3$ represents a hydrogen atom or a group selected from:

$C_1$-$C_6$-alkyl-, $C_3$-$C_6$-cycloalkyl, —$(CH_2)_q$—($C_3$-$C_6$-cycloalkyl), 3- to 10-membered heterocycloalkyl, —$(CH_2)_q$-(3- to 10-membered heterocycloalkyl), aryl, —$(CH_2)_q$-aryl, —$(CH_2)_q$—O-aryl, heteroaryl, —$(CH_2)_q$-heteroaryl, —$(CH_2)_q$—O-heteroaryl;

said group being optionally substituted, identically or differently, with 1, 2, 3 or 4 $R^8$ groups; or when 2 $R^8$ groups are present ortho to each other on an aryl- or heteroaryl-ring, said 2 $R^8$ groups together form a bridge:

*O$(CH_2)_p$O*, *NH(C(═O))NH*, wherein * represent the point of attachment to said aryl- or heteroaryl-ring;

or a tautomer, an N-oxide, a hydrate, a solvate, or a salt thereof.

5. The compound of claim 1, wherein $R^{1a}$ represents a group selected from:

—C(═O)N(H)$R^3$, —C(═O)$NR^3R^4$;

$R^{2b}$ represents a $C_1$-$C_3$-alkoxy-group;

or a tautomer, an N-oxide, a hydrate, a solvate, or a salt thereof.

6. The compound of claim 1, which is selected from the group consisting of:

(RS)-ethyl 4-[(2-oxo-2,3-dihydro-1,3-benzothiazol-6-yl)amino]-5,6,7,8-tetrahydro[1]benzothieno[2,3-d]pyrimidine-7-carboxylate, (RS)-4-[(2-oxo-2,3-dihydro-1,3-benzothiazol-6-yl)amino]-5,6,7,8-tetrahydro[1]benzothieno[2,3-d]pyrimidine-7-carboxylic acid, (RS)—N-ethyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)—N-cyclopropyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)—N-isopropyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)—N-isobutyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)-4-[(2-oxo-2,3-dihydro-1,3-benzothiazol-6-yl)amino]-N-(3,3,3-trifluoropropyl)-5,6,7,8-tetrahydro[1]benzothieno[2,3-d]pyrimidine-7-carboxamide, (RS)-4-[(2-oxo-2,3-dihydro-1,3-benzothiazol-6-yl)amino]-N-phenyl-5,6,7,8-tetrahydro[1]benzothieno[2,3-d]pyrimidine-7-carboxamide, (RS)—N-benzyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)-4-[(2-oxo-2,3-dihydro-1,3-benzothiazol-6-yl)amino]-N-[3-(trifluoromethyl)benzyl]-5,6,7,8-tetrahydro[1]benzothieno[2,3-d]pyrimidine-7-carboxamide, (RS)—N-methyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)—N-(cyclopropylmethyl)-4-[(2-oxo-2,3-dihydro-1,3-benzothiazol-6-yl)amino]-5,6,7,8-tetrahydro[1]benzothieno[2,3-d]pyrimidine-7-carboxamide, (RS)—N,N-dimethyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)—N-(3-fluorobenzyl)-4-[(2-oxo-2,3-dihydro-1,3-benzothiazol-6-yl)amino]-5,6,7,8-tetrahydro[1]benzothieno[2,3-d]pyrimidine-7-carboxamide, (RS)-6-{[7-methoxy-7-(methoxymethyl)-5,6,7,8-tetrahydro[1]benzothieno[2,3-d]pyrimidin-4-yl]amino}-1,3-benzothiazol-2(3H)-one, (RS)-6-[(7-methyl-5,6,7,-tetrahydro[1]benzothieno[2,3-d]pyrimidin-4-yl)amino]-1,3-benzothiazol-2(3H)-one, (RS)-6-{[7-(hydroxymethyl)-5,6,7,8-tetrahydro[1]benzothieno[2,3-d]pyrimidin-4-yl]amino}-1,3-benzothiazol-2(3H)-one, (RS)-6-{[7-(azidomethyl)-5,6,7,8-tetrahydro[1]benzothieno[2,3-d]pyrimidin-4-yl]amino}-1,3-benzothiazol-2(3H)-one, (RS)-6-{[7-(aminomethyl)-5,6,7,8-tetrahydro[1]benzothieno[2,3-d]pyrimidin-4-yl]amino}-1,3-benzothiazol-2(3H)-one, (RS)-2-methyl-N-({4-[(2-oxo-2,3-dihydro-1,3-benzothiazol-6-yl)amino]-5,6,7,8-tetrahydro[1]benzothieno[2,3-d]pyrimidin-7-yl}methyl)propanamide, (RS)-1-({4-[(2-oxo-2,3-dihydro-1,3-benzothiazol-6-yl)amino]-5,6,7,8-tetrahydro[1]benzothieno[2,3-d]pyrimidin-7-yl}methyl)-3-propan-2-ylurea, (2R)-2-hydroxy-N-({(7RS)-4-[(2-oxo-2,3-dihydro-1,3-benzothiazol-6-yl)amino]-5,6,7,8-tetrahydro[1]benzothieno[2,3-d]pyrimidin-7-yl}methyl)-3-phenylpropanamide, (RS)-propan-2-yl ({4-[(2-oxo-2,3-dihydro-1,3-benzothiazol-6-yl)amino]-5,6,7,8-tetrahydro[1]benzothieno[2,3-d]pyrimidin-7-yl}methyl)carbamate, (RS)-2-hydroxy-2-methyl-N-({4-[(2-oxo-2,3-dihydro-1,3-benzothiazol-6-yl)amino]-5,6,7,8-tetrahydro[1]benzothieno[2,3-d]pyrimidin-7-yl}methyl)propanamide, (2RS)-2-hydroxy-N-({(7RS)-4-[(2-oxo-2,3-dihydro-1,3-benzothiazol-6-yl)amino]-5,6,7,8-tetrahydro[1]benzothieno[2,3-d]pyrimidin-7-yl}methyl)propanamide, tert-butyl {(2R)-4-hydroxy-1-oxo-1-[({(7RS)-4-[(2-oxo-2,3-dihydro-1,3-benzothiazol-6-yl)amino]-5,6,7,8-tetrahydro[1]benzothieno[2,3-d]pyrimidin-7-yl}methyl)amino]butan-2-yl}carbamate, (RS)—N-({4-[(2-oxo-2,3-dihydro-1,3-benzothiazol-6-yl)amino]-5,6,7,8-tetrahydro[1]benzothieno[2,3-d]pyrimidin-7-yl}methyl)propane-2-sulfonamide, (RS)-6-({7-[(4-methylpiperazin-1-yl)carbonyl]-5,6,7,8-tetrahydro[1]benzothieno[2,3-d]pyrimidin-4-yl}amino)-1,3-benzothiazol-2(3H)-one, (RS)-ethyl 4-[(5-methoxy-2-oxo-2,3-dihydro-1,3-benzothiazol-6-yl)amino]-5,6,7,8-tetrahydro[1]benzothieno[2,3-d]pyrimidine-7-carboxylate, (RS)-4-[(5-methoxy-2-oxo-2,3-dihydro-1,3-benzothiazol-6-yl)amino]-Nropan-2-yl)-5,6,7,8-tetrahydro[1]benzothieno[2,3-d]pyrimidine-7-carboxamide, N-({4-[(2-oxo-2,3-dihydro-1,3-benzothiazol-6-yl)amino]-5,6,7,8-tetrahydro[1]benzothieno[2,3-d]pyrimidin-7-(RS)-yl}methyl)-L-homoserinamide, 4-[(5-methoxy-2-oxo-2,3-dihydro-1,3-benzothiazol-6-yl)amino]-5,6,7,8-tetrahydro[1]benzothieno[2,3-d]pyrimidine-7-carboxylic acid, (RS)—N-butyl-N-(cyanomethyl)-4-[(2-oxo-2,3-dihydro-1,3-benzothiazol-6-yl)amino]-5,6,7,8-tetrahydro[1]benzothieno[2,3-d]pyrimidine-7-carboxamide, (RS)—N-[2-(dimethylamino)ethyl]-N-methyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)—N-benzyl-N-[2-(dimethylamino)ethyl]-4-[(2-oxo-2,3-dihydro-1,3-benzothiazol-6-yl)amino]-5,6,7,8-tetrahydro[1]benzothieno[2,3-d]pyrimidine-7-carboxamide, (RS)-6-({7-[(4-methylpiperazin-1-yl)carbonyl]-5,6,7,8-tetrahydro[1]benzothieno[2,3-d]pyrimidin-4-yl}amino)-1,3-benzothiazol-2(3H)-one, 6-({7-[(4-benzylpiperazin-1-yl)carbonyl]-5,6,7,8-tetrahydro[1]benzothieno[2,3-d]pyrimidin-4-yl}amino)-1,3-benzothiazol-2(3H)-one, (RS)—N-methyl-4-[(2-oxo-2,3-dihydro-1,3-benzothiazol-6-yl)amino]-Nrop-2-yn-1-yl)-5,6,7,8-tetrahydro[1]benzothieno[2,3-d]pyrimidine-7-carboxamide, (RS)-6-[(7-{[4-(pyridin-2-yl)piperazin-1-yl]carbonyl}-5,6,7,8-tetrahydro[1]benzothieno[2,3-d]pyrimidin-4-yl)amino]-1,3-benzothiazol-2(3H)-one, (RS)—N-butyl-N-methyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)—N-(4-methoxyphenyl)-N-methyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)-6-{[7-({4-[2-oxo-2-(pyrrolidin-1-yl)ethyl]piperazin-1-yl}carbonyl)-5,6,7,8-tetrahydro[1]benzothieno[2,3-d]pyrimidin-4-yl]amino}-1,3-benzothiazol-2(3H)-one, (RS)-6-[(7-{[4-(1,3-benzodioxol-5-ylmethyl)piperazin-1-yl]carbonyl}-5,6,7,8-tetrahydro[1]benzothieno[2,3-d]pyrimidin-4-yl)amino]-1,3-benzothiazol-2(3H)-one, (RS)-6-{[7-(azetidin-1-ylcarbonyl)-5,6,7,8-tetrahydro[1]benzothieno[2,3-d]pyrimidin-4-yl]amino}-1,3-benzothiazol-2(3H)-one, 6-{[(7RS)-7-{[(2RS)-2-(hydroxymethyl)pyrrolidin-1-yl]carbonyl}-5,6,7,8-tetrahydro[1]benzothieno[2,3-d]pyrimidin-4-yl]amino}-1,3-benzothiazol-2(3H)-one, (RS)-6-({7-[(4-acetylpiperazin-1-yl)carbonyl]-5,6,7,8-tetrahydro[1]benzothieno[2,3-d]pyrimidin-4-yl}amino)-1,3-benzothiazol-2(3H)-one, (RS)—N-(2-cyanoethyl)-N-methyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)—N-(cyanomethyl)-N-methyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)-6-({7-[(4-methylpiperidin-1-yl)carbonyl]-5,6,7,8-tetrahydro[1]benzothieno[2,3-d]pyrimidin-4-yl}amino)-1,3-benzothiazol-2(3H)-one, 6-{[(7RS)-7-{[(3RS)-3-hydroxypyrrolidin-1-yl]carbonyl}-5,6,7,8-tetrahydro[1]benzothieno[2,3-d]pyrimidin-4-yl]amino}-1,3-benzothiazol-2(3H)-one, (RS)—N,N-bis(2-methoxyethyl)-4-[(2-oxo-2,3-dihydro-1,3-benzothiazol-6-yl)amino]-5,6,7,8-tetrahydro[1]benzothieno[2,3-d]pyrimidine-7-carboxamide, 6-{[(7RS)-7-{[(3RS)-3-hydroxypiperidin-1-yl]carbonyl}-5,6,7,8-tetrahydro[1]benzothieno[2,3-d]pyrimidin-4-yl]amino}-1,3-benzothiazol-2(3H)-one, (RS)—N-(2-hydroxyethyl)-N-isopropyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)-6-{[7-(1,3-dihydro-2H-isoindol-2-ylcarbonyl)-5,6,7,8-tetrahydro[1]benzothieno[2,3-d]pyrimidin-4-yl]amino}-1,3-benzothiazol-2(3H)-one, (7RS)—N-methyl-4-[(2-oxo-2,3-dihydro-1,3-benzothiazol-6-yl)amino]-N-[(2RS)-tetrahydrofuran-2-ylmethyl]-5,6,7,8-tetrahydro[1]benzothieno[2,3-d]pyrimidine-7-carboxamide, (RS)-6-[(7-{[4-(3-hydroxypropyl)piperazin-1-yl]carbonyl}-5,6,7,8-tetrahydro[1]benzothieno[2,3-d]pyrimidin-4-yl)amino]-1,3-benzothiazol-2(3H)-one, (RS)—N-isobutyl-N-methyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)—N-ethyl-N-methyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)-6-({7-[(4-ethylpiperazin-1-yl)carbonyl]-5,6,7,8-tetrahydro[1]benzothieno[2,3-d]pyrimidin-4-yl}amino)-1,3-benzothiazol-2(3H)-one, N-methyl-N-[(3RS)-1-({(7RS)-4-[(2-oxo-2,3-dihydro-1,3-benzothiazol-6-yl)amino]-5,6,7,8-tetrahydro[1]benzothieno[2,3-d]pyrimidin-7-yl}carbonyl)pyrrolidin-3-yl]acetamide, (RS)—N-[2-(dimethylamino)-2-oxoethyl]-N-methyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)—N-(2-cyanoethyl)-N-ethyl-4-[(2-oxo-2,3-dihydro-1,3-benzothiazol-6-yl)amino]-5,6,7,8-tetrahydro[1]benzothieno[2,3-d]pyrimidine-7-carboxamide, 6-({(7RS)-7-[(9aRS)-octahydro-2H-pyrido[1,2-a]pyrazin-2-ylcarbonyl]-5,6,7,8-tetrahydro[1]benzothieno[2,3-d]pyrimidin-4-yl}amino)-1,3-benzothiazol-2(3H)-one, 6-{[(7RS)-7-{[(3RS)-3-fluoropiperidin-1-yl]carbonyl}-5,6,7,8-tetrahydro[1]benzothieno[2,3-d]pyrimidin-4-yl]amino}-1,3-benzothiazol-2(3H)-one, (RS)—N-(4-hydroxybutyl)-N-methyl-4-[(2-oxo-2,3-dihydro-1,3-benzothiazol-6-yl)amino]-5,6,7,8-tetrahydro[1]benzothieno[2,3-d]pyrimidine-7-carboxamide, (RS)—N-(3-hydroxypropyl)-N-methyl-4-[(2-oxo-2,3-dihydro-1,3-benzothiazol-6-yl)amino]-5,6,7,8-tetrahydro[1]benzothieno[2,3-d]pyrimidine-7-carboxamide, 6-{[(7RS)-7-{[(2RS,6RS)-2,6-dimethylmorpholin-4-yl]carbonyl}-5,6,7,8-tetrahydro[1]benzothieno[2,3-d]pyrimidin-4-yl]amino}-1,3-benzothiazol-2(3H)-one, (RS)—N-(2-methoxyethyl)-4-[(2-oxo-2,3-dihydro-1,3-benzothiazol-6-yl)amino]-N-propyl-5,6,7,8-tetrahydro[1]benzothieno[2,3-d]pyrimidine-7-carboxamide, (RS)—N-ethyl-N-(2-methoxyethyl)-4-[(2-oxo-2,3-dihydro-1,3-benzothiazol-6-yl)amino]-5,6,7,8-tetrahydro[1]benzothieno[2,3-d]pyrimidine-7-carboxamide, (RS)-6-[(7-{[4-(hydroxymethyl)piperidin-1-yl]carbonyl}-5,6,7,8-tetrahydro[1]benzothieno[2,3-d]pyrimidin-4-yl)amino]-1,3-benzothiazol-2(3H)-one, (RS)-6-[(7-{[4-(2-methoxyethyl)piperazin-1-yl]carbonyl}-5,6,7,8-tetrahydro[1]benzothieno[2,3-d]pyrimidin-4-yl)amino]-1,3-benzothiazol-2(3H)-one, 6-{[(7RS)-7-{[(3RS)-3-(dimethylamino)pyrrolidin-1-yl]carbonyl}-5,6,7,8-tetrahydro[1]benzothieno[2,3-d]pyrimidin-4-yl]amino}-1,3-benzothiazol-2(3H)-one, 6-{[(7RS)-7-{[(1RS,4RS)-5-methyl-2,5-diazabicyclo[2.2.1]hept-2-yl]carbonyl}-5,6,7,8-tetrahydro[1]benzothieno[2,3-d]pyrimidin-4-yl]amino}-1,3-benzothiazol-2(3H)-one, (3RS)-1-({(7RS)-4-[(2-oxo-2,3-dihydro-1,3-benzothiazol-6-yl)amino]-5,6,7,8-tetrahydro[1]benzothieno[2,3-d]pyrimidin-7-yl}carbonyl)piperidine-3-carbonitrile, (RS)-1-({4-[(2-oxo-2,3-dihydro-1,3-benzothiazol-6-yl)amino]-5,6,7,8-tetrahydro[1]benzothieno[2,3-d]pyrimidin-7-yl}carbonyl)piperidine-4-carbonitrile, 6-{[(7RS)-7-{[(2RS)-2-(methoxymethyl)pyrrolidin-1-yl]carbonyl}-5,6,7,8-tetrahydro[1]benzothieno[2,3-d]pyrimidin-4-yl]amino}-1,3-benzothiazol-2(3H)-one, (RS)-6-[(7-{[4-(cyclopropylmethyl)piperazin-1-yl]carbonyl}-5,6,7,8-tetrahydro[1]benzothieno[2,3-d]pyrimidin-4-yl)amino]-1,3-benzothiazol-2(3H)-one, (RS)-6-[(7-{[3-(piperidin-1-yl)azetidin-1-yl]carbonyl}-5,6,7,8-tetrahydro[1]benzothieno[2,3-d]pyrimidin-4-yl)amino]-1,3-benzothiazol-2(3H)-one, (RS)—N-(2,2-dimethyltetrahydro-2H-pyran-4-yl)-N-methyl-4-[(2-oxo-2,3-dihydro-1,3-benzothiazol-6-yl)amino]-5,6,7,8-tetrahydro[1]benzothieno[2,3-d]pyrimidine-7-carboxamide, 6-{[(7RS)-7-{[(3RS)-3-(2-hydroxyethyl)-4-methylpiperazin-1-yl]carbonyl}-5,6,7,8-tetrahydro[1]benzothieno[2,3-d]pyrimidin-4-yl]amino}-1,3-benzothiazol-2(3H)-one, (RS)—N-methyl-N-[2-(morpholin-4-yl)ethyl]-4-[(2-oxo-2,3-dihydro-1,3-benzothiazol-6-yl)amino]-5,6,7,8-tetrahydro[1]benzothieno[2,3-d]pyrimidine-7-carboxamide, (RS)-6-{[7-(2-oxa-6-azaspiro[3.3]hept-6-ylcarbonyl)-5,6,7,8-tetrahydro[1]benzothieno[2,3-d]pyrimidin-4-yl]amino}-1,3-benzothiazol-2(3H)-one, 6-{[(7RS)-7-{[(3RS)-3-methoxypiperidin-1-yl]carbonyl}-5,6,7,8-tetrahydro[1]benzothieno[2,3-d]pyrimidin-4-yl]amino}-1,3-benzothiazol-2(3H)-one, (RS)-4-[(5-methoxy-2-oxo-2,3-dihydro-1,3-benzothiazol-6-yl)amino]-N,N-dimethyl-5,6,7,8-tetrahydro[1]benzothieno[2,3-d]pyrimidine-7-carboxamide, (RS)—N-ethyl-N-isopropyl-4-[(5-methoxy-2-oxo-2,3-dihydro-1,3-benzothiazol-6-yl)amino]-5,6,7,8-tetrahydro[1]benzothieno[2,3-d]pyrimidine-7-carboxamide, (RS)—N-(2-methoxyethyl)-4-[(5-methoxy-2-oxo-2,3-dihydro-1,3-benzothiazol-6-yl)amino]-N-propyl-5,6,7,8-tetrahydro[1]benzothieno[2,3-d]pyrimidine-7-carboxamide, (RS)—N-butyl-N-(cyanomethyl)-4-[(5-methoxy-2-oxo-2,3-dihydro-1,3-benzothiazol-6-yl)amino]-5,6,7,8-tetrahydro[1]benzothieno[2,3-d]pyrimidine-7-carboxamide, (RS)—N-butyl-4-[(5-methoxy-2-oxo-2,3-dihydro-1,3-benzothiazol-6-yl)amino]-N-methyl-5,6,7,8-tetrahydro[1]benzothieno[2,3-d]pyrimidine-7-carboxamide, (RS)—N-ethyl-N-(2-methoxyethyl)-4-[(5-methoxy-2-oxo-2,3-dihydro-1,3-benzothiazol-6-yl)amino]-5,6,7,8-tetrahydro[1]benzothieno[2,3-d]pyrimidine-7-carboxamide, (RS)-1-({4-[(2-oxo-2,3-dihydro-1,3-benzothiazol-6-yl)amino]-5,6,7,8-tetrahydro[1]benzothieno[2,3-d]pyrimidin-7-yl}carbonyl)azetidine-3-carbonitrile, (RS)—N-benzyl-N-[2-(dimethylamino)ethyl]-4-[(5-methoxy-2-oxo-2,3-dihydro-1,3-benzothiazol-6-yl)amino]-5,6,7,8-tetrahydro[1]benzothieno[2,3-d]pyrimidine-7-carboxamide, (RS)—N,N-bis(2-methoxyethyl)-4-[(5-methoxy-2-oxo-2,3-dihydro-1,3-benzothiazol-6-yl)amino]-5,6,7,8-tetrahydro[1]benzothieno[2,3-d]pyrimidine-7-carboxamide, (RS)-6-{[7-(1-oxa-6-azaspiro[3.3]hept-6-ylcarbonyl)-5,6,7,8-tetrahydro[1]benzothieno[2,3-d]pyrimidin-4-yl]amino}-1,3-benzothiazol-2(3H)-one, or a tautomer, an N-oxide, a hydrate, a solvate, or a salt thereof.

7. A method of preparing a compound according to claim 1, comprising reacting an intermediate compound of general formula II:

II

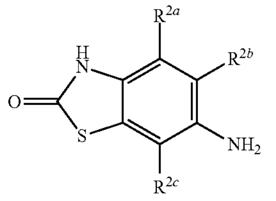

in which $R^{2a}$, $R^{2b}$, and $R^{2c}$ are as defined in claim 1 with an intermediate compound of general formula III:

III

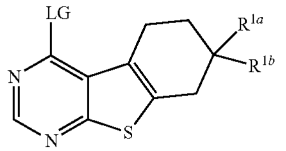

in which $R^{1a}$ and $R^{1b}$ are as defined in claim 1, and LG represents a leaving group;

thus providing a compound of general formula I:

I

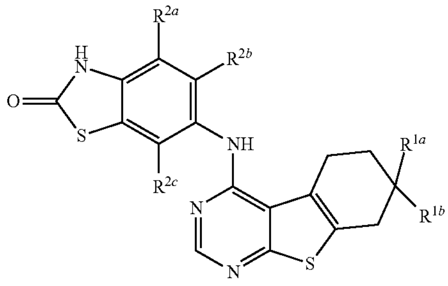

in which $R^{1a}$, $R^{1b}$, $R^{2a}$, $R^{2b}$, and $R^{2c}$ are as defined in claim 1.

8. A pharmaceutical composition comprising a compound of general formula I, or a stereoisomer, a tautomer, an N-oxide, a hydrate, a solvate, or a pharmaceutically acceptable salt thereof according to claim 1, and a pharmaceutically acceptable diluent or carrier.

9. A pharmaceutical combination comprising:

a compound of general formula I, or a stereoisomer, a tautomer, an N-oxide, a hydrate, a solvate, or a pharmaceutically acceptable salt thereof according to claim 1, and one or more chemotherapeutic anti-cancer agents or target-specific anti-cancer agents.

* * * * *